United States Patent
Dyckman et al.

(10) Patent No.: US 7,456,194 B2
(45) Date of Patent: Nov. 25, 2008

(54) IMIDAZO-FUSED OXAZOLO [4,5-B]PYRIDINE AND IMIDAZO-FUSED THIAZOLO[4,5-B]PYRIDINE BASED TRICYCLIC COMPOUNDS AND PHARMACEUTICAL COMPOSITIONS COMPRISING SAME

(75) Inventors: Alaric Dyckman, Mercerville, NJ (US); William J. Pitts, Newtown, PA (US); Makonen Belema, North Haven, CT (US); Patrice Gill, Chateauguay (CA); James Kempson, Princeton, NJ (US); Yuping Qiu, Glastonbury, CT (US); Claude Quesnelle, Brossard (CA); Steven H. Spergel, Warrington, PA (US); F. Christopher Zusi, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/272,401

(22) Filed: Nov. 10, 2005

(65) Prior Publication Data

US 2006/0106051 A1    May 18, 2006

Related U.S. Application Data

(60) Provisional application No. 60/627,761, filed on Nov. 12, 2004.

(51) Int. Cl.
A61K 31/4365 (2006.01)
A61K 31/437 (2006.01)
C07D 471/14 (2006.01)
C07D 471/16 (2006.01)

(52) U.S. Cl. .................................. 514/293; 546/82
(58) Field of Classification Search .............. 546/82; 514/293
See application file for complete search history.

(56) References Cited

U.S. PATENT DOCUMENTS

| | | |
|---|---|---|
| 6,933,294 B2 | 8/2005 | Belema et al. |
| 2003/0045545 A1 | 3/2003 | Gerster et al. |
| 2003/0078277 A1 | 4/2003 | Hibi et al. |
| 2003/0212093 A1 | 11/2003 | Gerster et al. |
| 2004/0204432 A1 | 10/2004 | Qiu et al. |
| 2005/0038054 A1 | 2/2005 | Combs et al. |
| 2005/0101626 A1* | 5/2005 | Pitts et al. ........... 514/292 |

FOREIGN PATENT DOCUMENTS

| | | |
|---|---|---|
| WO | WO 01/00587 | 1/2001 |
| WO | WO2004/106293 | 12/2004 |

OTHER PUBLICATIONS

U.S. Appl. No. 11/271,598, filed Nov. 10, 2005, Das et al., Not yet published.
J. Burke et al., "BMS-34541 is a Highly Selective Inhibitor of IKB Kinase That Binds at an Allosteric Site of the Enzyme and Blocks NF-KB-Dependent Transcription in Mice", Journal of Biological Chemistry, vol. 278, No. 3, pp. 1450-1456, 2003.
J. Burke, "Targeting IKB Kinase for the Treatment of Inflammatory and Other Disorders", Current Opinion in Drug Discovery & Development, vol. 6, No. 5, pp. 720-728, 2003.
I. Nahar et al., "Infliximab Treatment of Rheumatoid Arthritis and Crohn's Disease", Annals of Pharmacotherapy, vol. 37, pp. 1256-1265, 2003.
J. Braun et al., "Overview of the Use of the Anti-TNF Agent Infliximab in Chronic Inflammatory Diseases", Expert Opinion Biol. Ther., vol. 3, No. 1, pp. 141-168, 2003.
G. Keating et al., "Infliximab an Updated Review of its Use in Crohn's Disease and Rheumatoid Arthritis", Biodrugs, vol. 16, No. 2, pp. 111-148, 2002.
W. Sandborn et al., "Infliximab in the Treatment of Crohn's Disease: A User's Guide for Clinicians", American Journal of Gastroenterology, vol. 97, No. 12, pp. 2962-2972, 2002.
J. Weinberg, "An Overview of Infliximab, Etanercept, Efalizumab, and Alefacept as Biologic Therapy for Psoriasis", Clinical Therapeutics, vol. 25, No.10, pp. 2487-2505, 2003.

* cited by examiner

Primary Examiner—Rita J Desai
(74) Attorney, Agent, or Firm—Mary Van Atten

(57) ABSTRACT

The present invention provides for pyrazolopurine-based tricyclic compounds having the formula (I),

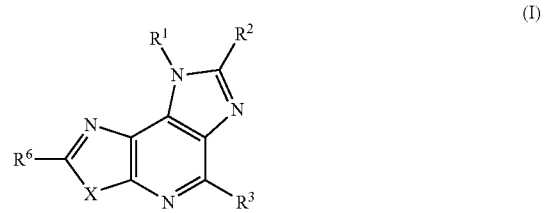

wherein $R^1$, $R^2$, $R^3$, and $R^6$ are as described herein. The present invention further provides pharmaceutical compositions comprising such compounds, as well as the use of such compounds for treating inflammatory and immune diseases.

6 Claims, No Drawings

IMIDAZO-FUSED OXAZOLO [4,5-B]PYRIDINE AND IMIDAZO-FUSED THIAZOLO[4,5-B]PYRIDINE BASED TRICYCLIC COMPOUNDS AND PHARMACEUTICAL COMPOSITIONS COMPRISING SAME

CROSS REFERENCE TO RELATED APPLICATIONS

The present application claims the priority benefit of U.S. Provisional Application No. 60/627,761, filed Nov. 12, 2004, which is expressly incorporated fully herein by reference.

FIELD OF THE INVENTION

The present invention relates to imidazo-fused oxazolo[4,5-b]pyridine and imidazo-fused thiazolo[4,5-b]pyridine based tricyclic compounds, to methods of using the compounds in treating inflammatory and immune diseases, and cancer and to pharmaceutical compositions comprising same.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases such as septic shock, hematopoiesis, tumors, and inflammatory disorders of the central nervous system, including HIV encephalitis, cerebral malaria, and meningitis. Additionally, certain neurodegenerative diseases such as Alzheimer's disease, Parkinson's disease, and Creutzfeldt-Jacob disease also are reportedly associated with enhanced TNF-α levels. See, e.g., Arvin et al., "*The Role of Inflammation and Cytokines in Brain Injury,*" Neuroscience and Biobehavioral Reviews, Vol. 20, No. 3 (1996), at pp. 445-452. More recently agents which inhibit the action of TNF-α have demonstrated clinical utility in a variety of diseases such as rheumatoid arthritis, psoriasis, and inflammatory bowel disease. See, e.g. Keating, et al. "*Infliximab: An Updated Review of its use in Crohn's Disease and Rheumatoid Arthritis*" BioDrugs Vol 16, (2002) pp. 111-148, and Hanns-Martin, et al. "*Perspectives for TNF-alpha-targeting Therapies.*" Arthritis Res. Vol 4. Supp 3 (2002) pp. S17-24.

Accordingly, various classes of drugs have been researched and developed to inhibit TNF-α production at both transcriptional and translational levels, e.g., corticosteroids, rolipram (a phosphodiesterase IV inhibitor suppressing TNF-α mRNA synthesis), calphostin, and imidazole-type cytokine suppressing anti-inflammatory drugs (CSAIDs or P-38 inhibitors). These drugs are useful in treating a variety of diseases. See Dinarello, "*Role of Pro-and Anti-Inflammatory Cytokines During Inflammation: Experimental and Clinical Findings, Review*", Vol. 0393-974X (1997), at pp. 91-103.

Recently, attention has focused on the role of Nuclear factor κB (NF-κB) in the activation pathway that leads to production of TNF-α and other inflammatory cytokines and gene products. Besides TNF-α, NF-κB is involved in the regulation of a variety of genes involved in immune function and inflammation. These include the cytokines IL-1, IL-2, IL-6, IL-2Rα, and GM-GSF, the chemokines IL-8, MCP-1 (CCR2), and RANTES, the adhesion molecules, intercellular adhesion molecule-1 (ICAM-1), vascular cellular adhesion molecule-1 (VCAM-1) and E-selectin, the proteases matrix metalloproteinase-1 (MMP-1), MMP-9 and MMP-13, and the pro-inflammatory enzymes cyclooxygenase-2 (COX-2), iNOS, and cPLA$_2$. Thus, inhibition of NF-κB and/or its activation pathway provides a means for treating various diseases including autoimmune diseases, inflammatory diseases, Alzheimer's disease, atherosclerosis, oncogenesis, and so forth by a variety of modes of action (i.e. cytokine reduction, chemokine reduction, reduction of adhesion molecule expression, decreased expression of certain proteases implicated in inflammatory and immune disease processes, and decreased production of enzymes which produce pro-inflammatory mediators) which have been implicated in a variety of disease progression. See, e.g., Baldwin, "*The NF-κB and I κB Proteins: New Discoveries and Insights,*" Annual Rev. Immunol., Vol. 14 (1996), at pp. 649-81; see also Christman et al., "*Impact of Basic Research on Tomorrow's Medicine, The Role of Nuclear Factor-κB in Pulmonary Diseases,*" Chest, Vol. 117 (2000), at pp. 1482-87, and Roshak, et al., "*Small-molecule Inhibitors of NF-κB for the Treatment of Inflammatory Joint Disease.*" Current Opinion in Pharmacol. Vol. 2 (2002) pp. 316-321.

Additionally attention has focused on inhibition of NF-κB and/or its activation pathway to provide a means for treating cancer. Genes which mediate either tumorigenesis or tumor metastasis are regulated by NF-κB. In addition NF-κB is know to be activated by carcinogens and tumor promoters. See e.g., Karin et al.; "*NF-κB in Cancer: From Innocent Bystander to Major Culprit,*" Nature Rev. Cancer., Vol. 2 (2002) at pp. 301-310; see also Bharti et al.; "*Nuclear factor-kappa B and cancer: its role in prevention and therapy*" in Biochem. Pharmocol. at pp. 883-888.

IκB is a cytoplasmic protein that controls NF-κB activity by retaining NF-κB in the cytoplasm. IκB is phosphorylated by the IκB kinase (IKK), which has two isoforms, IKK-α ("IKK-1") and IKK-β ("IKK-2"). When IKK phosphorylates IκB, NF-κB is rapidly released from the cytoplasm into the cell. Upon release into the cell, NF-κB translocates to the nucleus where it binds to the promoters of many genes and up-regulates the transcription of pro-inflammatory genes. Thus inhibitors of IKK-1 and/or IKK-2 would prevent translocation of NF-kB to the nucleus and prevent transcription of the pro-inflammatory gene products described above. For example see Burke, et al. "*BMS-345541 is a Highly Selective Inhibitor of IkB Kinase that Binds at an Allosteric Site of the Enzyme and Blocks NF-kB dependent Transcription in Mice.*" J. Biol. Chem. Vol. 278, (2003) pp. 1450-1456.

The therapeutic effects of glucocorticoids are mediated in part by their ability to inhibit NF-κB activity by two mechanisms, i.e., up-regulating IκB protein levels and inhibiting NF-κB subunits. The deleterious side effects of glucocorticoids (such as osteoporosis, hyperglycemia, fat redistribution, etc.) have been postulated to result from the interaction of glucocorticoids with the glucocorticoid receptor (GR) or the glucocorticoid response element (GRE). For example see Schacke, et al. "*Mechanisms Involved in the Side Effects of Glucocorticoids*" Pharmacol. and Therapeutics Vol 96 (2002) pp. 23-43. Thus inhibitors of IKK-1 and/or IKK-2 inhibitors should provide much of the therapeutic benefit of glucocorticoids with a greatly improved side effect profile.

As may be appreciated, those in the field of pharmaceutical research continue to seek to develop new compounds and compositions having increased effectiveness, bioavailability, and solubility, having fewer side effects, and/or providing the physician and patient with a choice of treatment options. Particularly in the area of immune response, individuals respond differently depending upon the type of treatment and chemical agent used. Mechanisms of action continue to be studied to aid in understanding the immune response and in developing compounds effective for treating inflammatory and immune-related disorders.

The present invention provides for novel tricyclic compounds useful as inhibitors of IKK.

SUMMARY OF THE INVENTION

Accordingly, the present invention provides novel inhibitors of IKK enzyme activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides for a novel process and intermediates for the preparation of the heterocyclic systems described within this document.

The present invention provides a method for treating disorders selected from rheumatoid arthritis, asthma, inflammaotry bowel disease, chronic obstructive pulmonary disease, psoriasis, and cancer, comprising administering to a host in need of such treatment a therapeutically effective amount of at least one of the compounds of the present invention or a pharmaceutically acceptable salt or prodrug form thereof.

The present invention provides a method for treating inflammatory diseases, immune diseases and cancer comprising administering to a host in need of such treatment a therapeutically effective amount of at least one of the compounds of the present invention or a pharmaceutically acceptable salt or prodrug form thereof.

The present invention provides novel compounds for use in therapy.

The present invention provides the use of novel compounds for the manufacture of a medicament for the treatment of inflammatory diseases and cancer.

These and other features of the invention, which will become apparent during the following detailed description, have been achieved by the inventors' discovery that compounds of formula (I):

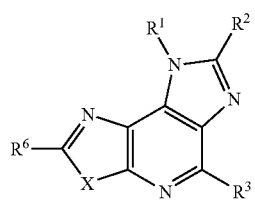

or stereoisomers or pharmaceutically acceptable salts thereof, wherein $R^1$, $R^2$, $R^3$, $R^6$, and X are defined below, are effective modulators of chemokine activity.

DETAILED DESCRIPTION OF EMBODIMENTS OF THE INVENTION

The invention is directed to compounds of formula (I), useful in treating inflammatory or immune conditions or cancer:

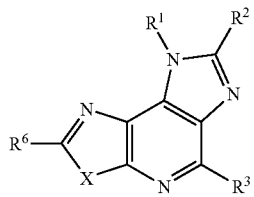

enantiomers, diastereomers, salts, and solvates thereof wherein

X is selected from O or S;

$R^1$ is selected from hydrogen, $C_{1-3}$ alkyl, $C_{2-3}$ alkenyl, and $C_{2-3}$ alkynyl;

$R^2$ is hydrogen, halo, cyano,
  (b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^a}$, $Z^{2^a}$ and $Z^{3^a}$; or
  (c) —$OR^{10^a}$, —$SR^{10^a}$, or —$SO_2R^{10^a}$;

$R^3$ is selected from
  (a) hydrogen,
  (b) alkyl, alkenyl, alkynyl, and haloalkyl, any of which may be optionally independently substituted as valence allows with one or more $Z^{1^b}$, $Z^{2^b}$ and $Z^{3^b}$;
  (c) —$OR^{11}$, —$SR^{11}$, halo;

$R^6$ is
  (a) hydrogen, hydroxy, halo, or cyano,
  (b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^a}$, $Z^{2^a}$ and $Z^{3^a}$; or
  (c) —$OR^{7a}$, —$SR^{7a}$, —$NR^{8a}R^{9a}$, —$N(R^{8a})SO_2R^{10}$, —$N(R^{8a})SO_2NR^{8b}R^{9b}$, —$N(R^{8a})SO_2R^{10}$, —$N(R^{8a})C(O)R^{7a}$, $N(R^{8a})N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —$C(O)R^{7a}$, —$C(O)OR^{7a}$, —$OC(O)R^{7a}$, —$C(O)NR^{8a}R^{9a}$, or —$OC(O)NR^{8a}R^{9a}$;

$R^{7a}$ and $R^{7b}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;

$R^{8a}$, $R^{8b}$, $R^{9a}$ and $R^{9b}$ are independently
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$; or $R^{10}$, $R^{10a}$, at each occurance, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$;

$R^{11}$, $R^{12}$, $R^{12a}$ and $R^{13}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;

$Z^{1^a 1^e}$, $Z^{2^a 2^e}$, and $Z^{3^a 3^e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O—$Y^5$,
(4) —$U^1$—S—$Y^5$,
(5) —$U^1$—C(O)$_t$—H, —$U^1$—C(O)$_t$—$Y^5$ where t is 1 or 2,
(6) —$U^1$—$SO_3$—H, or —$U^1$—S(O)$_t Y^5$,
(7) —$U^1$-halo,
(8) —$U^1$-cyano,
(9) —$U^1$-nitro,
(10) —$U^1$—$NY^2 Y^3$,
(11) —$U^1$—N($Y^4$)—C(O)—$Y^1$,
(12) —$U^1$—N($Y^4$)—C(S)—$Y^1$,
(13) —$U^1$—N($Y^4$)—C(O)—$NY^2 Y^3$,
(14) —$U^1$—N($Y^4$)—C(S)—$NY^2 Y^3$,
(15) —$U^1$—N($Y^4$)—C(O)O—$Y^5$,
(16) —$U^1$—N($Y^4$)—S(O)$_2$—$Y^1$,
(17) —$U^1$—N($Y^4$)—S(O)$_2$—$NY^2 Y^3$,
(18) —$U^1$—C(O)—$NY^2 Y^3$,
(19) —$U^1$—OC(O)—$NY^2 Y^3$,
(20) —$U^1$—S(O)$_2$—N($Y^4$)—$Y^1$,
(21) —$U^1$—N($Y^4$)—C(=$NV^{1^a}$)—$NY^2 Y^3$,
(22) —$U^1$—N($Y^4$)—C(=$NV^{1^a}$)—$Y^1$,
(23) —$U^1$—C(=$NV^{1^a}$)—$NY^2 Y^3$,
(24) oxo;
(25) —$U^1$—$Y^5$;

$V^{1^a}$ is independently hydrogen, alkyl, —CN, —C(O)$Y^1$, —S(O)$_2 Y^5$, S(O)$_2 NY^2 Y^3$;

$Y^1$, $Y^2$, $Y^3$, $Y^4$ and $Y^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $Z^6$; or
(2) $Y^2$ and $Y^3$ may together be alkylene or alkenylene, completing a 3- to 8-membered saturated or unsaturated ring together with the atoms to which they are attached, or
(4) $Y^2$ and $Y^3$ together with the nitrogen atom to which they are attached may combine to form a group —N=$CY^6 Y^7$ where $Y^6$ and $Y^7$ are each independently H or alkyl; and $Z^4$, $Z^5$, and $Z^6$ are optional substituents at each occurrence independently selected from
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

(3) —$U^1$—O—$Y^{5^a}$,
(4) —$U^1$—S—$Y^{5^a}$,
(5) —$U^1$—C(O)$_t$—H, —$U^1$—C(O)$_t$—$Y^{5^a}$ where t is 1 or 2,
(6) —$U^1$—$SO_3$—H, or —$U^1$—S(O)$_t Y^{5^a}$,
(7) —$U^1$-halo,
(8) —$U^1$-cyano,
(9) —$U^1$-nitro,
(10) —$U^1 NY^{2^a} Y^{3^a}$,
(11) —$U^1$—N($Y^{4^a}$)—C(O)—$Y^{1^a}$,
(12) —$U^1$—N($Y^{4^a}$)—C(S)—$Y^{1^a}$,
(13) —$U^1$—N($Y^{4^a}$)C(O)$NY^{2^a} Y^{3^a}$,
(14) —$U^1$—N($Y^{4^a}$)—C(S)—$NY^{2^a} Y^{3^a}$,
(15) —$U^1$—N($Y^{4^a}$)—C(O)O—$Y^{5^a}$,
(16) —$U^1$—N($Y^{4^a}$)—S(O)$_2$—$Y^{1^a}$,
(17) —$U^1$—N($Y^{4^a}$)—S(O)$_2$—$NY^{2^a} Y^{3^a}$,
(18) —$U^1$—C(O)$NY^{2^a} Y^{3^a}$,
(19) —$U^1$—OC(O)—$NY^{2^a} Y^{3^a}$,
(20) —$U^1$—S(O)$_2$—N($Y^{4^a}$)—$Y^{1^a}$,
(21) —$U^1$—N($Y^{4^a}$)—C(=$NV^{1^a}$)—$NY^{2^a} Y^{3^a}$,
(22) —$U^1$—N($Y^{4^a}$)—C(=$NV^{1^a}$)—$Y^{1^a}$,
(23) —$U^1$—C(=$NV^{1^a}$)—$NY^{2^a} Y^{3^a}$,
(24) oxo;
(25) —$U^1$—$Y^{5^a}$;

$Y^{1^a}$, $Y^{2^a}$, $Y^{3^a}$, $Y^{4^a}$ and $Y^{5^a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

$U^1$ is independently
(1) a single bond,
(2) alkylene,
(3) alkenylene, or
(4) alkynylene.

In another embodiment, the present invention is directed to compounds of formula (I), wherein X is S;

$R^1$ is selected from hydrogen, $C_{1-3}$ alkyl, $C_{2-3}$ alkenyl, and $C_{2-3}$ alkynyl;

$R^2$ is hydrogen, halo, cyano,
(b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1a}$, $Z^{2a}$ and $Z^{3a}$; or
(c) —$OR^{10a}$, —$SR^{10a}$, or —$SO_2 R^{10a}$;

$R^3$ is hydrogen;

$R^6$ is $R^6$ is

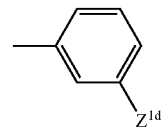

which may be further substituted with one or more $Z^{1d}$, $Z^{2d}$ and $Z^{3d}$;

$R^{10a}$, at each occurance, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$Z^{1a}$, $Z^{2a}$, $Z^{3a}$, $Z^{1d}$, $Z^{2d}$, and $Z^{3d}$ are optional substituents at each occurrence independently selected from $-W^1-V^1$; $-W^2-V^2$; $-W^3-V^3$; $-W^4-V^4$; $-W^5-V^5$;

where $W^{1-5}$ are independently
(1) a bond
(2) alkyl, (hydroxy)alkyl, (alkoxy)alkyl, alkenyl, alkynyl, haloalkyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) $-U^1-O-Y^5$,
(4) $-U^1-S-Y^5$,
(5) $-U^1-C(O)_t-H$, $-U^1(O)_t-Y^5$ where t is 1 or 2,
(6) $-U^1-SO_3-H$, or $-U^1-S(O)_tY^5$,
(7) $-U^1$-halo,
(8) $-U^1$-cyano,
(9) $-U^1$-nitro,
(10) $-U^1-NY^2Y^3$,
(11) $-U^1-N(Y^4)-C(O)-Y^1$,
(12) $-U^1-N(Y^4)-C(S)-Y^1$,
(13) $-U^1-N(Y^4)-C(O)-NY^2Y^3$,
(14) $-U^1-N(Y^4)-C(S)-NY^2Y^3$,
(15) $-U^1-N(Y^4)-C(O)O-Y^5$,
(16) $-U^1-N(Y^4)-S(O)_2-Y^1$,
(17) $-U^1-N(Y^4)-S(O)_2-NY^2Y^3$,
(18) $-U^1-C(O)-NY^2Y^3$,
(19) $-U^1-OC(O)-NY^2Y^3$
(20) $-U^1-S(O)_2-N(Y^4)-Y^1$,
(21) $-U^1-N(Y^4)-C(=NV^{1a})-NY^2Y^3$,
(22) $-U^1-N(Y^4)-C(=NV^{1a})-Y^1$,
(23) $-U^1-C(=NV^{1a})-NY^2Y^3$,
(24) oxo;
(25) $-U^1-Y^5$;

with the proviso that $Z^{1d}$ is not H;

$V^{1a}$ is independently hydrogen, alkyl, $-CN$, $-C(O)Y^1$, $-S(O)_2Y^5$, $S(O)_2NY^2Y^3$;

$Y^1$, $Y^2$, $Y^3$, $Y^4$ and $Y^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $Z^6$; or
(2) $Y^2$ and $Y^3$ may together be alkylene or alkenylene, completing a 3- to 8-membered saturated or unsaturated ring together with the atoms to which they are attached, or
(4) $Y^2$ and $Y^3$ together with the nitrogen atom to which they are attached may combine to form a group $-N=CY^6Y^7$ where $Y^6$ and $Y^7$ are each independently H or alkyl; and $Z^4$, $Z^5$, and $Z^6$ are optional substituents at each occurrence independently selected from
(1) H
(2) alkyl, (hydroxy)alkyl, haloalkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) $-U^1-O-Y^{5a}$,
(4) $-U^1-S-Y^{5a}$,
(5) $-U^1-C(O)_t-H$, $-U^1-C(O)_t-Y^{5a}$ where t is 1 or 2,
(6) $-U^1-SO_3-H$, or $-U^1-S(O)_tY^{5a}$,
(7) $-U^1$-halo,
(8) $-U^1$-cyano,
(9) $-U^1$-nitro,
(10) $-U^1-NY^{2a}Y^{3a}$,
(11) $-U^1-N(Y^{4a})-C(O)Y^{1a}$,
(12) $-U^1-N(Y^{4a})-C(S)-Y^{1a}$,
(13) $-U^1-N(Y^{4a})-C(O)-NY^{2a}Y^{3a}$,
(14) $-U^1-N(Y^{4a})-C(S)-NY^{2a}Y^{3a}$,
(15) $-U^1-N(Y^{4a})-C(O)O-Y^{5a}$,
(16) $-U^1-N(Y^{4a})-S(O)_2-Y^{1a}$,
(17) $-U^1-N(Y^{4a})-S(O)_2-NY^{2a}Y^{3a}$,
(18) $-U^1-C(O)-NY^{2a}Y^{3a}$,
(19) $-U^1-OC(O)-NY^{2a}Y^{3a}$
(20) $-U^1-S(O)_2-N(Y^{4a})-Y^{1a}$,
(21) $-U^1-N(Y^{4a})-C(=NV^{1a})-NY^{2a}Y^{3a}$,
(22) $-U^1-N(Y^{4a})-C(=NV^{1a})-Y^{1a}$,
(23) $-U^1-C(=NV^{1a})-NY^{2a}Y^{3a}$,
(24) oxo;
(25) $-U^1-Y^{5a}$;

$Y^{1a}$, $Y^{2a}$, $Y^{3a}$, $Y^{4a}$ and $Y^{5a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

$U^1$ is independently
(1) a single bond,
(2) alkylene,
(3) alkenylene, or
(4) alkynylene.

In another embodiment, the present invention is directed to compounds of formula (I), wherein
$R^3$ is
(a) hydrogen,
(b) alkyl, optionally independently substituted as valence allows with one or more $Z^{1b}$, $Z^{2b}$ and $Z^{3b}$; or
(c) $-OR^{11}$;

In another embodiment, the present invention is directed to compounds of formula (I), wherein
$R^6$ is
(a) hydrogen, alkyl, alkenyl, alkynyl, aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more $Z^{1d}$, $Z^{2d}$ and $Z^{3d}$; or
(b) $-OR^{7a}$, $-SR^{7a}$, $NR^{8a}R^{9a}$, $N(R^{8a})SO_2R^{10}$, $-N(R^{8a})SO_2NR^{8b}R^{9b}$, $-N(R^{8a})SO_2R^{10}$, $-N(R^{8a})C(O)R^{7a}$, $-N(R^{8a})N(R^{8b})C(O)R^{7a}$, $-N(R^{8a})C(O)NR^{8b}R^{9b}$, $-N(R^{8a})C(O)OR^{7a}$, $-SO_2R^{10}$, $-SO_2NR^{8b}R^{9b}$, $-C(O)R^{7a}$, $-C(O)OR^{7a}$, $-OC(O)R^{7a}$, $-C(O)NR^{8a}R^{9a}$, or $-OC(O)NR^{8a}R^{9a}$.

In another embodiment, the present invention is directed to compounds of formula (I), wherein
$R^{7a}$ is independently selected from
(a) hydrogen, or
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$.

In another embodiment, the present invention is directed to compounds of formula (I), wherein
$R^3$ is hydrogen, alkyl, which may be optionally independently substituted as valence allows with one or more $Z^{1b}$, $Z^{2b}$ and $Z^{3b}$; $-OR^{11}$; or $R^6$ is
(a) hydrogen, alkyl, aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more $Z^{1^d}$, $Z^{2^d}$ and $Z^{3^d}$; or
(b) —$OR^{7^a}$, —$SR^{7a}$, —$NR^{8^a}R^{9^a}$, —$N(R^{8^a})SO_2R^{10}$, —$N(R^{8^a})SO_2R^{10}$, —$N(R^{8^a})C(O)R^{7^a}$, —$N(R^{8^a})N(R^{8^a})C(O)R^{7^a}$, —$N(R^{8^a})C(O)NR^{8^a}R^{9^b}$, —$SO_2R^{10}$, —$C(O)R^{7^a}$, or —$C(O)NR^{8^a}R^{9^a}$.

In another embodiment, the present invention is directed to compounds of formula (I), wherein
$R^1$ is hydrogen, methyl, ethyl, propyl, i-propyl, prop-2-enyl, prop-1-enyl; and
$R^2$ is hydrogen, methyl, trifluoromethyl, and phenyl.

The invention is directed to compounds of formula (I), useful in treating inflammatory or immune conditions or cancer:

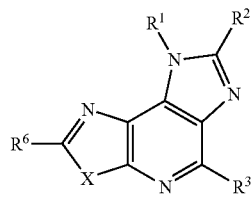

(I)

enantiomers, diastereomers, salts, and solvates thereof wherein
X is selected from O or S;
$R^1$ is selected from hydrogen and $C_{1-3}$ alkyl;
$R^2$ is (a) hydrogen, halo, cyano,
(b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^a}$, $Z^{2^a}$ and $Z^{3^a}$; or
(c) —$OR^{10^a}$, —$SR^{10^a}$, or —$SO_2R^{10^a}$;
$R^3$ is selected from
(a) hydrogen,
(b) alkyl, alkenyl, alkynyl, and haloalkyl, any of which may be optionally independently substituted as valence allows with one or more $Z^{1^b}$, $Z^{2^b}$ and $Z^{3^b}$;
(c) —$OR^{11}$, —$SR^{11}$, halo;
$R^6$ is
(a) hydrogen, hydroxy, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or
(c) —$OR^{7^a}$, —$SR^{7a}$, —$NR^{8^a}R^{9^a}$, —$N(R^{8^a})SO_2R^{10}$, —$N(R^{8^a})SO_2NR^{8^a}R^{9^b}$, —$N(R^{8^a})SO_2R^{10}$, —$N(R^{8^a})C(O)R^{7-a}$, —$N(R^{8^a})C(O)NR^{8^a}R^{9^a}$, —$N(R^{8^a})C(O)OR^{7^a}$, —$SO_2R^{10}$, —$SO_2NR^{8^a}R^{9^b}$, —$C(O)R^{7^a}$, —$C(O)OR^{7^a}$, —$OC(O)R^{7^a}$, —$C(O)NR^{8^a}R^{9^a}$, or —$OC(O)NR^{8^a}R^{9^a}$;
$R^{7^a}$ and $R^{7^b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^c}$, $Z^{2^c}$ and $Z^{3^c}$;

$R^{8^a}$ $R^{8^b}$, $R^{9^a}$ and $R^{9^b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$; or
$R^{10}$, $R^{10a}$, at each occurance, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$;
$R^{11}$, $R^{12}$, $R^{12^a}$ and $R^{13}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;
$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;
$Z^{1^{b-1^e}}$, $Z^{2^{b-2^e}}$, and $Z^{3^{b-3^e}}$ are optional substituents at each occurance independently selected from —$W^1$—$V^1$; —$W^2$—$V^2$; —$W^3$—$V^3$; —$W^4$—$V^4$; —$W^5$—$V^5$;
where $W^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or
where $V^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O—$Y^5$,
(4) —$U^1$—S—$Y^5$,
(5) —$U^1$—C(O)$_t$—H, —$U^1$—C(O)$_t$—$Y^5$ where t is 1 or 2,
(6) —$U_1$—$SO_3$—H, or —$U^1$—S(O)$_t$$Y^5$,
(7) —$U^1$-halo,
(8) —$U^1$-cyano,
(9) —$U^1$-nitro,
(10) —$U^1$—$NY^2Y^3$,
(11) —$U^1$—N($Y^4$)—C(O)—$Y^1$,
(12) —$U^1$—N($Y^4$)—C(S)—$Y^1$,
(13) —$U^1$—N($Y^4$)—C(O)—$NY^2Y^3$,
(14) —$U^1$—N($Y^4$)—C(S)—$NY^2Y^3$,
(15) —$U^1$—N($Y^4$)—C(O)O—$Y^5$,
(16) —$U^1$—N($Y^4$)—S(O)$_2$—$Y^1$,
(17) —$U^1$—N($Y^4$)—S(O)$_2$—$NY^2Y^3$,
(18) —$U^1$—C(O)—$NY^2Y^3$,
(19) —$U^1$—OC(O)—$NY^2Y^3$
(20) —$U^1$—S(O)$_2$—N($Y^4$)—$Y^1$,
(21) —$U^1$—N($Y^4$)—C(=$NV^{1^a}$)—$NY^2Y^3$,
(22) —$U^1$—N($Y^4$)—C(=$NV^{1^a}$)—$Y^1$,
(23) —$U^1$—C(=$NV^{1^a}$)—$NY^2Y^3$,
(24) oxo;
(25) —$U^1$—$Y^5$;

$V^{1a}$ is independently hydrogen, alkyl, —CN, —C(O)Y$^1$, —S(O)$_2$Y$^5$, S(O)$_2$NY$^2$Y$^3$;

Y$^1$, Y$^2$, Y$^3$, Y$^4$ and Y$^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl; or
(2) Y$^2$ and Y$^3$ may together be alkylene or alkenylene, completing a 3- to 8-membered saturated or unsaturated ring together with the atoms to which they are attached, or
(4) Y$^2$ and Y$^3$ together with the nitrogen atom to which they are attached may combine to form a group —N=CY$^6$Y$^7$ where Y$^6$ and Y$^7$ are each independently H or alkyl; and U$^1$ is independently
(1) a single bond,
(2) alkylene,
(3) alkenylene, or
(4) alkynylene.

In another embodiment, the present invention is directed to compounds of formula (I) wherein
R$^1$ is selected from hydrogen and C$_{1-3}$ alkyl;
Z$^{1a}$, Z$^{2a}$, Z$^{3a}$, Z$^{1d}$, Z$^{2d}$, and Z$^{3d}$ are optional substituents at each occurrence independently selected from —W$^1$—V$^1$; —W$^2$—V$^2$; —W$^3$—V$^3$; —W$^4$—V$^4$; —W$^5$—V$^5$;
where W$^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or
where V$^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —U$^1$—O—Y$^5$,
(4) —U$^1$—S—Y$^5$,
(5) —U$^1$—C(O)$_t$—H, —U$^1$—C(O)$_t$—Y$^5$ where t is 1 or 2,
(6) —U$^1$—SO$_3$—H, or —U$^1$—S(O)$_t$Y$^5$,
(7) —U$^1$-halo,
(8) —U$^1$-cyano,
(9) —U$^1$-nitro,
(10) —U$^1$—NY$^2$Y$^3$,
(11) —U$^1$—N(Y$^4$)—C(O)—Y$^1$,
(12) —U$^1$—N(Y$^4$)—C(S)—Y$^1$,
(13) —U$^1$—N(Y$^4$)—C(O)—NY$^2$Y$^3$,
(14) —U$^1$—N(Y$^4$)—C(S)—NY$^2$Y$^3$,
(15) —U$^1$—N(Y$^4$)—C(O)O—Y$^5$,
(16) —U$^1$—N(Y$^4$)—S(O)$_2$—Y$^1$,
(17) —U$^1$—N(Y$^4$)—S(O)$_2$—NY$^2$Y$^3$,
(18) —U$^1$—C(O)—NY$^2$Y$^3$,
(19) —U$^1$—OC(O)—NY$^2$Y$^3$
(20) —U$^1$—S(O)$_2$—N(Y$^4$)—Y$^1$,
(21) —U$^1$—N(Y$^4$)—C(=NV$^{1a}$)—NY$^2$Y$^3$,
(22) —U$^1$—N(Y$^4$)—C(=NV$^{1a}$)—Y$^1$,
(23) —U$^1$—C(=NV$^{1a}$)—NY$^2$Y$^3$,
(24) oxo;
(25) —U$^1$—Y$^5$;
with the proviso that Z$^{1d}$ is not H;

V$^{1a}$ is independently hydrogen, alkyl, —CN, —C(O)Y$^1$, —S(O)$_2$Y$^5$, S(O)$_2$NY$^2$Y$^3$;

Y$^1$, Y$^2$, Y$^3$, Y$^4$ and Y$^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more Z$^4$, Z$^5$ and Z$^6$; or
(2) Y$^2$ and Y$^3$ may together be alkylene or alkenylene, completing a 3- to 8-membered saturated or unsaturated ring together with the atoms to which they are attached, or
(4) Y$^2$ and Y$^3$ together with the nitrogen atom to which they are attached may combine to form a group —N=CY$^6$Y$^7$ where Y$^6$ and Y$^7$ are each independently H or alkyl.

In another embodiment, the present invention is directed to compounds of formula (I) wherein
Z$^{1d}$, Z$^{2d}$ and Z$^{3d}$ are optional substituents independently selected from
(a) cyano, halo, —OH, —OY$^5$, —U$^1$—NY$^2$Y$^3$, —C(O)$_t$H, —C(O)$_t$Y$^5$, —S(O)$_t$Y$^5$;
(b) alkyl or alkoxy optionally substituted with one or more cyano, halo, —OH, —OY$^5$, —U$^1$—NY$^2$Y$^3$, —N(Y$^4$)—C(O)—Y$^1$, —N(Y$^4$)—C(O)—NY$^2$Y$^3$, —C(O)—NY$^2$Y$^3$, —C(O)$_t$H, —C(O)$_t$Y$^5$, —S(O)$_t$Y$^5$, —U$^1$-heteroaryl.

In another embodiment, the present invention is directed to compounds of formula (I) wherein
Z$^{1d}$, Z$^{2d}$ and Z$^{3d}$ are optional substituents independently selected from
(a) cyano, halo, —OH, —OY$^5$, —C(O)$_t$H, —C(O)$_t$Y$^5$, —S(O)$_t$Y$^5$, or
(b) alkyl or alkoxy optionally substituted with one or more cyano, halo, —OH, —OY$^5$, —U$^1$—NY$^2$Y$^3$, —N(Y$^4$)—C(O)—NY$^2$Y$^3$, —C(O)—NY$^2$Y$^3$, —C(O)$_t$H, —C(O)$_t$Y, —S(O)$_t$Y, or —U$^1$—N(Y$^4$)—C(O)—Y$^1$,
where
U$^1$ is a bond or alkylene.

In another embodiment, the present invention is directed to compounds of formula (I) wherein
R$^3$ is selected from
(a) hydrogen,
(b) alkyl which may be optionally independently substituted as valence allows with one or more Z$^{1b}$, Z$^{2b}$ and Z$^{3b}$; or
(c) —OR$^{11}$ or halo;

In another embodiment, the present invention is directed to compounds of formula (I) wherein
R$^6$ is
(a) alkyl, alkenyl, alkynyl, aryl, heteroaryl, (cycloalkyl)alkyl, (heterocyclo)alkyl, (aryl)alkyl, or (heteroaryl)alkyl any of which may be optionally independently substituted as valence allows with one or more Z$^{1d}$, Z$^{2d}$ and Z$^{3d}$; or
(b) —OR$^{7a}$, —SR$^{7a}$, —NR$^{8a}$R$^{9a}$, —N(R$^{8a}$)SO$_2$R$^{10}$, —N(R$^{8a}$)SO$_2$NR$^{8b}$R$^{9b}$, —N(R$^{8a}$)SO$_2$R$^{10}$, —N(R$^{8a}$)C(O)R$^{7a}$, —N(R$^{8a}$)C(O)NR$^{8b}$R$^{9b}$, —N(R$^{8a}$)C(O)OR$^{7a}$, —SO$_2$R$^{10}$, —SO$_2$NR$^{8b}$R$^{9b}$, —C(O)R$^{7a}$, —C(O)OR$^{7a}$, —OC(O)R$^{7a}$, —C(O)NR$^{8a}$R$^{9a}$, or —OC(O)NR$^{8a}$R$^{9a}$.

In another embodiment, the present invention is directed to compounds of formula (I) wherein
R$^{7a}$ is independently selected from
(a) hydrogen, or
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1c}$, Z$^{2c}$ and Z$^{3c}$.

In another embodiment, the present invention is directed to compounds of formula (I) wherein $Z^{1^b}$, $Z^{2^b}$ and $Z^{3^b}$ are optional substituents independently selected from alkyl, heteroaryl, —OH, —O—$Y^5$, —$U^1$—$NY^2Y^3$, —C(O)$_t$H, —C(O)$_tY^5$;

$Z^{1^c}$ is (a) —OH, —$OY^5$ or (b) aryl optionally substituted with —OH or —$OY^5$;

$Z^{1^d}$, $Z^{2^d}$ and $Z^{3^d}$ are optional substituents independently selected from (a) cyano, halo, —OH, —$OY^5$, —$U^1$—$NY^2Y^3$, —C(O)$_t$H, —C(O)$_t$Y, —S(O)$_tY^5$;

(b) alkyl or alkoxy optionally substituted with one or more cyano, halo, —OH, —OY, —$U^1$—$NY^2Y^3$, —C(O)$_t$H, —C(O)$_t$Y, —S(O)$_t$Y, —$U^1$-heteroaryl.

In another embodiment, the present invention is directed to compounds of formula (I) wherein $R^3$ is selected from (a) hydrogen, (b) alkyl which may be optionally independently substituted as valence allows with one or more $Z^{1^b}$, $Z^{2^b}$ and $Z^{3^b}$; or (c) —$OR^{11}$ or halo;

$R^6$ is (a) alkynyl optionally substituted with $Z^{1^d}$ where $Z^{1^d}$ is aryl which may be further optionally independently substituted with one or more cyano, halo, —OH, —OY, —$U^1$—$NY^2Y^3$, —C(O)$_t$H, —C(O)$_t$Y, or, —S(O)$_t$Y;

(b) aryl optionally independently substituted as valence allows with one or more $Z^{1^d}$, $Z^{2^d}$ and $Z^{3^d}$; or (c) —$OR^{7a}$, —$SR^{7a}$, —$SO_2R^{10}$, —$SO_2NR^{8b}R^{9b}$, —OC(O)$R^{7a}$, or —OC(O)$NR^{8a}R^{9a}$;

$Z^{1^b}$, $Z^{2^b}$ and $Z^{3^b}$ are optional substituents independently selected from —OH, —OY, —$U^1$—$NY^2Y^3$, —C(O)$_t$H, —C(O)$_t$Y, —$U^1$—$N(Y^4)$—C(O)—$Y^1$, or —$U^1$—$N(Y^4)$—C(O)O—$Y^5$, where $U^1$ is a bond or alkylene;

$Z^{1^c}$ is (a) —OY where Y is aryl, or (b) aryl optionally substituted with —OH or —OY where Y is alkyl;

$Z^{1^d}$, $Z^{2^d}$ and $Z^{3^d}$ are optional substituents independently selected from (a) cyano, halo, —OH, —OY, —C(O)$_t$H, —C(O)$_t$Y, —S(O)$_t$Y, or (b) alkyl or alkoxy optionally substituted with one or more cyano, halo, —OH, —OY, —$U^1$—$NY^2Y^3$, —C(O)$_t$H, —C(O)$_t$Y, —S(O)$_t$Y, —$U^1$—$N(Y^4)$—C(O)—$Y^1$, —$U^1$—$N(Y^4)$—C(O)—$Y^1$, or —$U^1$—$N(Y^4)$—$S(O)_2$—$Y^1$, where $U^1$ is a bond or alkylene.

In another embodiment, the present invention is directed to compounds of formula (I) wherein $R^1$ is alkyl; and $R^2$ is hydrogen.

In another embodiment, the present invention is directed to compounds of formula (I) wherein $R^6$ is

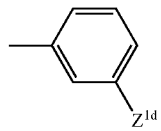

which may be further substituted with one or more $Z^{1^d}$, $Z^{2^d}$ and $Z^{3^d}$.

In another embodiment, the present invention is directed to compounds of formula (I) wherein the compound is selected from the examples.

The invention also relates to pharmaceutical compositions containing at least one compound of formula (I) and a pharmaceutically-acceptable carrier or diluent, for use in treating inflammatory and immune diseases or cancer. Also included within the invention are methods of treating such diseases comprising administering to a mammal in need of such treatment an effective amount of at least one compound of formula (I).

In another embodiment, $R^6$ is phenyl substituted with 0-3 $Z^{1^d}$, $Z^{2^d}$ and $Z^{3^d}$.

In another embodiment, $R^6$ is —$OR^{7a}$, —$SR^{7a}$, —$NR^{8a}R^{9a}$, —$N(R^{8a})SO_2R^{10}$, —$N(R^{8a})SO_2NR^{8b}R^{9b}$, —$N(R^{8a})SO_2R^{10}$, —$N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —C(O)$R^{7a}$, —C(O)$OR^{7a}$, —OC(O)$R^{7a}$, —C(O)$NR^{8a}R^{9a}$, or —OC(O)$NR^{8a}R^{9a}$.

In another embodiment, $R^1$ is hydrogen, methyl, or ethyl.

In another embodiment, $R^2$ is hydrogen.

In another embodiment, $R^1$ is selected from hydrogen, $C_{1-3}$ alkyl, and $C_{2-3}$ alkenyl; and $R^2$ is hydrogen, alkyl, haloalkyl, or aryl.

In another embodiment, $Y^5$ is H or alkyl, wherein the alkyl is selected from methyl, ethyl, propyl, i-propyl, butyl, i-butyl, t-butyl, pentyl, and hexyl;

$Y^2$ and $Y^3$ are independently selected from alkyl wherein the alkyl is selected from methyl, ethyl, propyl, i-propyl, butyl, i-butyl, t-butyl, pentyl, and hexyl.

In another embodiment, $R^6$ is (a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or (b) —$OR^{7a}$, —$SR^{7a}$, —$NR^{8a}R^{9a}$, —$N(R^{8a})C(O)R^{7a}$, —$N(R^{8a})N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —C(O)$R^{7a}$, —C(O)$OR^{7a}$, —OC(O)$R^{7a}$, —C(O)$NR^{8a}R^{9a}$, or —OC(O)$NR^{8a}R^{9a}$.

In another embodiment, $R^6$ is (a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or (b) —$OR^{7a}$, —$SR^{7a}$, —$NR^{8a}R^{9a}$, —$N(R^{8a})C(O)R^{7a}$, —$N(R^{8a})N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —C(O)$R^{7a}$, —C(O)$OR^{7a}$, —OC(O)$R^{7a}$, —C(O)$NR^{8a}R^{9a}$, or —OC(O)$NR^{8a}R^{9a}$;

wherein $Z^{1d}$, $Z^{2d}$ and $Z^{3d}$ is —$W^4$—$V^4$; where $W^4$ is
(1) a bond
(2) alkyl, (hydroxy)alkyl, alkenyl, haloalkyl, heteroaryl, or (heteroaryl)alkyl; and where $V^4$ is
(1) H
(2) aryl, (aryl)alkyl, heterocyclo, (heterocyclo)alkyl, heteroaryl, or (heteroaryl)alkyl;
(3) —$U^1$—O—$Y^5$,
(4) —$U^1$—C(O)$_t$—H, —$U^1$—C(O)$_t$—$Y^5$ where t is 1 or 2,
(5) —$U^1$—SO$_3$—H, or —$U^1$—S(O)$_t$$Y^5$,
(6) —$U^1$-halo,
(7) —$U^1$—NY$^2$Y$^3$,
(8) —$U^1$—N(Y$^4$)—C(O)—Y$^1$,
(8) —$U^1$—N(Y$^4$)—C(O)—NY$^2$Y$^3$,
(10) —$U^1$—N(Y$^4$)—C(O)O—Y$^5$,
(11) —$U^1$—N(Y$^4$)—S(O)$_2$—Y$^1$,
(12) —$U^1$—N(Y$^4$)—S(O)$_2$—NY$^2$Y$^3$,
(13) —$U^1$—C(O)—NY$^2$Y$^3$,
(14) —$U^1$—OC(O)—NY$^2$Y$^3$
(15) —$U^1$—S(O)$_2$—N(Y$^4$)—Y$^1$; and
$U^1$ is a bond.

In another embodiment, $R^6$ is
(a) alkynyl optionally substituted with $Z^{1d}$ where $Z^{1d}$ is aryl which may be further optionally independently substituted with one or more cyano, halo, —OH, —OY, —$U^1$—NY$^2$Y$^3$, —C(O)$_t$H, —C(O)$_t$Y, or, —S(O)$_t$Y;
(b) aryl optionally independently substituted as valence allows with one or more $Z^{1d}$, $Z^{2d}$ and $Z^{3d}$; or
(c) —R$^{7a}$, —SR$^{7a}$, —SO$_2$R$^{10}$, —SO$_2$NR$^{8b}$R$^{9b}$, —OC(O)R$^{7a}$, or —OC(O)NR$^{8a}$R$^{9a}$;
$Z^{1b}$, $Z^{2b}$ and $Z^{3b}$ are optional substituents independently selected from —OH, —OY, —$U^1$—NY$^2$Y$^3$, —C(O)$_t$H, —C(O)$_t$Y, —$U^1$—N(Y$^4$)—C(O)—Y$^1$, or —$U^1$—N(Y$^4$)—C(O)O—Y$^5$.

In another embodiment
$R^6$ is
(a) alkynyl optionally substituted with $Z^{1d}$ where $Z^{1d}$ is aryl which may be further optionally independently substituted with one or more cyano, halo, —OH, —OY, —$U^1$—NY$^2$Y$^3$, —C(O)$_t$H, —C(O)$_t$Y, or, —S(O)$_t$Y;
(b) aryl optionally independently substituted as valence allows with one or more $Z^{1d}$, $Z^{2d}$ and $Z^{3d}$; or
(c) —OR$^{7a}$, —SR$^{7a}$, —SO$_2$R$^{10}$, —SO$_2$NR$^{8b}$R$^{9b}$, —OC(O)R$^{7a}$, or —OC(O)NR$^{8a}$R$^{9a}$;
$Z^{1b}$, $Z^{2b}$ and $Z^{3b}$ are optional substituents independently selected from —OH, —OY, —$U^1$—NY$^2$Y$^3$, —C(O)$_t$H, —C(O)$_t$Y, —$U^1$—N(Y$^4$)—C(O)—Y$^1$, or —$U^1$—N(Y$^4$)—C(O)O—Y$^5$, where
$U^1$ is a bond or alkylene;
$Z^{1c}$ is
(a) —OY where Y is aryl, or
(b) aryl optionally substituted with —OH or —OY where Y is alkyl;
$Z^{1d}$, $Z^{2d}$ and $Z^{3d}$ are optional substituents independently selected from
(a) cyano, halo, —OH, —OY, —C(O)$_t$H, —C(O)$_t$Y, —S(O)$_t$Y, or
(b) alkyl or alkoxy optionally substituted with one or more cyano, halo, —OH, —OY, —$U^1$—NY$^2$Y$^3$, —C(O)$_t$H, —C(O)$_t$Y, —S(O)$_t$Y, —$U^1$—N(Y$^4$)—C(O)—Y$^1$, —$U^1$—N(Y$^4$)—C(O)—Y$^1$, or —$U^1$—N(Y$^4$)—S(O)$_2$—Y$^1$,
where
$U^1$ is a bond or alkylene.

In another embodiment
$R^6$ is
(a) alkynyl optionally substituted with $Z^{1d}$ where $Z^{1d}$ is phenyl which may be further optionally independently substituted with 0-1 cyano, halo, —OH, —OY, —$U^1$—NY$^2$Y$^3$, —C(O)$_t$H, —C(O)$_t$Y, or, —S(O)$_t$Y;
(b) phenyl optionally independently substituted as valence allows with one or more $Z^{1d}$, $Z^{2d}$ and $Z^{3d}$; or
(c) —OR$^{7a}$, —SR$^{7a}$;
$Z^{1b}$, $Z^{2b}$ and $Z^{3b}$ are optional substituents independently selected from —OH, —OY, —$U^1$—NY$^2$Y$^3$, —C(O)$_t$H, —C(O)$_t$Y, —$U^1$—N(Y$^4$)—C(O)—Y$^1$, or —$U^1$—N(Y$^4$)—C(O)O—Y$^5$, where
$U^1$ is a bond or alkylene, wherein alkylene is selected from methylene, ethylene, propylene, and butylene;
$Z^{1c}$ is
(a) —OY where Y is phenyl, or
(b) phenyl optionally substituted with 0-1 —OH or —OY where Y is alkyl selected from methyl, ethyl, propyl, i-propyl, butyl, i-butyl, t-butyl, pentyl, hexyl;
$Z^{1d}$, $Z^{2d}$ and $Z^{3d}$ are optional substituents independently selected from
(a) cyano, halo, —OH, —OY, —C(O)$_t$H, —C(O)$_t$Y, —S(O)$_t$Y, or
(b) alkyl or alkoxy optionally substituted with one or more cyano, halo, —OH, —OY, —$U^1$—NY$^2$Y$^3$, —C(O)$_t$H, —C(O)$_t$Y, —S(O)$_t$Y, —$U^1$—N(Y$^4$)—C(O)—Y$^1$, —$U^1$—N(Y$^4$)—C(O)—Y$^1$, or —$U^1$—N(Y$^4$)—S(O)$_2$—Y$^1$,
where
$U^1$ is a bond or alkylene, wherein alkylene is selected from methylene, ethylene, propylene, and butylene.

In another embodiment, $Y^1$, $Y^2$, $Y^3$, and $Y^4$ are independtly selected from hydrogen, alkyl, wherein alkyl is selected from alkyl is selected from methyl, ethyl, propyl, i-propyl, butyl, i-butyl, t-butyl, pentyl, and hexyl; aryl wherein aryl is phenyl, (aryl)alkyl.

In another embodiment, $Z^{1d}$ is selected from alkyl substituted with —$U^1$—NY$^2$Y$^3$, —$U^1$—N(Y$^4$)—C(O)—Y$^1$, —$U^1$—N(Y$^4$)—C(O)—NY$^2$Y$^3$, —$U^1$—N(Y$^4$)—C(O)O—Y$^5$, —$U^1$—N(Y$^4$)—C(O)O—Y$^5$, —$U^1$—N(Y$^4$)—S(O)$_2$—Y$^1$, —$U^1$—C(O)—NY$^2$Y$^3$, In another embodiment, $R^6$ is

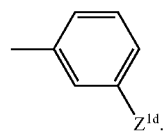

In another embodiment, the present invention is directed to a compound of Formula (I), wherein the compound is selected from the compounds of the Examples or of Tables.

In another embodiment, the present invention is directed to a pharmaceutical composition, comprising a pharmaceutically acceptable carrier and a therapeutically effective amount of a compound of Formula (I).

In another embodiment, the present invention is directed to a method of treating an inflammatory or immune disease or disorder comprising administering to a mammal in need thereof a therapeutically-effective amount of at least one compound of formula (I).

In another embodiment, the present invention is directed to a method of treating cancer comprising administering to a mammal in need thereof a therapuetically-effective amount of at least one compound of formula (I)

In another embodiment, the present invention is directed to a method of treating an inflammatory or immune disease or disorder selected from, rheumatoid arthritis, asthma, inflammatory bowel disease, chronic obstructive pulmonary disease, and psoriasis.

In another embodiment, the present invention is directed the use of a compound of Formula (I) in the preparation of a medicament for the treatment of an inflammatory or immune disease.

In another embodiment, the present invention is directed the use of a compound of Formula (I) in the preparation of a medicament for the treatment of cancer.

In another embodiment, the present invention is directed to the use of a compound of Formula (I) in the preparation of a medicament for the treatment of an inflammatory or immune disease.

In another embodiment, the present invention is directed to the use of a compound of Formula (I) in the preparation of a medicament for the treatment of cancer.

In another embodiment, the present invention is directed to the use of a compound of Formula (I) in the preparation of a medicament for the treatment of an inflammatory or immune disease, wherein the disease is selected from, rheumatoid arthritis, asthma, inflammatory bowel disease, chronic obstructive pulmonary disease, and psoriasis.

In another embodiment, the present invention is directed to the use of a compound of Formula (I) for use in therapy.

The invention may be embodied in other specific forms without departing from the spirit or essential attributes thereof. This invention also encompasses all combinations of alternative aspects and embodiments of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The following are definitions of terms used in this specification. The initial definition provided for a group or term herein applies to that group or term throughout the present specification, individually or as part of another group, unless otherwise indicated.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced. The term "optionally independently substituted as valence allows", as used herein, means that the any one or more hydrogens on the designated variable is independently replaced with a selection from the indicated group, provided that the designated variable's normal valency is not exceeded, and that the substitution results in a stable compound.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "alkyl" as used herein by itself or as part of another group refers to straight and branched chain hydrocarbons, containing 1 to 20 carbons, alternatively, 1 to 10 carbons, or 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms, are an alternative embodiment.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $—C_vF_w$ where v=1 to 3 and w=1 to (2v+1)).

The term "alkenyl" as used herein by itself or as part of another group refers to straight or branched chain radicals of 2 to 20 carbons, alternatively, 2 to 12 carbons, or 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, alternatively, 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

When the term "alkyl" is used together with another group, such as in "(aryl)alkyl", this conjunction is meant to refer to a substituted alkyl group wherein at least one of the substituents is the specifically named group in the conjunction. For example, "(aryl)alkyl" refers to a substituted alkyl group as defined above wherein at least one of the substituents is an aryl, such as benzyl.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

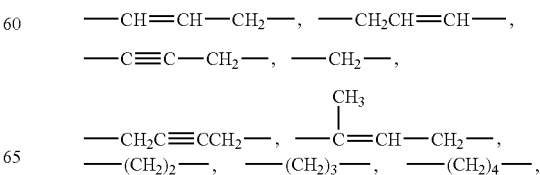

-continued

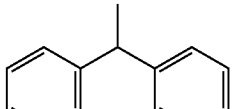

and the like. Alkylene groups may be optionally independently substituted as valence allows with one or more groups provided in the definition of $Z^1$.

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, alternatively, 3 to 7 carbons, forming the ring. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

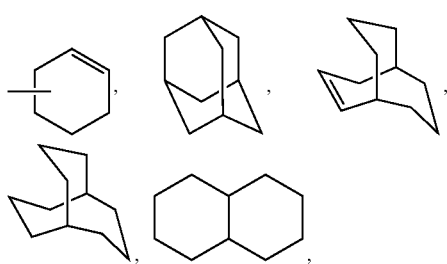

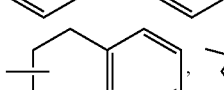

and the like.

The term "cycloalkylene" as employed herein refers to a "cycloalkyl" group which includes free bonds and thus is a linking group such as

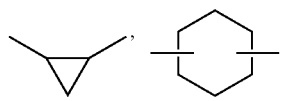

and the like.

One skilled in the field will understand that, when the designation "$CO_2$" is used herein, this is intended to refer to the group

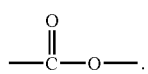

The term "alkoxy" refers to an alkyl or substituted alkyl group as defined above bonded through an oxygen atom (—O—), i.e., the groups —$OR_d$, wherein $R_d$ is alkyl or substituted alkyl.

The term "alkylthio" refers to an alkyl or substituted alkyl group as defined above bonded through a sulfur atom (—S—), i.e., the groups —$SR_d$, wherein $R_d$ is alkyl or substituted alkyl.

The term "acyl" refers to a carbonyl group linked to an organic radical, more particularly, the group C(=O)$R_g$, wherein $R_g$ can be selected from alkyl, alkenyl, substituted alkyl, or substituted alkenyl, as defined herein.

The term "alkoxycarbonyl" refers to a carboxy group

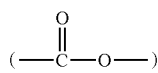

linked to an organic radical ($CO_2R_g$), wherein $R_g$ is as defined above for acyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

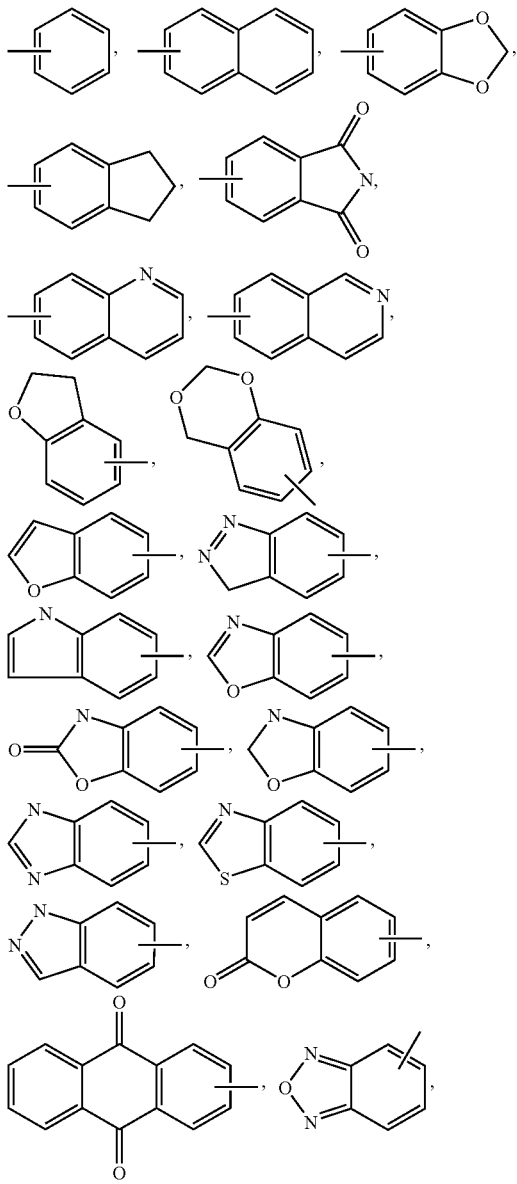

and the like.

To The term "heteroaryl" as used herein by itself or as part of another group refers to monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

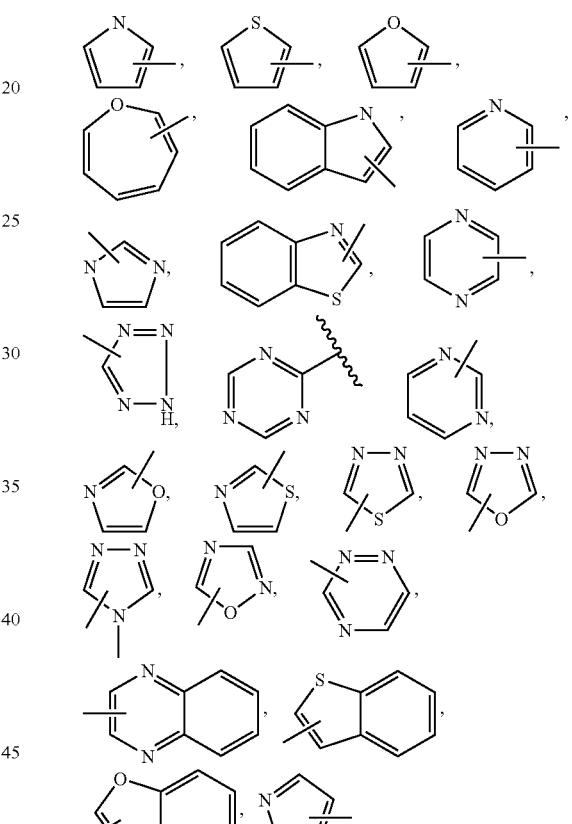

and the like.

In compounds of formula (I), heteroaryl groups include

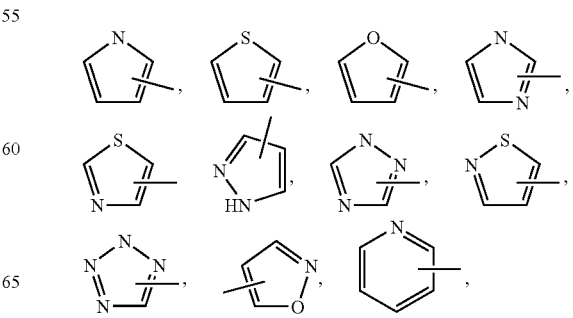

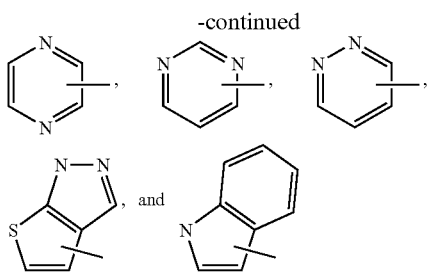

and the like, which optionally may be substituted at any available carbon or nitrogen atom.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, alternatively, containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

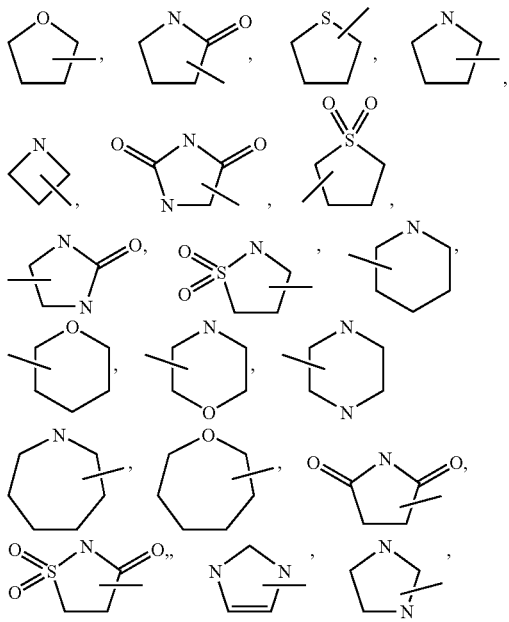

and the like.

Heterocyclo groups in compounds of formula (I) include

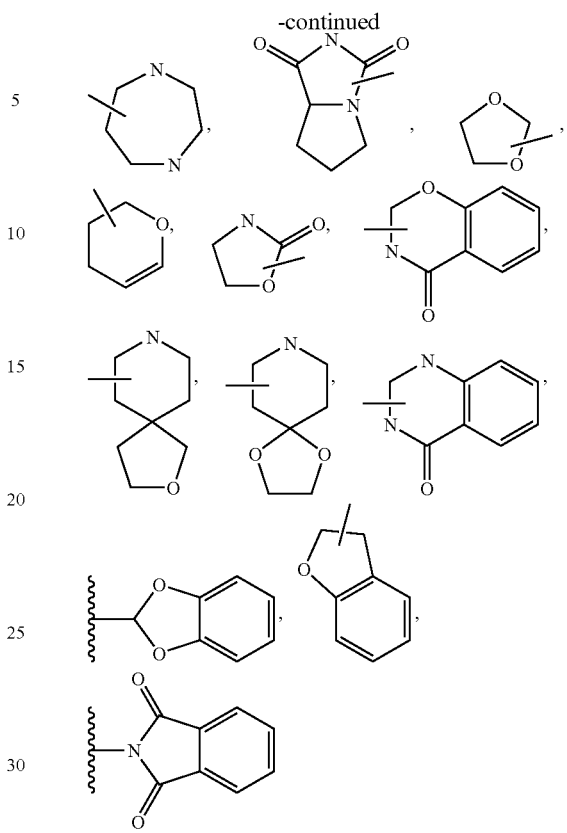

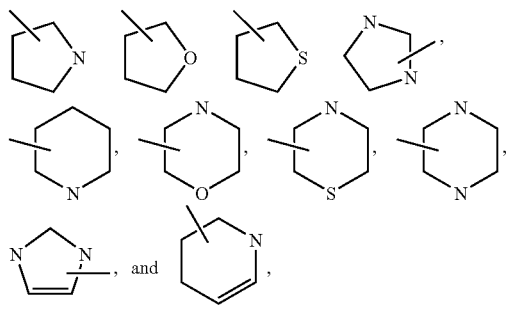

which optionally may be substituted.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl).

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, alternatively, 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts")may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, compounds of formula I may have prodrug forms. Any compound that will be converted in vivo to provide the bioactive agent (i.e., a compound of formula I) is a prodrug within the scope and spirit of the invention.

For example, pro-drug compounds of formula I may be carboxylate ester moieties. A carboxylate ester may be conveniently formed by esterifying any of the carboxylic acid functionalities found on the disclosed ring structure(s). Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull*, Vol. 32, p. 692 (1984).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit IKK or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Methods of Preparation

Compounds of Formula I may be prepared by reference to the methods illustrated in the following Schemes I through V. As shown therein the end product is a compound having the same structural formula as Formula I. It will be understood that any compound of Formula I may be produced by Scheme I-V by the suitable selection of reagents with appropriate substitution. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

The sequence described in Scheme I entails the nitration of 4-hydroxy pyridine, I-1 to provide the known compound I-2. followed by conversion to the corresponding known chloropyridine I-3. Subsequent addition of an amine such as methylamine provides the previously un-described compound I-4. Reduction of both nitro groups and simultaneous chlorination of the intermediate triaminopyridine occurs on treatment of I-4 with tin(II) chloride to produce I-5. This important intermediate can be reacted with triethyl orthoformate to provide fused imidazole I-6. Acylation either by reaction with an acid chloride or other suitable carboxylic acid activation procedure would provide I-7. Heating I-7 either in a solvent at elevated temperature, or in a microwave apparatus will produce the tricyclic system I-8 which is a compound of Formula I. I-8 can be reacted with a variety of alkoxides which are either commercially available such as sodium methoxide, or are readily prepared by reaction of an alcohol with sodium or potassium metal to produce compounds of structure I-9 which are also compounds of Formula I. Alternatively I-8 can be reacted with either alkyl or alkenyl tin reagents, or alkyl or alkenyl boronic acids or boronic esters in the presence of a suitable palladium catalyst such as dichloropalladium bis-(triphenylphoshine) complex, palladium dibenzylidineacetone complex, tetrakis-(triphenylphosphine)palladium (0), palladium acetate, or other palladium catalysts known in the art to effect such coupling reactions to produce I-10, which are also compounds of Formula I. Finally the chlorine atom present in I-8 can be removed under a variety of conditions such as hydrogenation over a suitable catalyst such as palladium on carbon, platinum oxide and the like or alternatively by trans-metalation with a suitable reagent such as tert-butyl lithium followed by quenching with a proton source to provide compounds of structure I-11 which are also compound of Formula I.

Scheme I

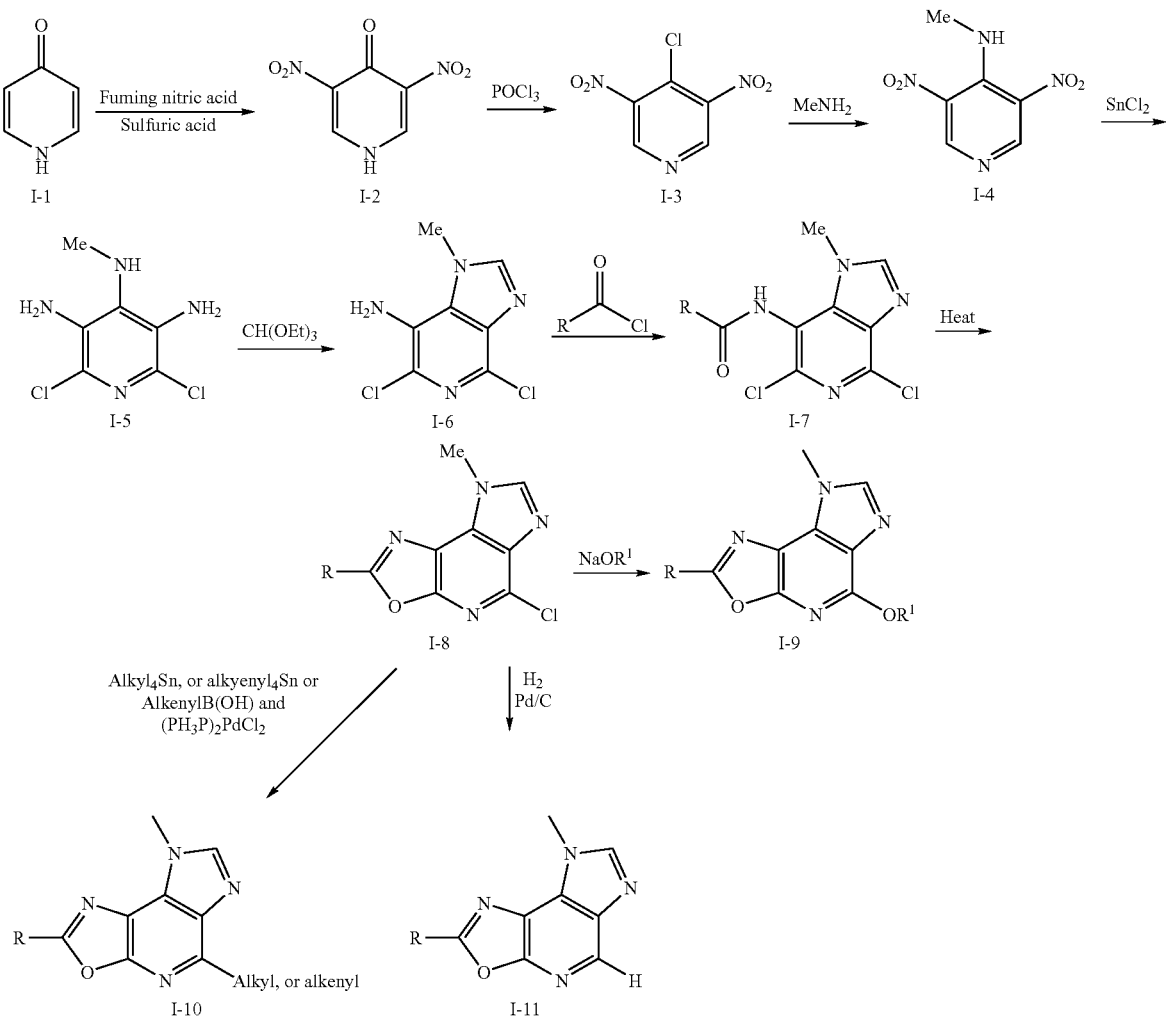

Reaction of I-7 to produce a fused thiazole system is outlined in Scheme II. Reaction of the intermediate amide I-7 with Lawesson's reagent at elevated temperature produces the thioamide which closes to produce II-1 which is also a compound of Formula I. II-1 can be reacted with a variety of alkoxides which are either commercially available such as sodium methoxide, or are readily prepared by reaction of an alcohol with sodium or potassium metal to produce compounds of structure II-2 which are also compound of Formula I. Alternatively II-1 can be reacted with either alkyl or alkenyl tin reagents, or alkyl or alkenyl boronic acids or boronic esters in the presence of a suitable palladium catalyst such as dichloropalladium bis-(triphenylphoshine) complex, palladium dibenzylidineacetone complex, tetrakis-(triphenylphosphine)palladium (0), palladium acetate, or other palladium catalysts known in the art to effect such coupling reactions to produce II-3, which are also compounds of Formula I. Finally the chlorine atom present in II-1 can be removed under a variety of conditions such as hydrogenation over a suitable catalyst such as palladium on carbon, platinum oxide and the like or alternatively by trans-metalation with a suitable reagent such as tert-butyl lithium followed by quenching with a proton source to provide compounds of structure II-4 which are also compound of Formula I.

III-4. Intermediate III-4 can be reacted with substituted aryl or heteroaryl boronic acids, or aryl or heteroaryl tin reagents to produce the desired substituted compound III-8 which is a compound of Formula I. Further elaboration of III-8 as described in Scheme II. For example reaction with alkoxides will produce compounds of structure II-2, alkyl stananes, alkenyl stananes or alkyl boronic acids/esters, or akenyl boronic acids/esters will produce compounds of structure II-3 and hydrogenation over palladium or platinum will provide compounds of structure II-4.

Scheme III

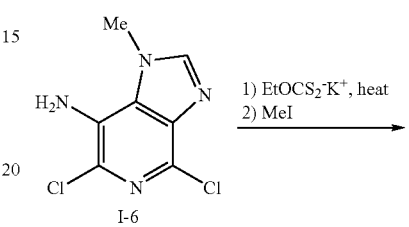

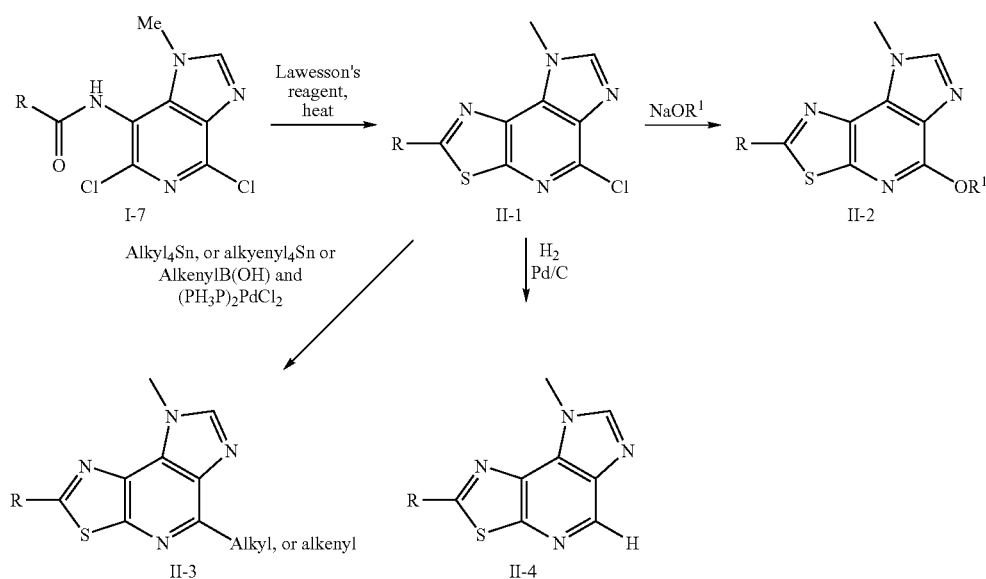

An alternate synthetic route to the thiazole systems II-1 through II-4 are depicted in scheme III. Intermediate I-6 is condensed with potassium ethyl xanthate and heated to effect ring closure to form a thiazolo thiolate anion. This is quenched with an alkyl halide like methyl iodide to produce III-1. Oxidation of the sulfur with reagents such as Oxone®, m-chloroperbenzoic acid, hydrogen peroxide and the like will produce the sulfone III-2. Displacement of the sulfone by treatment with hydrazine will produce III-3. Treatment of III-3 with copper (II) bromide produces the bromide III-4. Alternatively III-4 can be produced by the following series of reactions. I-6 can be reacted with benzoylisothiocyanate to produce III-5. Heating III-5 in the presence of a suitable base such as potassium tert-butoxide, potassium hydride, and the like, will effect cyclization to III-6. Hydrolysis of the benzoyl group with concentrated HCl will produce III-7 which can be diazotized and reacted with copper (II) bromide to produce -continued

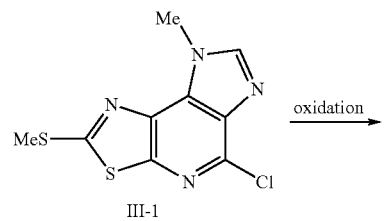

-continued

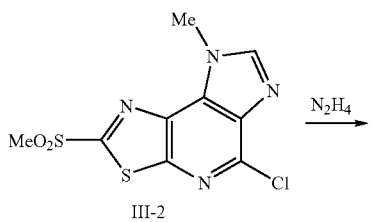
III-2

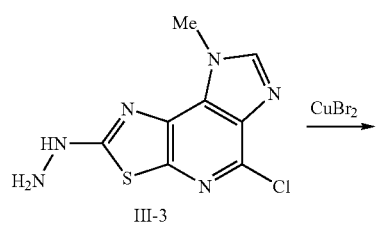
III-3

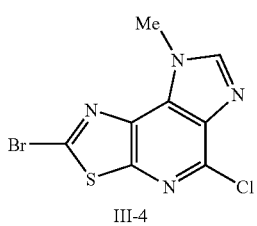
III-4

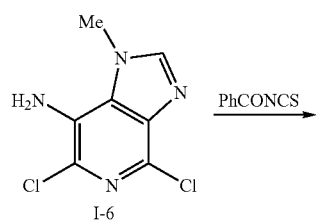
I-6

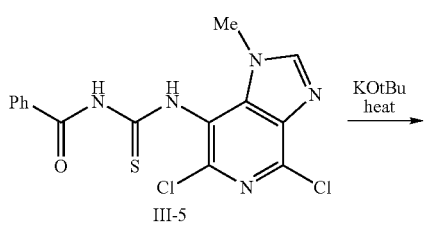
III-5

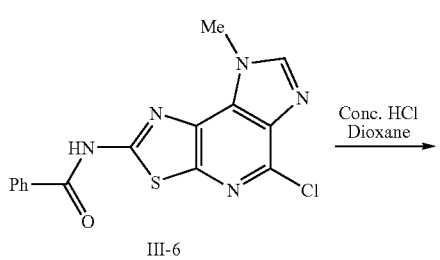
III-6

-continued

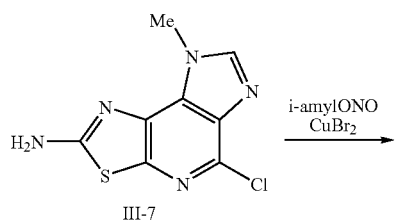
III-7

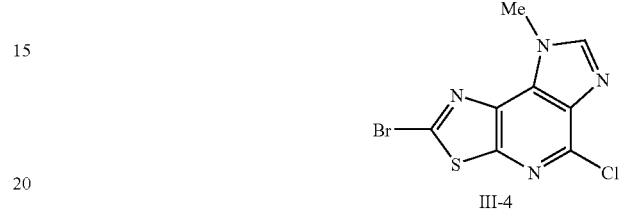
III-4

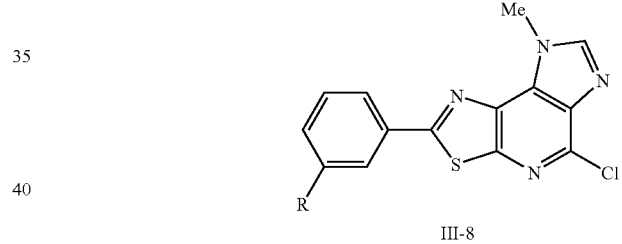
III-8

Compounds of particular interest are those where the R group depicted in Scheme I and Scheme II is a substituted aryl and heteroaryl substituents. Incorporation of substitution can be accomplished by many methods known in the art. Some examples of specific substitution is described in Scheme IV.

Compound IV-1 can be heated or heated in the presence of Lawesson's reagent to produce IV-2. Transformation to the alkoxy, alkyl, alkenyl or hydrogen substituted compounds can be accomplished as described in Scheme I-II to produce compound IV-6 which is also a compound of Formula I. Reaction of IV-6 with an acid chloride in the presence of palladium acetate will produce a ketone IV-7. Reductive amination with sodium triacetoxyborohydride will produce compounds IV-8 which is also a compound of Formula I. Alternatively IV-6 can be reacted with zinc cyanide in the presence of palladium acetate to produce nitrile IV-9. Reduction with a suitable reagent such as lithium aluminum hydride will produce IV-10. Reaction with a carboxylic acid in the presence of a suitable coupling agent such as dicyclohexylcarbodiimide (DCC) with or without the addition of HOBT will produce compounds of structure IV-11 which are also compounds of Formula I.

Scheme IV

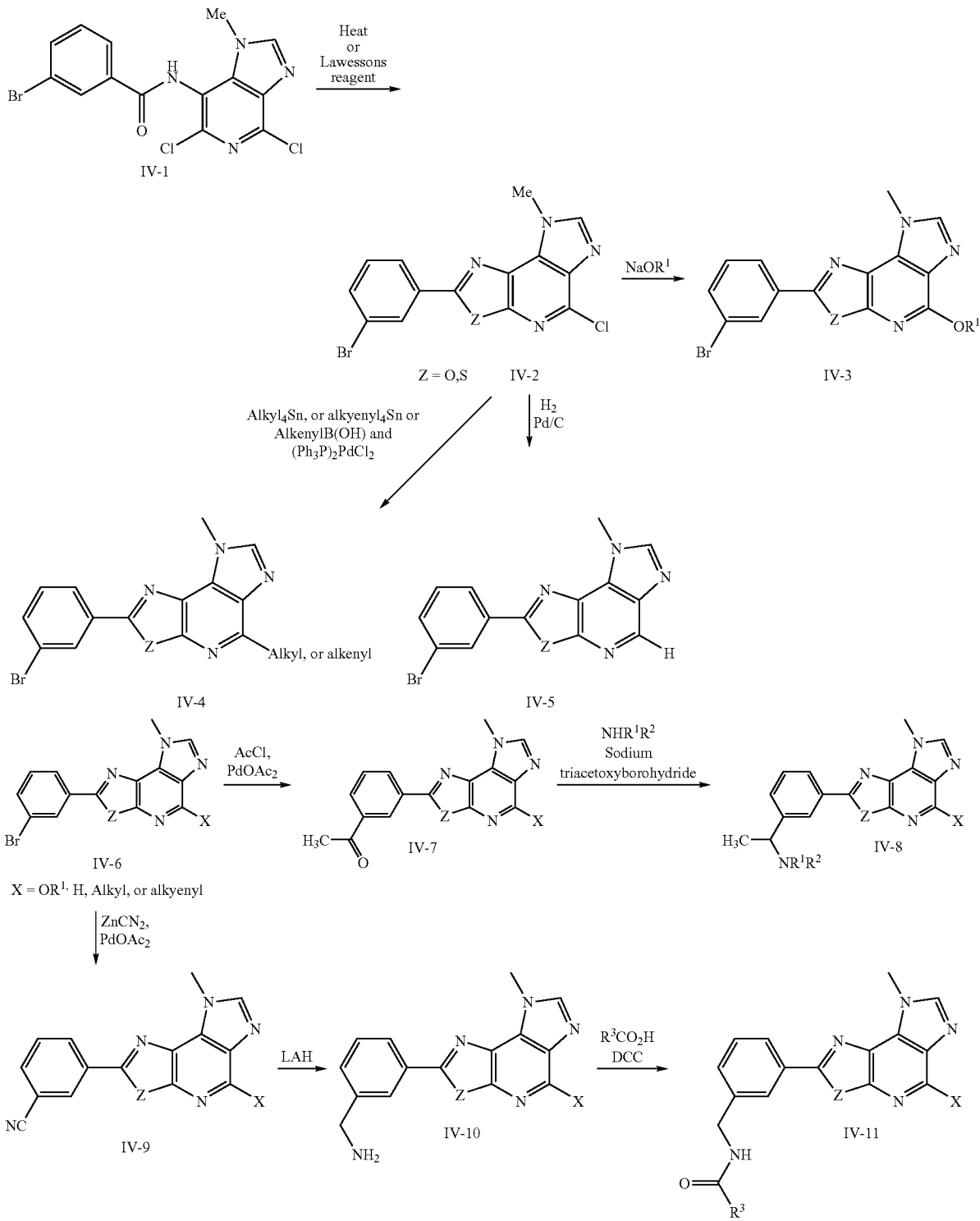

Alternatively the desired substituents can be introduced by a palladium mediated coupling protocol as described in Scheme V. Aryl halides such as aryl bromides are readily available. A search of Scifinder® reveals that there are over 500,000 known aryl bromides. Aryl halides (V-1), such as aryl bromides, aryl iodides and in some cases aryl chlorides can be converted to aryl boronic acids either by metalation with reagents such as sec-butyl lithium, tert-butyl lithium, to form lithium reagents or magnesium to form Grignard reagents and the like, followed by treatment with trimethyl borate or triisopropyl borate to produce the desired boronic acid (V-2). Alternatively in cases where functionality may be altered by or incompatible with the metalation conditions as will be apparent to one skilled in the art of organic chemistry, treatment of the aryl halide (V-1) with bis-pinacolatodiborane in the presence of a suitable catalyst such as palladium acetate can provide the desired boronic acid (V-2). Finally heteroaryl groups can be incorporated either by use of a boronic acid or more commonly as the heteroaryl stannane (V-4). The desired heteroaryl stannanes are readily prepared by reaction of the desired heteroaryl halide (V-3) with reagents such as hexamethylditin and hexabutylditin to provide the desired heteroarylstannane V-4. By way of example a boronic acid preparation sequence could begin with bromoacetophenone V-5 which on reduction with sodium borohydride will produce alcohol V-6. Treatment of the alcohol with a nitrile such as acetonitrile and the like under acidic conditions will produce the Ritter product V-7. Reaction of V-7 with bis-pinacolatodiboron in the presence of palladium acetate will produce boronic acid V-8. By way of example a heteroaryl stannane can be produced by reaction of dibromopyridine V-9 with hexabutylditin in the presence of palladium acetate will produce V-10. Further functionalization of the remaining bromine offers a significant entry into preparing compounds useful to this invention. With the appropriate aryl boronic acids or heteroaryl stannanes palladium mediated coupling with III-4 will produce the desired compounds V-11 and V-12 respectively.

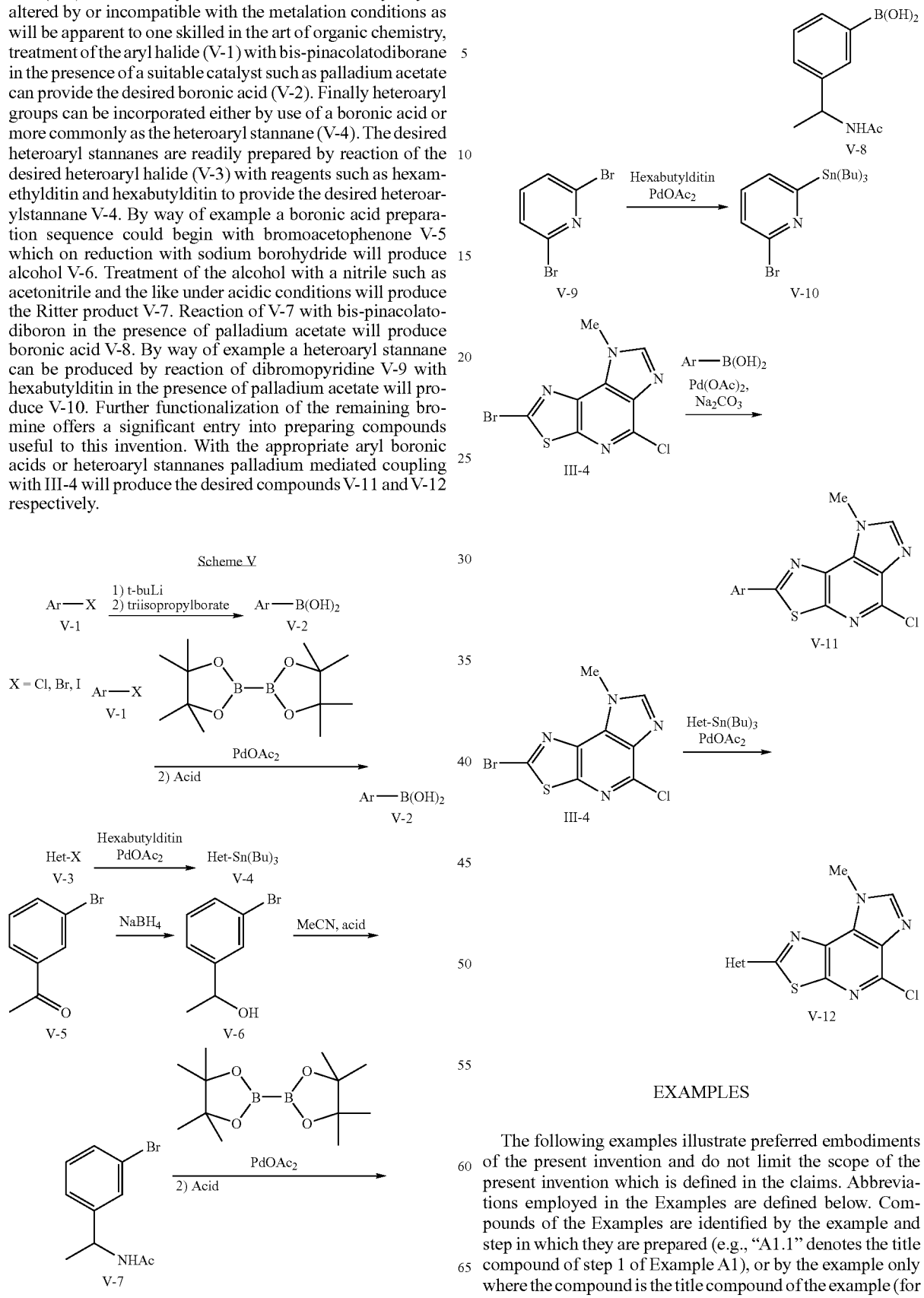

EXAMPLES

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by the example only where the compound is the title compound of the example (for example, "A2" denotes the title compound of Example A2).

| Abbreviations | |
|---|---|
| Ac | Acetyl |
| AcOH | Acetic acid |
| aq. | Aqueous |
| CDI | Carbonyldiimidazole |
| Bn | Benzyl |
| Bu | Butyl |
| Boc | tert-butoxycarbonyl |
| DMAP | Dimethylaminopyridine |
| DMA | N,N-Dimethylacetamide |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| H | Hydrogen |
| h | Hours |
| i | iso |
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| M+ | (M+H)+ |
| M+1 | (M+H)+ |
| MS | Mass spectrometry |
| n | normal |
| PhCONCS | Benzyoylisothiocyanate |
| Pd/C | Palladium on carbon |
| Ph | Phenyl |
| Pr | Propyl |
| PSI | Pounds per square inch |
| Ret Time | Retention time |
| rt or RT | Room temperature |
| sat. | Saturated |
| S-Tol-BINAP | (S)-(-)-2,2'-Bis(di-p-tolylphosphino)-1,1'-binapthyl |
| t | tert |
| TFA | Trifluoroacetic acid |
| THF | Tetrahydrofuran |
| Phenominex | Phenominex, , Macclesfield, Cheshire, UK |
| YMC | YMC, Inc, Wilmington, NC 20403 |

HPLC conditions used to determine retention times; A: 2 min gradient 0-100% B in A(A; 0.1% TFA in 90/10 water/methanol; B; 0.1% TFA in 10/90 water/methanol) using a Phenominex 4.6×30 mm S-5 ODS column at with a detection wavelength of 254 nanometers or B: 4 min gradient 0-100% B in A(A; 0.1% TFA in 90/10 water/methanol; B; 0.1% TFA in 10/90 water/methanol) using a YMC Turbopack column at with a detection wavelength of 254 nanometers or 220 nanometers.

Those experiments which specify they were performed in a microwave were conducted in a SmithSynthesizer™ manufactured by Personal Chemistry. This microwave oven generates a temperature which can be selected between 60-250° C. The microwave automatically monitors the pressure which is between 0-290 PSI. Reaction times and temperatures are reported.

Example A1

N-[(S)1-[3-[7-Chloro-8-methyl-8H-imidazo[4,5-d]thiazolo[5,4-b]pyridin-2-yl]phenyl]ethyl]amine

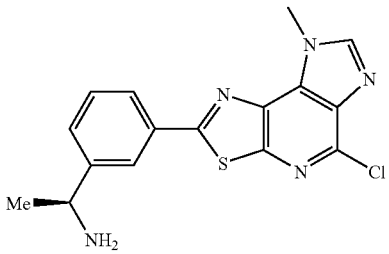

A1

A1.1: 3,5-Dinitro-1H-pyridin-4-one

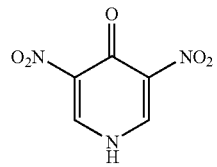

A1.1

4-Hydroxypyridine (40.0 g, 0.42 mol) was added portionwise to fuming nitric acid (140 ml) and sulfuric acid (500 ml). The resulting mixture was heated to 140° C. for 12 hours. The reaction mixture was cooled in an ice-bath and cautiously poured onto ice (500 ml). The yellow solid which precipitated was collected by filtration and dried under vacuum to yield A1.1 (70.0 g, 90%). $^1$H-NMR (DMSO-$d_6$) δ: 4.06 (2H, s). HPLC: 98.9%, ret. time=0.173 min., LC/MS (M–H)$^+$=184.

A1.2: (3,5-Dinitro-pyridin-4-yl)methylamine

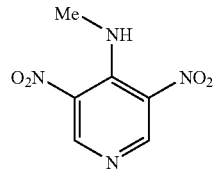

A1.2

A1.1 (10.0 g, 0.051 mol) was added portionwise to a mixture of phosphorus oxychloride (25 ml) and PCl$_5$ (17.0 g, 0.082 mol). The reaction mixture was heated to reflux under a nitrogen atmosphere for 12 hours. The reaction mixture was allowed to cool to room temperature and the phosphorus oxychloride removed in vacuo. The residue was suspended in dry THF (50 ml) and cooled to 0° C. Methylamine (32 ml, 2.0M in THF, 0.064 mol) was added dropwise over 20 minutes under a nitrogen atmosphere and the resulting solution was allowed to warm to room temperature over 1 hour. The reaction mixture was evaporated in vacuo and the residue suspended in ethyl acetate (200 ml) which was then filtered and the filtrate evaporated in vacuo to leave the crude product. The crude product was recrystallised from methanol (100 ml) to give A1.2 as a tan solid (7.2 g, 71% for two steps). HPLC: 98%, ret. time=1.58 min., LC/MS (M+H)$^+$=199.

A1.3: 2,6-Dichloro-N'-methyl-pyridine-3,4,5-triamine

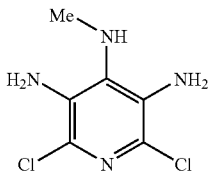

A1.3

A solution of A1.2 (60.0 g, 0.30 mol) in concentrated hydrochloric acid (300 ml) was heated to 90° C. Tin (II) chloride (85.0 g, 0.45 mol) was added portionwise over 1 hour with vigorous effervesence noted for the first equivalent of tin chloride added. The reaction mixture was heated for a further hour before the addition of more tin chloride (28.0 g, 0.15 mol) and continued heating for 2 more hours. The reaction mixture was cooled to 0° C. and cautiously basified with concentrated ammonium hydroxide (200 ml). The precipitated solid was filtered off and the filtrate extracted with ethyl acetate (5×200 ml). The combined organics were dried (MgSO4) and evaporated in vacuo to leave A1.3 as a brown solid (28.0 g, 46%). HPLC: 98%, ret. time=1.58 min., LC/MS (M+H)$^+$=208.

A1.4: 7-Amino-4,6-dichloro-1-methyl-1H-imidazo[4.5-c]pyridine

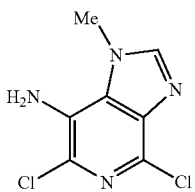

A1.4

Triethylorthoformate (25.0 ml, 0.15 mol) was added in one portion to a suspension of A1.3 (28 g, 0.14 mol) in dry acetonitrile (400 ml). The reaction mixture was heated to reflux for 4 hours and then cooled to room temperature. The reaction mixture was evaporated in vacuo to leave A1.4 as a brown powder. $^1$H-NMR (DMSO-d$_6$) δ: 8.20 (1H, s), 5.49 (2H, br. s), 4.07 (3H, s). HPLC: 98%, ret. time=0.78 min., LC/MS (M+H)$^+$=218.

A1.5: N,8-dimethyl-2-(methylthio)-5-chloro-8H-imidazo[4,5-d]thiazolo[5,4-b]pyridine

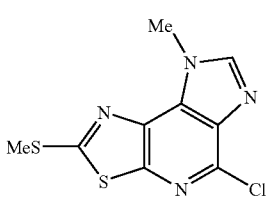

A1.5

A1.4 (2.17 g, 10 mmol) and potassium thioxanthate (3.05 g, 20 mmol) were added to 20 mL of DMF and heated for 2.5 h at 145° C. The reaction mixture was cooled to room temperature then placed in an ice bath and cooled to ~0° C. Methyl iodide (1.24 ml, 20 mmol) was added and the reaction mixture stirred for 1 hour in the ice bath. Volatile liquids were removed at ~45° C. under high vacuum. The residue was partitioned between chloroform (150 mL) and sat. sodium bicarbonate (100 mL). The aqueous layer was washed with additional chloroform (2×75 mL). The combined organic layers were dried over magnesium sulfate, filtered, and evaporated to provide a cream colored solid. The crude product was triturated with hot ethyl acetate (~75 mL) which was allowed to cool to room temperature, and the product collected by filtration. 1.49 g (55%) of A1.5 was isolated as a cream colored solid, which was >95% pure by LCMS ((M+H)$^+$=271.16, 273.17).

A1.6 7-Chloro-2-(methylsulfonyl)-4-methyl-4H-imidazo[4,5-d]thiazolo[4,5-b]pyridine

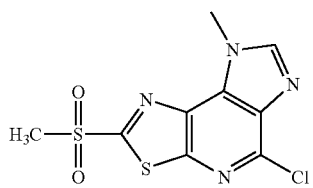

A1.6

To a mechanically stirred solution of A1.5 (12.00 g, 44.32 mmol) in MeOH (150 mL) and H$_2$O (150 mL) was added Oxone (160.9 g, 0.262 mol). This suspension was stirred for 48 h, at which time the stirring was stopped, the reaction was partially concentrated, diluted with H$_2$O, brought to pH~7 with 5N NaOH and the resulting solid collected by filtration, washed with H$_2$O and dried under vacuum overnight. A1.6 was obtained (11.30 g, 84%) as a cream solid: MS (ES): m/z 303 [$^{35}$Cl M+H]$^+$ (HPLC 99%).

A1.7 1-(7-chloro-4-methyl-4H-imidazo[4,5-d]thiazolo[4,5-b]pyridin-2-yl)hydrazine

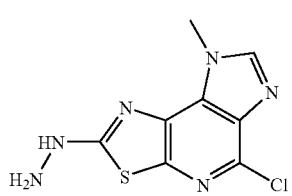

A1.7

To a stirred suspension of A1.7 (11.22 g, 37.06 mmol) in EtOH (150 mL) was added hydrazine hydrate (30 mL). This suspension was stirred overnight, at which time the stirring was stopped and the solid collected by filtration, washed with EtOH and dried under vacuum overnight to afford 9.26 g (98%) A1.7 as a cream solid: MS (ES): m/z 255 [$^{35}$Cl M+H]$^+$ (HPLC 95%).

A1.8 2-Bromo-7-chloro-4-methyl-4H-imidazo[4,5-d]thiazolo[4,5-b]pyridine

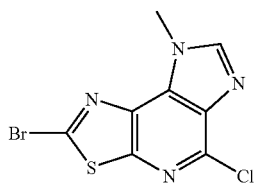

A1.8

To a stirred solution of CuBr$_2$ (24.50 g, 0.1097 mol) in AcOH (120 mL) and H$_2$O (20 mL) was added portionwise over 10 min A1.7 79.26 g, 36.36 mmol) and stirred for 4 h. The reaction was diluted with H$_2$O (700 mL) and the solid collected by filtration, washed sequentially with H$_2$O, conc. NH$_4$OH (2×) until very little blue copper complex eluted and H$_2$O, then dried. Obtained 8.69 g (79%) A1.8 as a tan solid: MS (ES): m/z 303 [$^{35}$Cl$^{79}$Br M+H]$^+$ (HPLC 95%).

Alternate Synthesis of A1.8

A1.9 1-Benzoyl-3-(4,6-dichloro-1-methyl-1H-imidazo[4,5-c]pyridin-7-yl)thiourea

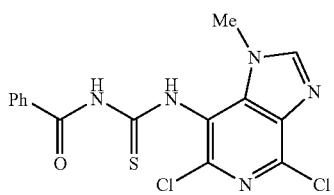

A1.9

A1.4 (6.94 g, 31 mmol) was suspended in acetone (120 mL). Benzoyl isothiocyanate (5.8 g, 35 mmol) was added dropwise over ten minutes. The reaction mixture was stirred at room temperature overnight. The next day the reaction mixture was heated to reflux for 1 h, then cooled to room temperature and the solvent removed under reduced pressure. Ethyl alcohol (50 mL) was added to the solid and the mixture heated to reflux for 1 h, then cooled to room temperature and allowed to stand for several hours. The product was collected by filtration and dried under vacuum to yield 11.32 g (93%) of A1.9 as a white powder. M+H+=380.14. 382.12, $^1$H NMR DMSO δ 12.18 s, 1H, 12.10, s, 1H, 8.48, s, 1H, 8.06 d, 2H, 7.70, t, 1H, 7.59-7.55, m, 2H.

A1.10: 2-(Phenylcarbonylamino)-7-chloro-4-methyl-4H-imidazo[4,5-d]thiazolo[4,5-b]pyridine

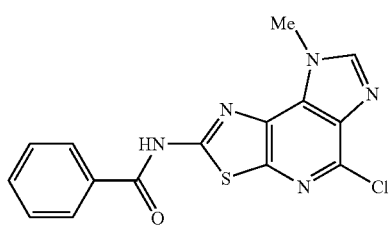

A1.10

Potassium tert-butoxide 1M solution in THF (24 mL, 24 mmol) was evaporated to dryness under reduced pressure and the residue dissolved in N-methylpyrrolidone (NMP, 15 mL).

A1.9 (3.04 g, 8 mmol) was dissolved in NMP (15 mL) and added dropwise to the solution of potassium butoxide during which time the reaction became warm to the touch. The reaction mixture was placed into a preheated oil bath (120° C.) and stirred for 1.5 h. TLC of the reaction mixture showed that no starting material remained. The reaction mixture was allowed to cool to room temperature and poured into 150 mL of ice/1N ammonium chloride solution. The produce was collected by filtration and dried in a vacuum oven at 60° C. overnight to yield 2.55 g (93%) of an off-white solid. LCMS (M+H)$^+$=344.18, 346.15; $^1$H NMR DMSO δ 13.17 s, 1H, 8.49, s, 1H, 8.17, d J=7.3 Hz, 2H, 7.70, m, 1H, 7.60 t, J=7.6 Hz, 2H, 4.26, s, 3H.

A1.11 2-Amino-7-chloro-4-methyl-4H-imidazo[4,5-d]thiazolo[4,5-b]pyridine

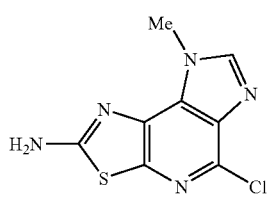

A1.11

A1.10 (3.44 g, 10 mmol) was suspended in a mixture of concentrated HCl (50 mL), anhydrous ethanol (25 mL) and anhydrous dioxane (25 mL) and heated in an oil bath maintained at 100° C. overnight during which time the solid material dissolved. The reaction mixture was cooled to room temperature and the solvent removed under reduced pressure to produce a solid. The material was suspended in water (~50 mL) and poured onto ice (50 g) and the pH adjusted to ~9 (as determined by pH paper) with 1N NaOH. After the ice melted the solid was collected by filtration and suspended in acetonitrile (25 mL) and brought to reflux for a brief period of time. The solution was allowed to cool to room temperature and stand for several hours. The product was collected by filtration and dried to yield 2.14 g (89%) of an off white powder. LCMS (M+H)$^+$=240.07 (100%), 242.04 (40%); $^1$H NMR DMSO δ 8.32, s, 1H, 7.93, s, 2H, 4.05 s, 3H.

Step A1.12 synthesis of A1.8: 2-Bromo-7-chloro-4-methyl-4H-imidazo[4,5-d]thiazolo[4,5-b]pyridine

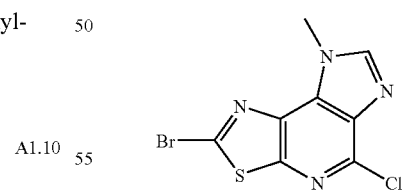

A1.8

Aminothiazole A1.11 (21.8 g, 88 mmol) and copper (II) bromide (19.67 g, 88 mmol) were dissolved in acetonitrile (600 mL) and heated in an oil bath maintained at 70° C. Isoamyl nitrite (20.5 g, 174 mmol) was added dropwise over 0.5 h and the reaction mixture maintained at 70° C. overnight. LCMS analysis showed approximately 80% conversion to the desired product. Additional copper (II) bromide (5 g, 22 mmol) and isoamyl nitrite (4.4 g, 37 mmol) were added and the reaction mixture maintained at 70° C. overnight. LCMS analysis showed no change in product formation. The reaction mixture was cooled to room temperature and filtered to provide 25 g of crude product. The material was suspended in chloroform (1 L) and washed with 1:1 saturated ammonium chloride/ammonium hydroxide (4×500 mL). The organic layer was dried over magnesium sulfate, filtered and the solvent removed under reduced pressure to yield 13.0 g of A1.8 as a pink-orange solid. LCMS: m/z 302.96 (70%), 304.97 (100%), 306.95 (30%) Elem. Anal. Theoretical %/observed %, C: 31.65/32.20; H: 1.32/1.38; N: 18.45/18.57; S, 10.56/9.82; Br: 26.32/22.33; Cl: 11.67/12.60; Cu<0.01%.

A1.13 (R,S)-tert-butyl 1-(3-(4,4,5,5-tetramethyl-1,3,2-dioxaborolan-2-yl)phenyl)ethylcarbamate

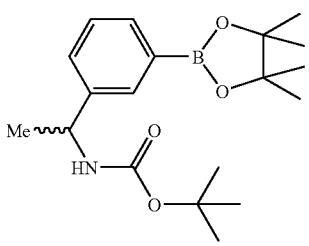

Step-A1.13a: 1-(3-Bromophenyl)ethanamine

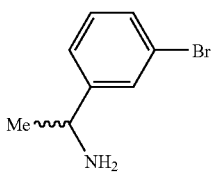

A mixture of commercially available 3-bromoacetophenone (30 g, 0.1508 mol), formic acid (47 ml) and formamide (70 ml) was heated to 220° C. for 5 h. The brown liquid obtained was cooled to RT, quenched with water and extracted with ethyl acetate. The organic layer was washed with water, brine and concentrated to provide a brown liquid. Ethanol (375 ml) and conc.HCl (75 ml) were added to the brown liquid and the reaction mixture refluxed over night. Ethanol was removed completely under reduced pressure and the aqueous layer was washed with ether and ethyl acetate to remove all non-basic impurities. The aqueous layer was basified with 10% sodium hydroxide solution and extracted with ethyl acetate. The ethyl acetate layer was washed with brine, and concentrated to provide 26 g (86.65%) of A1.13a This compound was taken to the next step with out further purification. $^1$H NMR (CDCl$_3$, 300 MHz) δ 1.38 (d, 3H), 4.1 (q, 1H), 7.2 (m, 1H), 7.27 (m, 1H), 7.37 (m, 1H), 7.51 (s, 1H). LS-MS (M−H)$^+$=200.

Step-A1.13b: tert-Butyl 1-(3-bromophenyl)ethylcarbamate

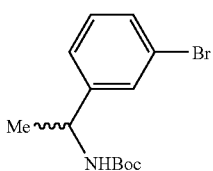

To a solution of A1.13a (15 g, 0.075 mol) in chloroform (150 ml) was added ditertbutyldicarbonate (18 g, 0.0825 mol) slowly at 0° C. and stirred at RT for over night. The solvent was removed under vacuum and the compound was purified by silica gel column chromatography using 5% of ethyl acetate in pet ether as eluent to provide 20.6 g (94%) of A1.13b as white solid. $^1$H NMR (CDCl$_3$, 400 MHz) δ 1.4 (m, 12H), 4.8 (bs, 1H), 7.21 (m, 2H), 7.4 (m, 1H), 7.45 (s, 1H). LS-MS (M−H−Boc+CH$_3$CN)$^+$=244.

Step-A1.13c: R,S)-tert-butyl 1-(3-(4,4,5,5-tetramethyl-1,3,2-dioxaborolan-2-yl)phenyl)ethylcarbamate (product A1.13)

To a solution of A1.13b (15 g, 0.05 mol) in dry dioxane (120 ml) was added potassium acetate (14.7 g, 0.15 mol), PdCl$_2$(dppf) (3 g, 0.004 mol), dppf (2.22 g, 0.004 mol), and bispinacolatodiboron (15 g, 0.06 mol). The reaction mixture was heated at 95° C. over night. The reaction mixture was cooled to room temperature, quenched with water and extracted with ethyl acetate. The organic layer was washed with water, brine and concentrated. The product was purified by 230-400 silica gel column chromatography using 3% of ethyl acetate in petrolium ether to provide 10 g (57%) of A1.13 as a white solid. $^1$H NMR (CDCl$_3$, 300 MHz) δ 1.35 (s, 12H), 1.47 (m, 12H), 4.8 (bs, 1H), 7.36 (m, 1H), 7.71 (m, 1H). LS-MS (M−H−Boc+CH$_3$CN)$^+$=292.

A1.14 (S)-tert-Butyl 1-(3-(4,4,5,5-tetramethyl-1,3,2-dioxaborolan-2-yl)phenyl)ethylcarbamate (product A1.14a) and (R)-tert-Butyl 1-(3-(4,4,5,5-tetramethyl-1,3,2-dioxaborolan-2-yl)phenyl)ethylcarbamate (product A1.14b)

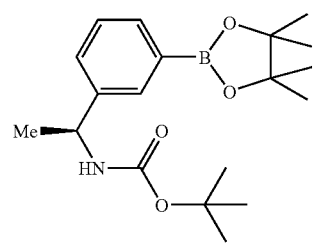

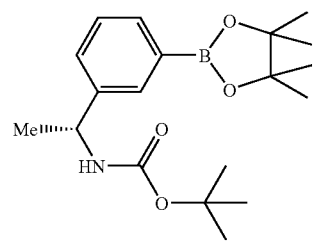

A solution A1.13 in 98% Hexanes/2% IPA (16 mg/mL) was purified by repeated injections on a chiral preparative HPLC column.

Column Conditions: Chiralpak AD (10 um 50×500 mm) Flow Rate: 60 ml/min. Isocratic: Hexane (98%), IPA (2%). Injection volume: 8.5 mL.

The mobile phase was evaporated to provide the individual enantiomers as colorless glassy solids.

Analytical Chiral HPLC: Chiralpak AD (10 um 4.6×250 mm) Flow Rate: 1 ml/min.

Isocratic: Heptane (98%), IPA (2%).

(S)-enantiomer (A1.14a) r.t.=9.51 min>99% ee (R)-enantiomer r.t. (A1.14b)=7.12 min>99% ee Step A1.15 N-[(S)1-[3-[7-Chloro-8-methyl-8H-imidazo[4.5-d]thiazolo[5,4-b]pyridin-2-yl]phenyl]ethyl]amine (product A1)

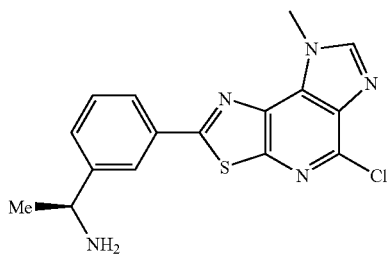

A solution of A1.8 (0.164 g, 0.54 mmol), A1.14a (0.188 g, 0.54 mmol), dichlorobis(triphenylphosphine)palladium(II) (0.0076 g, 0.011 mmol), and sodium carbonate (2N aq., 0.27 mL) in DME:Water:Ethanol (7:3:2, 6 mL) was placed in a capped C.E.M. microwave reaction tube and processed in a C.E.M. microwave reactor at 150° C. for 20 min followed by an additional processing time of 30 min at 160° C. An additional amount of A1.8 (1.00 g), A1.2 (1.14 g), dichlorobis (triphenylphosphine) palladium(II) (0.033 g), and sodium carbonate (2N aq., 1.65 mL) was divided equally among five C.E.M. microwave tubes along with DME:Water:Ethanol (7:3:2, 6 mL per tubes). Each reaction was processed for 1 h at 160° C. The reactions were combined and evaporated to dryness, then partitioned between water and chloroform. The organic layer was dried over sodium sulfate and concentrated. The residue was suspended in dioxane (50 mL) and HCl/Dioxane (4N, 10 mL) was added. The solution was stirred at room temperature for 1.5 h, concentrated to dryness, and partitioned between chloroform and saturated aq. NaHCO₃. The organic extracts were evaporated and the residue purified by flash chromatography (SiO₂, 5-20% MeOH in dichloromethane) to afford A1 (0.932 g) as a yellow solid. HPLC retention time 2.30 min. Column:Chromolith SpeedROD 4.6×50 mm (4 min grad. 0% B-100% B) Solvent A: 10% MeOH-90% H₂O 0.1% TFA Solvent B: 90% MeOH-10% H₂O-0.1% TFA. MS (ES): m/z 344.2, 346.2 [M+H]⁺

Example A2

N-[(S)1-[3-[7-Chloro-8-methyl-8H-imidazo[4,5-d]thiazolo[5,4-b]pyridin-2-yl]phenyl]ethyl]acetamide

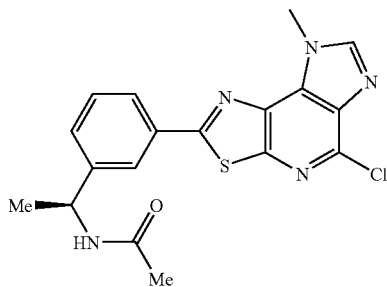

To a solution of A1 (0.30 g, 0.872 mmol) and pyridine (10 mL) in THF (15 mL) was added acetic anhydride (2 mL) dropwise. The solution was stirred at room temperature for 2-3 hours, then quenched by the addition of water (10 mL) and aq. Sodium Carbonate (2N, 1 mL). After stirring at room temperature for an additional hour, the solvents were partially evaporated and the residue partitioned between chloroform and water. The organic phases were washed with sat. aq. NaHCO₃, water, and brine then dried over MgSO₄ before being filtered and evaporated to afford A2 (0.305 g) as a brown solid. HPLC retention time 2.84 min. Column:Chromolith SpeedROD 4.6×50 mm (4 min grad. 0% B-100% B) Solvent A: 10% MeOH-90% H₂O 0.1% TFA Solvent B: 90% MeOH-10% H₂O-0.1% TFA. MS (ES): m/z 386.3, 388.2 [M+H]⁺

Example A3

N-[(S)1-[3-[8-methyl-8H-imidazo[4.5-d]thiazolo[5,4-b]pyridin-2-yl]phenyl]ethyl]acetamide

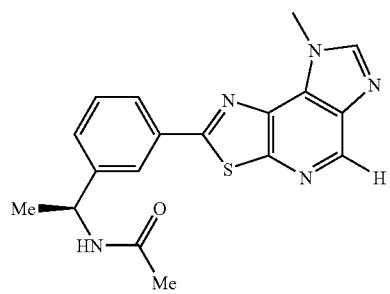

A solution of A2 (0.020 g, 0.052 mmol), Pd/C (5%, 20 mg), and ammonium formate (30 mg) in methanol (2 mL) was heated in a sealed tube at 80° C. for 16 hours. The solution was filtered through a plug of celite, evaporated, then passed through a plug of silica gel, eluting with 20% MeOH in dichloromethane. The residue was recrystallized from isopropanol/hexanes (10-20%) and collected by filtration to afford A3 as a white solid (0.011 g). HPLC retention time 2.37 min. Column:Chromolith SpeedROD 4.6×50 mm (4 min grad. 0% B-100% B) Solvent A: 10% MeOH-90% H₂O 0.1% TFA Solvent B: 90% MeOH-10% H₂O-0.1% TFA. MS (ES): m/z 352.3 [M+H]⁺

Example A4

N-[(R,S)1-[3-[7,8-Dimethyl-8H-imidazo[4,5-d]thiazolo[5.4-b]pyridin-2-yl]phenyl]ethyl]acetamide

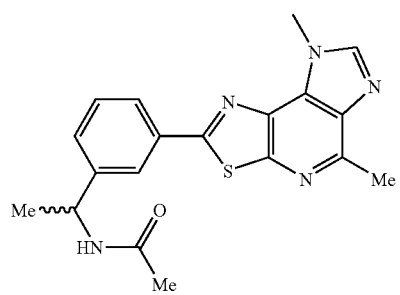

A4.1 3-(1-Acetamidoethyl)phenylboronic acid

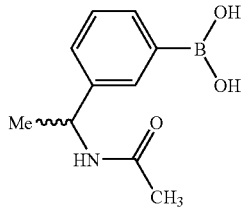

A4.1

A4.1a: 1-(3-Bromophenyl)ethanol

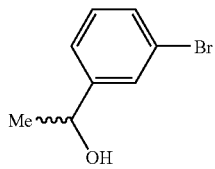

A4.1a

Commercially available 3-bromobenzaldehyde (5.0 g, 27 mmol) was dissolved in anhydrous dichloromethane (200 mL) under a dry nitrogen atmosphere and cooled in a dry ice/acetone bath to −78° C. Trimethyl aluminum 2M solution in toluene (16.2 mL, 32 mmol) was added dropwise. After 0.5 h the reaction mixture was allowed to warm to room temperature during which time the cloudiness of the reaction resolved to a clear yellow solution which then proceeded to a colorless solution. After stirring for 1 h at room temperature the reaction mixture was cooled in an ice bath and 1N HCl (100 mL) was added dropwise. The reaction mixture was transferred to a separatory funnel and the organic layer was isolated, dried over anhydrous magnesium sulfate, filtered and evaporated under reduced pressure. The crude product was purified by silica gel flash column chromatography eluting with 1:1 Ethyl acetate/hexane to provide 5.4 g (99%) of A4.1a as a colorless oil. LCMS (M+H−OH)$^+$=183, 185

A4.1b: N-(1-(3-Bromophenyl)ethyl)acetamide

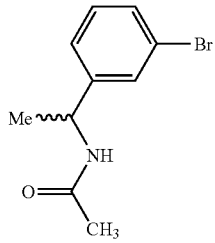

A4.1b

A4.1a (2.0 g, 10 mmol) and acetonitrile (825 mg, 20 mmol) were dissolved in dichloromethane (40 mL) under a nitrogen atmosphere at room temperature. Boron trifluoride etherate (1.9 g, 13 mmol) was added in one portion and the reaction was stirred in an oil bath maintained at 75° C. overnight. The reaction mixture was allowed to cool to room temperature and quenched by the addition of water. The layers were separated and the organic layer was dried over anhydrous magnesium sulfate, filtered and evaporated under reduced pressure. The residue was purified by silica gel flash column chromatography to provide 1.94 g (80%) as a viscous colorless oil. LCMS ret time=1.34 min (100%), (M+H)$^+$=242, 244.13. $^1$H NMR (CDCl$_3$, 400 MHz) δ 7.44 (s, 1H), 7.38 (d, J=7.6 Hz, 1H), 7.26-7.19 (m, 2H), 5.90 (br s, 1H), 5.15-5.05 (m. 1H), 1.98 (s, 3H), 1.45 (d, J=6.9 Hz, 3H)

A4.1c: 3-(1-Acetamidoethyl)phenylboronic acid (product A4.1)

A4.1b (507 mg, 2.1 mmol) was dissolved in anhydrous THF under nitrogen atmosphere and cooled in a dry ice/acetone bath (−78° C.). Methyl lithium 1.6 molar solution in THF (2.0 mL, 3.15 mmol) was added drop wise and the reaction mixture was stirred for 1 h. tert-Butyl lithium 1.7 molar solution in THF (3.6 mL, 6.22 mmol) was added drop wise and the reaction mixture was stirred for another 1 h at −78° C. Triisopropyl borate (2.75 mL, 12 mmol) was added drop wise and the reaction mixture allowed to stir at room temperature for 1.5 h. The reaction was quenched with 1N HCl (pH~1) and allowed to stir for 15 minutes to produce a bright pink solution. The layers were separated and the organic layer dried over anhydrous magnesium sulfate, filtered and evaporated under reduced pressure. The residue was taken up in ethyl acetate and filtered. The filtrate was evaporated under reduced pressure to provide 402 mg (92%) of A4.1 as an off-white crystalline solid. LCMS (M+H)$^+$=208.19.

A4.2: N-[(R,S)1-[3-[7-Chloro-8-methyl-8H-imidazo[4,5-d]thiazolo[5,4-b]pyridin-2-yl]phenyl]ethyl]acetamide

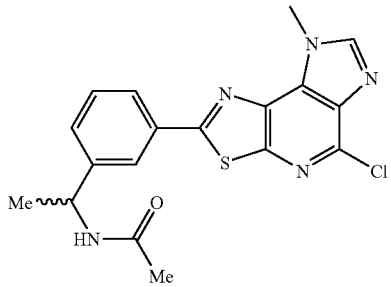

A4.2

A1.8 (500 mg, 1.6 mmol), A4.1 (380 mg, 1.8 mmol), lithium chloride (215 mg 5.1 mmol) tetrakis(triphenylphoshine)palladium (0) (100 mg, 0.08 mmol) and 2N aqueous sodium carbonate (4.15 mL) were added to a 1:1 mixture of toluene/ethanol and heated to 90° C. for 4 h. The reaction was allowed to cool to room temperature and stirred over the weekend. The reaction mixture was filtered to provide 494 mg (77%)of A4.2. LCMS 386.17, 388.16. $^1$H NMR (DMSO, 400 MHz) δ 8.68 (br s, 1H), 8.57 (s, 1H), 8.09-8.02 (m, 2H), 7.57 (br s, 2H) 5.02 (t, J=7.3 Hz, 1H), 4.34 (s, 3H) 1.89 (s, 3H), 1.41 (d, J=7.0 Hz, 3H).

A4.3: N-[(R,S)1-[3-[7,8-Dimethyl-8H-imidazo[4,5-d]thiazolo[5,4-b]pyridin-2-yl]phenyl]ethyl]acetamide A4.2 (0.010 g, 0.026 mmol), tetramethyltin (0.018 mL, 0.13 mmol), and dichlorobis(triphenylphosphine)palladium (II) (0.004 g, 0.0056 mmol) in DMF (1 mL) was heated in a C.E.M microwave reactor at 180° C. for 20 min. The solvent was partially evaporated under a stream of nitrogen. The residue was taken up in methanol, filtered, and purified by preparative reverse phase HPLC to afford A4 (1.74 mg, 1.0 TFA) as a pale yellow solid. HPLC retention time 2.37 min. Column:Chromolith SpeedROD 4.6×50 mm (4 min grad. 0% B-100% B) Solvent A: 10% MeOH-90% H$_2$O 0.1% TFA Solvent B: 90% MeOH-10% H$_2$O-0.1% TFA. MS (ES): m/z 352.3 [M+H]$^+$

Example A5

N-[(R,S)1-[3-[7-Methoxy-8-methyl-8H-imidazo[4,5-d]thiazolo[5,4-b]pyridin-2-yl]phenyl]ethyl]acetamide

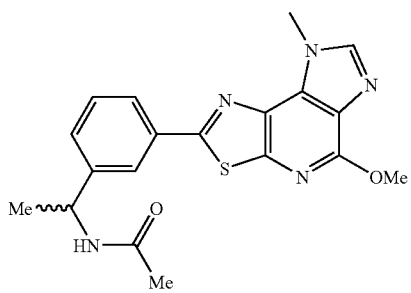

A5

To a solution of sodium methoxide in methanol (freshly prepared from sodium and dry methanol) was added A4.2 (0.005 g, 0.013 mmol). The solution was heated in a sealed tube at 80° C. for 4 h. The solvent was evaporated and the residue partitioned between chloroform and water. The organic phase was washed with brine, dried over MgSO$_4$, filtered, and evaporated. The residue was triturated with cold acetonitrile to afford A5 (0.0032 g) as a pale yellow solid. HPLC retention time 2.74 min. Column:Chromolith Speed-ROD 4.6×50 mm (4 min grad. 0% B-100% B) Solvent A: 10% MeOH-90% H$_2$O 0.1% TFA Solvent B: 90% MeOH-10% H$_2$O-0.1% TFA. MS (ES): m/z 382.2 [M+H]$^+$

Example A6

N-[(1-[3-[8-methyl-8H-imidazo[4,5-d]thiazolo[5,4-b]pyridin-2-yl]phenyl]-1-methylethyl]amine

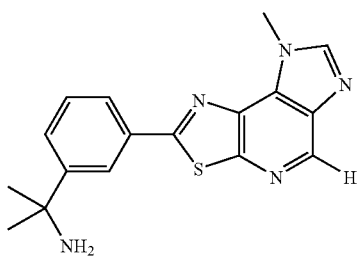

A6

A6.1 tert-butyl 2-(3-(4,4,5,5-tetramethyl-1,3,2-dioxaborolan-2-yl)phenyl)propan-2-ylcarbamate

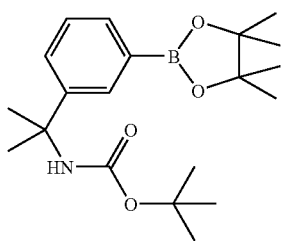

A6.1

A6.1a: Ethyl 2-(3-bromophenyl)acetate

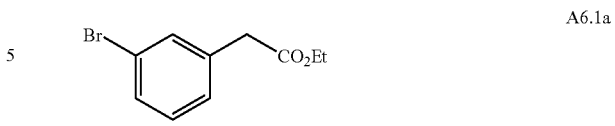

A6.1a

Commercially available 2-(3-bromophenyl)acetic acid (13 g 0.06 mol) was dissolved in ethanol (130 ml) and cooled to 0° C. Thionyl chloride (20 ml) was added drop wise. The mixture was heated to 85° C. over night. Reaction mixture was concentrated and the residue was dissolved in ethyl acetate. The organic layer was washed with 10% NaHCO$_3$, water, dried over anhydrous sodium sulfate and concentrated to give 13 g (88%) of A6.1a.

A6.1b: Ethyl 2-(3-bromophenyl)-2-methylpropanoate

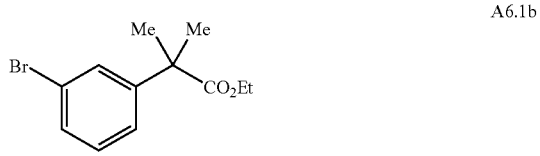

A6.1b

To a suspension of sodium hydride (60% in mineral oil, 10.8 g, 0.226 mol) in dry THF (150 ml) under N$_2$ atmosphere was added a THF (100 ml) solution of A6.1a (25 g, 0.1028 mol) at 0° C. drop wise. The reeaction mixture was stirred for 30 min. Methyl iodide (14.2 ml, 0.23 mol) was added drop wise at 0° C. and stirred at RT over night. Reaction mixture was quenched with ice and the aqueous layer was extracted with ethyl acetate. The combined organic layer was dried over anhydrous sodium sulfate, concentrated. To produce 22 g (79%) of A6.1b as a low melting solid. $^1$H NMR (300 MHz, CDCl$_3$) 1.24 (m, 3H), 1.52 (s, 6H), 4.15 (m, 2H), 7.22 (dd, 1H), 7.26 (d, 1H), 7.37 (d, 1H), 7.5 (s, 1H).

A6.1c: 2-(3-bromophenyl)-2-methylpropanoic acid

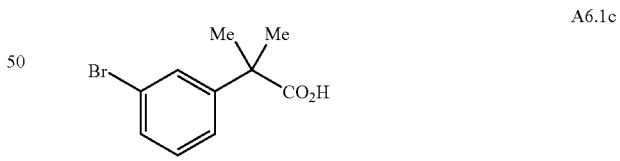

A6.1c

To a solution of A6.1b (22 g, 0.081 mol) in ethanol (220 ml) was added sodium hydroxide (9.7 g, 0.405 mol) and heated to reflux over night. The reaction mixture was concentrated to remove ethanol. The crude product was dissolved in water (200 ml) and washed with ether (2×150 ml). The aqueous later was acidified with 6N HCl and extracted with ethyl acetate. Combined organic layer was washed with water, brine, dried over anhydrous sodium sulfate and concentrated to give 17 g (86%) of A6.1c as white solid. $^1$H NMR (300 MHz, CDCl$_3$) 1.6 (s, 6H), 7.27 (dd, 1H), 7.35 (d, 1H), 7.4 (d, 1H), 7.55 (s, 1H).

A6.1d: Benzyl 2-(3-bromophenyl)propan-2-ylcarbamate

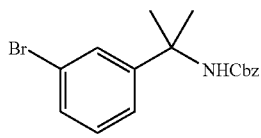

A6.1d

To solution of A6.1c (11 g, 0.045 mol) in dichloromethane (110 ml) was added triethylamine (5.85 g, 0.057 mol) and cooled to 0° C. under $N_2$. Ethylchloroformate (5.65 g, 0.05 mol) was added drop wise and stirred at 0° C. for 1 h. Sodium azide (3.24 g, 0.049 mol) was added and the mixture was stirred at RT over night. Reaction mixture was filtered to remove triethylamine-hydrochloride salt. The organic layer was concentrated to provide 1-azido-2-(3-bromophenyl)-2-methylpropan-1-one which was dissolved in toluene (60 mL) and heated to 100° C. for 30 min. The toluene was removed under vacuum to provide 1-bromo-3-(2-isocyanatopropan-2-yl)benzene. A mixture of 1-bromo-3-(2-isocyanatopropan-2-yl)benzene, pyridine (30 ml) and benzyl alcohol (12.2 g, 0.113 mol) was heated to 100° C. for 2 h under nitrogen. The reaction mixture was cooled to RT, quenched with 1.5 N HCl and extracted with ethyl acetate (3×50 ml). The combined organic layer was washed with water, brine, dried over anhydrous sodium sulfate and concentrated. Product was purified by column chromatography to give 7 g (45%) of A6.1d. 1H NMR (300 MHz, $CDCl_3$) 1.65 (s, 6H), 5.03 (s, 2H), 5.1 (bs, 1H), 7.2 (dd, 1H), 7.35 (m, 6H), 7.54 (s, 1H). LCMS $(M–H)^+=350$.

A6.1e Benzyl 2-(3-(4,4,5,5-tetramethyl-1,3,2-dioxaborolan-2-yl)phenyl)propan-2-ylcarbamate

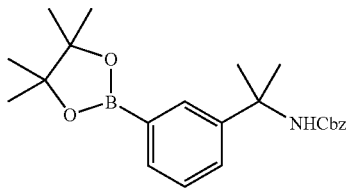

A6.1e

To a solution of A6.1d (5 g, 0.014 mol) in dioxane (75 ml) was added bispinacolatodiborane (5.5 g, 0.021 mol), dppf (0.64 g, 0.001 mol), $PdCl_2(dppf)$ (0.86 g, 0.001 mol), potassium acetate (4.23 g, 0.043 mol) and heated to 80° C. over night under $N_2$. Reaction mixture was concentrated to remove dioxane. The residue obtained was diluted with water and extracted with ethyl acetate. The combined organic layer was washed with water, brine, dried over anhydrous sodium sulfate and concentrated. Product was purified by column chromatography to give 4.3 g (76%) of A6.1e. $^1$H NMR 300 (MHz, $CDCl_3$) 1.33 (s, 12H), 1.7 (s, 6H), 5.02 (s, 2H), 5.20 (bs, 1H), 7.34 (m, 6H), 5 (d, 1H), 7.7 (d, 1H), 7.84 (s, 1H). LCMS (M+1)=396.

A6.1f: tert-butyl 2-(3-(4,4,5,5-tetramethyl-1,3,2-dioxaborolan-2-yl)phenyl)propan-2-ylcarbamate

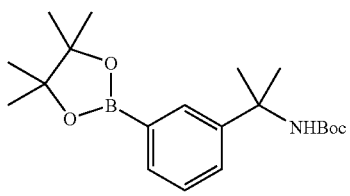

A6.1

To a solution of compound A6.1e (3 g, 0.008 mol) in ethanol (40 ml) and ethyl acetate (20 ml) was added palladium on carbon (1.5 g) and hydrogenated under 3 kg hydrogen pressure using a Parr shaker. After completion of the reaction, reaction mixture was filtered over Celite bed and concentrated to produce 2-(3-(4,4,5,5-tetramethyl-1,3,2-dioxaborolan-2-yl)phenyl)propan-2-amine. The amine was dissolved in chloroform and Boc anhydride (2.2 ml) was added drop wise at 0° C. and stirred at RT for over night. After completion of the reaction, reaction mixture was washed with water, dried over anhydrous sodium sulfate and concentrated. Product was purified by column chromatography to provide 1.7 g (63%) of A6.1. $^1$H NMR (300 MHz, $CDCl_3$) 1.34 (s, 12H), 1.64 (s, 6H), 4.95 (bs, 1H), 7.35 (dd, 1H), 7.48 (d, 1H), 7.68 (d, 1H), 7.83 (s, 1H). LCMS $[(M–100)+CH_3CN]=306$.

A6.2 N-[(1-[3-[7-Chloro-8-methyl-8H-imidazo[4,5-d]thiazolo[5,4-b]pyridin-2-yl]phenyl]-1-methylethyl] amine

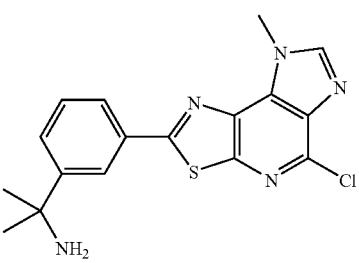

A6.2

A solution of A1.8 (1.0 g, 3.28 mmol), A6.1 (1.184 g, 3.28 mmol), dichlorobis(triphenylphosphine)palladium(II) (0.046 g, 0.066 mmol), and sodium carbonate (2N aq., 1.64 mL) in DME:Water:Ethanol (7:3:2, 18 mL) was divided into 3 equal portions and placed in capped C.E.M. microwave reaction tubes and processed in a C.E.M. microwave reactor at 150° C. for 20 min followed by an additional processing time of 40 min at 150° C. The reactions were combined and evaporated to dryness, then partitioned between water and ethyl acetate. The organic layer was dried over sodium sulfate and concentrated. The residue was suspended in HCl/Dioxane (4N, 20 mL). The solution was stirred at room temperature for 10 min, concentrated to dryness, slurried in diethyl ether, and filtered. The solids collected were purified by flash chromatography ($SiO_2$, 5-20% MeOH in dichloromethane) to afford A6.2 (1.2 g) as a yellow solid. HPLC retention time 2.38 min. Column: Chromolith SpeedROD 4.6×50 mm (4 min grad. 0% B-100% B) Solvent A: 10% MeOH-90% $H_2O$ 0.1% TFA Solvent B: 90% MeOH-10% $H_2O$-0.1% TFA. MS (ES): m/z 358.2 $[M+H]^+$

Step-A6.3 N-[(1-[3-[8-methyl-8H-imidazo[4,5-d]thiazolo[5,4-b]pyridin-2-yl]phenyl]-1-methylethyl] amine A solution of A6.2 (0.010 g, 0.028 mmol), Pd/C (5%, 0.010 g), and ammonium formate (0.015 g) in methanol (3 mL) was heated in a capped C.E.M. microwave reaction tube in a C.E.M. microwave reactor at 120° C. for 1 h. Additional processing time (6.5 h) was required to achieve complete conversion. An additional batch of A6.2 (30 mg), along with Pd/C (5%, 30 mg), and ammonium formate (45 mg) in methanol (6 mL) was processed in the C.E.M. microwave in a similar fashion until the reaction was complete. The combined reactions were filtered, concentrated, and the residue purified by preparative reverse phase HPLC to afford A6 (~75% purity, 0.0140 g). The material was used without further purification. HPLC retention time 1.99 min. Column: Chromolith SpeedROD 4.6×50 mm (4 min grad. 0% B-100% B) Solvent A: 10% MeOH-90% $H_2O$ 0.1% TFA Solvent B: 90% MeOH-10% $H_2O$-0.1% TFA. MS (ES): m/z 324.3 $[M+H]^+$

Example A7

N-[(1-[3-[8-methyl-8H-imidazo[4,5-d]thiazolo[5,4-b]pyridin-2-yl]phenyl]-1-methylethyl]acetamide

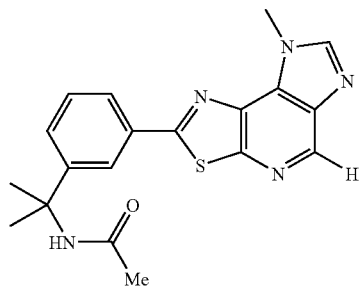

A7

To a solution of A6 (0.014 g, ~75% purity) and pyridine (0.8 mL) in THF (10 mL) was added acetic anhydride (0.05 mL). The solution was stirred at room temperature for 1-2 hours, then the solvents were partially evaporated and the residue residue purified by preparative reverse phase HPLC to afford A7 (0.0074 g, 1.0 TFA) as a white solid. HPLC retention time 2.01 min. Column:Chromolith SpeedROD 4.6×50 mm (4 min grad. 0% B-100% B) Solvent A: 10% MeOH-90% H$_2$O 0.1% TFA Solvent B: 90% MeOH-10% H$_2$O-0.1% TFA. MS (ES): m/z 366.2 [M+H]$^+$

Examples A8-A33

Examples A8-A36 was prepared starting with amine A6 and the appropriate carboxylic acid precursor using the following general procedure: The examples described in Table A1 were prepared by a solution phase library methodology. To an individual well of a 48-position MiniBlock® reactor was added 112 μL of a 0.50 M solution of the appropriate carboxylic acid in dimethylacetamide (DMA) (0.056 mmol, 1.7 equiv); 60 μL of a 0.93 M solution of 1-hydroxybenzotriazol in DMA (0.056 mmol, 1.7 equiv); 46 mg of polystyrene-supported N,N'-diisopropylcarbodiimide (PS-DIC) (1.21 mmol/g, 1.7 equiv); and 330 μL of 1,2-dichloroethane (DCE). The reactor was agitated via orbital shaker for 10 min. Finally, 300 μL of a 0.11 M solution of A6 in DMA (0.033 mmol, 1.0 equiv) was added to the reactor well, and the reactor was agitated for 14 h at rt. The crude product was filtered, rinsed with additional DMA, then purified by standard preparative HPLC-MS (H$_2$O/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS H$_2$O/MeOH/0.1% TFA, gradient 10-90% MeOH over 4 min, 4 mL/min, 4.6×50 mm 5 um Phenomenex® Primesphere column Retention time and observed mass are reported.

For those compounds which were derived from amino acid acid labile protecting groups were utilized (Boc group). These examples were coupled as described above and the protecting group(s) were removed by being taken up in 1 mL of 2:1/DCE:TFA for 1 hour, then concentrated again. Purification was performed by standard preparative HPLC-MS as described above.

TABLE A1

| Ex. | R$^1$ | Name | HPLC Retention (min) | MS Reported |
|-----|-------|------|----------------------|-------------|
| A8 | cyclopropyl | N-[1-methyl-1-[3-(8-methyl-8H-imidazo[4,5-d]thiazolo[5,4-b]pyridin-2-yl)phenyl]ethyl]-cyclopropanecarboxamide | 3.04 | 392.43 |
| A9 | MeO-CH$_2$- | 2-methoxy-N-[1-methyl-1-[3-(8-methyl-8H-imidazo[4,5-d]thiazolo[5,4-b]pyridin-2-yl)phenyl]ethyl]acetamide | 3.01 | 396.41 |
| A10 | EtO-CH$_2$- | 2-ethoxy-N-[1-methyl-1-[3-(8-methyl-8H-imidazo[4,5-d]thiazolo[5,4-b]pyridin-2-yl)phenyl]ethyl]-acetamide | 3.21 | 410.41 |

TABLE A1-continued

| Ex. | R¹ | Name | HPLC Retention (min) | MS Reported |
|---|---|---|---|---|
| A11 | 2-pyridinyl N-oxide | N-[1-methyl-1-[3-(8-methyl-8H-imidazo[4,5-d]thiazolo[5,4-b]pyridin-2-yl)phenyl]ethyl]-2-pyridinecarboxamide-1-oxide | 3.17 | 445.35 |
| A12 | 3-pyridinyl N-oxide | ,N-[1-methyl-1-[3-(8-methyl-8H-imidazo[4,5-d]thiazolo[5,4-b]pyridin-2-yl)phenyl]ethyl]-3-pyridinecarboxamide-1-oxide | 2.76 | 445.33 |
| A13 | 4-pyridinyl N-oxide | N-[1-methyl-1-[3-(8-methyl-8H-imidazo[4,5-d]thiazolo[5,4-b]pyridin-2-yl)phenyl]ethyl]-4-pyridinecarboxamide-1-oxide | 2.76 | 445.35 |
| A14 | 2-pyridinyl | N-[1-methyl-1-[3-(8-methyl-8H-imidazo[4,5-d]thiazolo[5,4-b]pyridin-2-yl)phenyl]ethyl]-2-pyridmecarboxamide | 3.41 | 429.35 |
| A15 | 3-pyridinyl | N-[1-methyl-1-[3-(8-methyl-8H-imidazo[4,5-d]thiazolo[5,4-b]pyridin-2-yl)phenyl]ethyl]-3-pyridinecarboxamide | 2.68 | 429.35 |
| A16 | 4-pyridinyl | N-[1-methyl-1-[3-(8-methyl-8H-imidazolol[5,4-b]pyridin-2-yl)phenyl[ethyl]-4-pyridinecarboxamide | 2.64 | 429.39 |
| A17 | tetrahydrofuran-2-yl | tetrahydro-N-[1-methyl-1-[3-(8-methyl-8H-imidazo[4,5-d]thiazolol[5,4-b]pyridin-2-yl)phenyl]ethyl]-2-furancarboxamide | 3.12 | 422.41 |
| A18 | 1,2,3-thiadiazol-4-yl | N-[1-methyl-1-[3-(8-methyl-8H-imidazo[4,5-d]thiazolo[5,4-b]pyridin-2-yl)phenyl]ethyl]-1,2,3-thiadiazole-4-carboxamide | 3.19 | 436.31 |
| A19 | 3-pyridinylmethyl | N-[1-methyl-1-[3-(8-methyl-8H-imidazo[4,5-d]thiazolo[5,4-b]pyridin-2-yl)phenyl]ethyl]-3-pyridineacetamide | 2.55 | 443.35 |

TABLE A1-continued

| Ex. | R¹ | Name | HPLC Retention (min) | MS Reported |
|---|---|---|---|---|
| A20 | (1-methyl-4-piperidinyl) | 1-methyl-N-[1-methyl-1-[3-(8-methyl-8H-imidazo[4,5-d]thiazolo[5,4-b]pyridin-2-yl)phenyl]ethyl]-4-piperidinecarboxamide | 2.56 | 449.41 |
| A21 | (1-methyl-3-piperidinyl) | 1-methyl-N-[1-methyl-1-[3-(8-methyl-8H-imidazo[4,5-d]thiazolo[5,4-b]pyridin-2-yl)phenyl]ethyl]-3-piperidinecarboxamide | 2.57 | 449.41 |
| A22 | 1-cyanocyclopropyl | 1-cyano-N-[1-methyl-1-[3-(8-methyl-8H-imidazo[4,5-d]thiazolo[5,4-b]pyridin-2-yl)phenyl]ethyl]-cyclopropanecarboxamide | 3.11 | 417.37 |
| A23 | 5-methylisoxazol-3-yl | 5-methyl-N-[1-methyl-1-[3-(8-methyl-8H-imidazo[4,5-d]thiazolo[5,4-b]pyridin-2-yl)phenyl]ethyl]-3-isoxazolecarboxamide | 3.24 | 433.35 |
| A24 | (2S)-5-oxopyrrolidin-2-yl | N-[1-methyl-1-[3-(8-methyl-8H-imidazo[4,5-d]thiazolol[5,4-b]pyridin-2-yl)phenyl]ethyl]-5-oxo-,(2S)-2-pyrrolidinecarboxamide | 2.74 | 435.38 |
| A25 | 3-methoxy-2,2-dimethylpropyl (MeO-) | 3-methoxy-N-[1-methyl-1-[3-(8-methyl-8H-imidazo[4,5-d]thiazolo[5,4-b]pyridin-2-yl)phenyl]ethyl]-propanamide | 2.95 | 410.41 |
| A26 | 2-amino-2-methylpropyl (H₂N-) | 2-amino-N-[1-methyl-1-[3-(8-methyl-8H-imidazo[4,5-d]thiazolo[5,4-b]pyridin-2-yl)phenyl]ethyl]-acetamide | 3.37 | 481.35* |

TABLE A1-continued

| Ex. | R¹ | Name | HPLC Retention (min) | MS Reported |
|---|---|---|---|---|
| A27 | H₂N-CH₂CH₂-C(CH₃)₂- | 3-amino-N-[1-methyl-1-[3-(8-methyl-8H-imidazo[4,5-d]thiazolo[5,4-b]pyridin-2-yl)phenyl]ethyl]-propanamide | 3.44 | 495.35* |
| A28 | 4-piperidinyl (HN) | N-[1-methyl-1-[3-(8-methyl-8H-imidazo[4,5-d]thiazolol[5,4-b]pyridin-2-yl)phenyl]ethyl]-4-piperidinecarboxamide, | 3.53 | 535.36* |
| A29 | 1-amino-cyclopropyl (H₂N) | 1-amino-N-[1-methyl-1-[3-(8-methyl-8H-imidazo[4,5-d]thiazolo[5,4-b]pyridin-2-yl)phenyl]ethyl]-cyclopropanecarboxamide | 3.53 | 507.38* |
| A30 | (2S)-2-piperidinyl (HN) | N-[1-methyl-1-[3-(8-methyl-8H-imidazo[4,5-d]thiazolo[5,4-b]pyridin-2-yl)phenyl]ethyl]-,(2S)-2-piperidinecarboxamide | 3.66 | 535.37* |
| A31 | 3-piperidinyl (NH) | N-[1-methyl-1-[3-(8-methyl-8H-imidazo[4,5-d]thiazolo[5,4-b]pyridin-2-yl)phenyl]ethyl]-3-piperidinecarboxamide | 3.64 | 535.37* |
| A32 | 2-morpholinyl (O, NH) | N-[1-methyl-1-[3-(8-methyl-8H-imidazo[4,5-d]thiazolo[5,4-b]pyridin-2-yl)phenyl]ethyl]-2-morpholinecarboxamide, | 3.56 | 537.36* |
| A33 | 4-amino-tetrahydrothiopyran-1,1-dioxide (H₂N, SO₂) | 4-aminotetrahydro-N-[1-methyl-1-[3-(8-methyl-8H-imidazo[4,5-d]thiazolo[5,4-b]pyridin-2-yl)phenyl]ethyl]-1,1-dioxide-2H-thiopyran-4-carboxamide | 3.41 | 599.30* |

*mass represents Boc protected material

Example A34

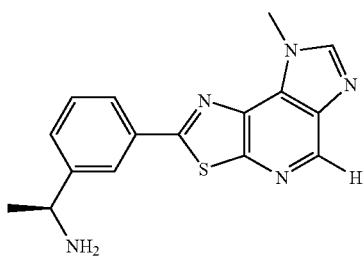

A34

A solution of A-1 (0.90 g, 2.6 mmol), Pd/C (10%, 0.30 g) and ammonium formate (0.60 g) in isopropyl alcohol (500 mL) was heated to 65° C. After 1.5 hours, additional ammonium formate (0.20 g) was added and heating continued for an additional hour. Another portion of ammonium formate (0.20 g) was added and heating continued for an additional hour. Pd/C (10%, 0.20 g) and ammonium formate (0.40 g) were added and heating continued for 72 hours. Another portion of Pd/C (10%, 0.05 g) and ammonium formate (0.10 g) was added and heating continued for 5 hours. The reaction was filtered through a membrane filter and washed with hot methanol. The solid was suspended in dioxane and 4N HCl/dioxane was added. After stirring at room temp overnight, the product was collected and dried under vacuum to afford A34 (0.727 g, HCl salt) as a white solid. HPLC retention time 2.34 min. Column:Chromolith SpeedROD 4.6×50 mm (4 min grad. 0% B-100% B) Solvent A: 10% MeOH-90% $H_2O$ 0.1% TFA Solvent B: 90% MeOH-10% $H_2O$-0.1% TFA. MS (ES): m/z 310.3 $[M+H]^+$

Examples A35-A140

The compounds in Table A2 were prepared in a similar manner for those described in Table A1 starting with amine A34 and the appropriate carboxylic acid.

TABLE A2

| Ex. | R¹ | Name | HPLC Retention (min) | MS Reported |
|---|---|---|---|---|
| A35 | H₂N— (propyl) | 3-amino-N-[(1S)-1-[3-(8-methyl-8H-imidazo[4,5-d]thiazolo[5,4-b]pyridin-2-yl)phenyl]ethyl]-propanamide | 2.29 | 381.13 |
| A36 | H₂N— (ethyl) | 2-amino-N-[(1S)-1-[3-(8-methyl-8H-imidazo[4,5-d]thiazolo[5,4-b]pyridin-2-yl)phenyl]ethyl]-acetamide | 2.21 | 367.10 |
| A37 | pyrrolidinyl NH | N-[(1S)-1-[3-(8-methyl-8H-imidazo[4,5-d]thiazolo[5,4-b]pyridin-2-yl)phenyl]ethyl]-(2S)-2-pyrrolidinecarboxamide | 2.29 | 407.14 |
| A38 | EtHN— | 2-(ethylamino)-N-[(1S)-1-[3-(8-methyl-8H-imidazo[4,5-d]thiazolol[5,4-b]pyridin-2-yl)phenyl]ethyl]-acetamide | 2.27 | 395.13 |
| A39 | azetidinyl NH | N-[(1S)-1-[3-(8-methyl-8H-imidazo[4,5-d]thiazolo[5,4-b]pyridin-2-yl)phenyl]ethyl]-(2S)-2-azetidinecarboxamide, | 2.54 | 393.13 |

TABLE A2-continued

| Ex. | R¹ | Name | HPLC Retention (min) | MS Reported |
|---|---|---|---|---|
| A40 | piperidin-4-yl (HN) | N-[(1S)-1-[3-(8-methyl-8H-imidazo[4,5-d]thiazolo[5,4-b]pyridin-2-yl)phenyl]ethyl]-4-piperidinecarboxamide | 2.34 | 421.15 |
| A41 | piperidin-3-yl (NH) | N-[(1S)-1-[3-(8-methyl-8H-imidazo[4,5-d]thiazolo[5,4-b]pyridin-2-yl)phenyl]ethyl]-3-piperidinecarboxamide | 2.39 | 421.14 |
| A42 | (2S)-piperidin-2-yl | N-[(1S)-1-[3-(8-methyl-8H-imidazo[4,5-d]thiazolo[5,4-b]pyridin-2-yl)phenyl]ethyl]-(2S)-2-piperidinecarboxamide, | 2.33 | 421.15 |
| A43 | 1,2,3-thiadiazol-4-yl | N-[(1S)-1-[3-(8-methyl-8H-imidazo[4,5-d]thiazolo[5,4-b]pyridin-2-yl)phenyl]ethyl]-1,2,3-thiadiazole-4-carboxamide | 3.02 | 422.02 |
| A44 | 5-methylisoxazol-3-yl | 5-methyl-N-[(1S)-1-[3-(8-methyl-8H-imidazo[4,5-d]thiazolo[5,4-b]pyridin-2-yl)phenyl]ethyl]-3-isoxazolecarboxamide | 3.10 | 419.09 |
| A45 | 5-oxo-(2S)-pyrrolidin-2-yl | N-[(1S)-1-[3-(8-methyl-8H-imidazo[4,5-d]thiazolo[5,4-b]pyridin-2-yl)phenyl]ethyl]-5-oxo-(2S)-2-pyrrolidinecarboxamide | 2.55 | 421.09 |
| A46 | 1-methylcyclopropyl | 1-methyl-N-[(1S)-1-[3-(8-methyl-8H-imidazo[4,5-d]thiazolo[5,4-b]pyridin-2-yl)phenyl]ethyl]-cyclopropanecarboxamide | 3.04 | 392.13 |
| A47 | MeOCH₂- | 2-methoxy-N-[(1S)-1-[3-(8-methyl-8H-imidazo[4,5-d]thiazolo[5,4-b]pyridin-2-yl)phenyl]ethyl]-acetamide | 2.79 | 382.09 |

TABLE A2-continued

| Ex. | R¹ | Name | HPLC Retention (min) | MS Reported |
|---|---|---|---|---|
| A48 | tetrahydrofuran-2-yl | tetrahydro-N-[(1S)-1-[3-(8-methyl-8H-imidazo[4,5-d]thiazolo[5,4-b]pyridin-2-yl)phenyl]ethyl]-2-furancarboxamide | 2.88 | 408.10 |
| A49 | EtOCH₂C(CH₃)₂— | 2-ethoxy-N-[(1S)-1-[3-(8-methyl-8H-imidazo[4,5-d]thiazolo[5,4-b]pyridin-2-yl)phenyl]ethyl]-acetamide | 2.98 | 396.11 |
| A50 | pyridin-2-yl N-oxide | N-[(1S)-1-[3-(8-methyl-8H-imidazo[4,5-d]thiazolo[5,4-b]pyridin-2-yl)phenyl]ethyl]-2-pyridinecarboxamide-1-oxide | 3.00 | 431.08 |
| A51 | pyridin-3-yl N-oxide | N-[(1S)-1-[3-(8-methyl-8H-imidazo[4,5-d]thiazolo[5,4-b]pyridin-2-yl)phenyl]ethyl]-3-pyridinecarboxamide,1-oxide | 2.65 | 431.09 |
| A52 | pyridin-4-yl N-oxide | ,N-[(1S)-1-[3-(8-methyl-8H-imidazo[4,5-d]thiazolo[5,4-b]pyridin-2-yl)phenyl]ethyl]-4-pyridinecarboxamide 1-oxide | 2.65 | 431.07 |
| A53 | 6-cyanopyridin-3-yl | 6-cyano-N-[(1S)-1-[3-(8-methyl-8H-imidazo[4,5-d]thiazolo[5,4-b]pyridin-2-yl)phenyl]ethyl]-3-pyridinecarboxamide | 3.06 | 440.09 |
| A54 | Et— | N-[(1S)-1-[3-(8-methyl-8H-imidazo[4,5-d]thiazolo[5,4-b]pyridin-2-yl)phenyl]ethyl]-propanamide | 2.79 | 336.12 |
| A55 | 1-methylpiperidin-4-yl | 1-methyl-N-[(1S)-1-[3-(8-methyl-8H-imidazo[4,5-d]thiazolo[5,4-b]pyridin-2-yl)phenyl]ethyl]-4-piperidinecarboxamide | 2.32 | 435.12 |

TABLE A2-continued

| Ex. | R¹ | Name | HPLC Retention (min) | MS Reported |
|---|---|---|---|---|
| A56 | *N-methylpiperidin-3-yl (gem-dimethyl)* | 1-methyl-N-[(1S)-1-[3-(8-methyl-8H-imidazo[4,5-d]thiazolo[5,4-b]pyridin-2-yl)phenyl]ethyl]-3-piperidinecarboxamide | 2.33 | 435.15 |
| A57 | *2-(acetylamino)-1,1-dimethylethyl* | 2-(acetylamino)-N-[(1S)-1-[3-(8-methyl-8H-imidazo[4,5-d]thiazolo[5,4-b]pyridin-2-yl)phenyl]ethyl]-acetamide | 2.53 | 409.13 |
| A58 | *1-cyclopropyl (gem-dimethyl)* | N-[(1S)-1-[3-(8-methyl-8H-imidazo[4,5-d]thiazolo[5,4-b]pyridin-2-yl)phenyl]ethyl]-cyclopropanecarboxamide | 2.87 | 378.12 |
| A59 | *3-(methylsulfonyl)phenyl* | N-[(1S)-1-[3-(8-methyl-8H-imidazo[4,5-d]thiazolo[5,4-b]pyridin-2-yl)phenyl]ethyl]-3-(methylsulfonyl)-benzamide | 2.98 | 492.33 |
| A60 | *2-(methylsulfonyl)phenyl* | N-[(1S)-1-[3-(8-methyl-8H-imidazo[4,5-d]thiazolo[5,4-b]pyridin-2-yl)phenyl]ethyl]-2-(methylsulfonyl)-benzamide | 2.89 | 492.30 |
| A61 | *pyridin-2-yl* | N-[(1S)-1-[3-(8-methyl-8H-imidazo[4,5-d]thiazolo[5,4-b]pyridin-2-yl)phenyl]ethyl]-2-pyridinecarboxamide | 3.27 | 415.43 |
| A62 | *pyridin-3-ylmethyl* | N-[(1S)-1-[3-(8-methyl-8H-imidazo[4,5-d[thiazolo[5,4-b]pyridin-2-yl)phenyl]ethyl]-3-pyridineacetamide | 2.43 | 429.41 |
| A63 | *(1-methyl-1H-imidazol-4-yl)methyl* | 1-methyl-N-[(1S)-1-[3-(8-methyl-8H-imidazo[4,5-d]thiazolo[5,4-b]pyridin-2-yl)phenyl]ethyl]-1H-imidazole-4-acetamide | 2.41 | 432.41 |

TABLE A2-continued

| Ex. | R¹ | Name | HPLC Retention (min) | MS Reported |
|---|---|---|---|---|
| A64 | (pyrrolidine with N-acetyl) | 1-acetyl-N-[(1S)-1-[3-(8-methyl-8H-imidazo[4,5-d]thiazolo[5,4-b]pyridin-2-yl)phenyl]ethyl]-,(2S)-2-pyrrolidinecarboxamide, | 2.75 | 449.41 |
| A65 | (pyrazinyl) | N-[(1S)-1-[3-(8-methyl-8H-imidazo[4,5-d]thiazolo[5,4-b]pyridin-2-yl)phenyl]ethyl]-2-pyrazinecarboxamide | 3.04 | 416.40 |
| A66 | (N-methylpiperazinyl-CH₂-) | 4-methyl-N-[(1S)-1-[3-(8-methyl-8H-imidazo[4,5-d]thiazolo[5,4-b]pyridin-2-yl)phenyl]ethyl]-1-piperazineacetamide | 2.36 | 450.46 |
| A67 | Me₂N— | 2-(dimethylamino)-N-[(1S)-1-[3-(8-methyl-8H-imidazo[4,5-d]thiazolo[5,4-b]pyridin-2-yl)phenyl]ethyl]-acetamide | 2.35 | 395.48 |
| A68 | (4-pyridyl) | N-[(1S)-1-[3-(8-methyl-8H-imidazo[4,5-d]thiazolo[5,4-b]pyridin-2-yl)phenyl]ethyl]-4-pyridinecarboxamide | 2.58 | 415.41 |
| A69 | (3-pyridyl) | N-[(1S)-1-[3-(8-methyl-8H-imidazo[4,5-d]thiazolo[5,4-b]pyridin-2-yl)phenyl]ethyl]-3-pyridinecarboxamide | 2.64 | 415.41 |
| A70 | HO-(cyclopropyl) | 1-hydroxy-N-[(1S)-1-[3-(8-methyl-8H-imidazo[4,5-d]thiazolo[5,4-b]pyridin-2-yl)phenyl]ethyl]-cyclopropanecarboxamide | 2.79 | 394.41 |
| A71 | NC-(cyclopropyl) | 1-cyano-N-[(1S)-1-[3-(8-methyl-8H-imidazo[4,5-d]thiazolo[5,4-b]pyridin-2-yl)phenyl]ethyl]-cyclopropanecarboxamide | 3.01 | 403.41 |
| A72 | HO— | 2-hydroxy-N-[(1S)-1-[3-(8-methyl-8H-imidazo[4,5-d]thiazolo[5,4-b]pyridin-2-yl)phenyl]ethyl]-acetamide | 2.63 | 368.44 |

TABLE A2-continued

| Ex. | R¹ | Name | HPLC Retention (min) | MS Reported |
|---|---|---|---|---|
| A73 | MeO-C(CH₃)₂-CH₂- (with OMe) | 3-methoxy-N-[(1S)-1-[3-(8-methyl-8H-imidazo[4,5-d]thiazolo[5,4-b]pyridin-2-yl)phenyl]ethyl]-propanamide | 2.80 | 396.43 |
| A74 | H₂N-SO₂-CH₂CH₂CH₂-C(CH₃)₂- | 4-(aminosulfonyl)-N-[(1S)-1-[3-(8-methyl-8H-imidazo[4,5-d]thiazolo[5,4-b]pyridin-2-yl)phenyl]ethyl] butanamide | 2.60 | 459.35 |
| A75 | 2-methylpyridin-3-yl | 2-methyl-N-[(1S)-1-[3-(8-methyl-8H-imidazo[4,5-d]thiazolo[5,4-b]pyridin-2-yl)phenyl]ethyl]-3-pyridinecarboxamide | 2.51 | 429.41 |
| A76 | 5-methylpyridin-3-yl | 5-methyl-N-[(1S)-1-[3-(8-methyl-8H-imidazo[4,5-d]thiazolo[5,4-b]pyridin-2-yl)phenyl]ethyl]-3-pyridinecarboxamide | 2.68 | 429.41 |
| A77 | 2-fluoropyridin-4-yl | 2-fluoro-N-[(1S)-1-[3-(8-methyl-8H-imidazo[4,5-d]thiazolo[5,4-b]pyridin-2-yl)phenyl]ethyl]-4-pyridinecarboxamide | 3.16 | 433.40 |
| A78 | 2-fluoropyridin-3-yl | 2-fluoro-N-[(1S)-1-[3-(8-methyl-8H-imidazo[4,5-d]thiazolo[5,4-b]pyridin-2-yl)phenyl]ethyl]-3-pyridinecarboxamide | 3.00 | 433.38 |
| A79 | 6-fluoropyridin-3-yl | 6-fluoro-N-[(1S)-1-[3-(8-methyl-8H-imidazo[4,5-d]thiazolo[5,4-b]pyridin-2-yl)phenyl]ethyl]-3-pyridinecarboxamide | 3.13 | 433.38 |
| A80 | 3-fluoropyridin-4-yl | 3-fluoro-N-[(1S)-1-[3-(8-methyl-8H-imidazo[4,5-d]thiazolo[5,4-b]pyridin-2-yl)phenyl]ethyl]-4-pyridinecarboxamide | 2.98 | 433.38 |
| A81 | 4,6-dimethylpyridin-3-yl | 4,6-dimethyl-N-[(1S)-1-[3-(8-methyl-8H-imidazo[4,5-d]thiazolo[5,4-b]pyridin-2-yl)phenyl]ethyl]-3-pyridinecarboxamide | 2.55 | 443.41 |

TABLE A2-continued

| Ex. | R¹ | Name | HPLC Retention (min) | MS Reported |
|---|---|---|---|---|
| A82 | 2,6-dimethoxypyridin-3-yl (MeO, OMe) | 2,6-dimethoxy-N-[(1S)-1-[3-(8-methyl-8H-imidazo[4,5-d]thiazolo[5,4-b]pyridin-2-yl)phenyl]ethyl]-3-pyridinecarboxamide | 3.73 | 475.41 |
| A83 | 6-(1H-pyrazol-1-yl)pyridin-3-yl | N-[(1S)-1-[3-(8-methyl-8H-imidazo[4,5-d]thiazolo[5,4-b]pyridin-2-yl)phenyl]ethyl]-6-(1H-pyrazol-1-yl)-3-pyridinecarboxamide | 3.44 | 481.40 |
| A84 | 1-acetylpiperidin-4-yl | 1-acetyl-N-[(1S)-1-[3-(8-methyl-8H-imidazo[4,5-d]thiazolo[5,4-b]pyridin-2-yl)phenyl]ethyl]-4-piperidinecarboxamide | 2.79 | 463.41 |
| A85 | 4-(methylsulfonyl)phenyl | N-[(1S)-1-[3-(8-methyl-8H-imidazo[4,5-d]thiazolo[5,4-b]pyridin-2-yl)phenyl]ethyl]-4-(methylsulfonyl)-benzamide | 2.97 | 492.32 |
| A86 | pyridazin-4-yl | N-[(1S)-1-[3-(8-methyl-8H-imidazo[4,5-d]thiazolo[5,4-b]pyridin-2-yl)phenyl]ethyl]-4-pyridazinecarboxamide | 2.81 | 416.40 |
| A87 | benzyl | N-[(1S)-1-[3-(8-methyl-8H-imidazo[4,5-d]thiazolo[5,4-b]pyridin-2-yl)phenyl]ethyl]-benzeneacetamide | 3.25 | 428.43 |
| A88 | cyclobutyl | N-[(1S)-1-[3-(8-methyl-8H-imidazo[4,5-d]thiazolo[5,4-b]pyridin-2-yl)phenyl]ethyl]-cyclobutanecarboxamide | 3.10 | 392.48 |
| A89 | α,α-dimethylbenzyl (Me, Me) | N-[(1S)-1-[3-(8-methyl-8H-imidazo[4,5-d]thiazolo[5,4-b]pyridin-2-yl)phenyl]ethyl]-alpha,alpha-dimethyl-benzeneacetamide | 3.56 | 456.43 |
| A90 | pyridin-4-ylmethyl | N-[(1S)-1-[3-(8-methyl-8H-imidazo[4,5-d]thiazolo[5,4-b]pyridin-2-yl)phenyl]ethyl]-4-pyridineacetamide | 2.42 | 429.40 |

TABLE A2-continued

| Ex. | R¹ | Name | HPLC Retention (min) | MS Reported |
|---|---|---|---|---|
| A91 | Ph-O-pyridin-2-yl (6-position) | N-[(1S)-1-[3-(8-methyl-8H-imidazo[4,5-d]thiazolo[5,4-b]pyridin-2-yl)phenyl]ethyl]-6-phenoxy-3-pyridinecarboxamide | 3.56 | 507.37 |
| A92 | F₃C-CH₂-O-pyridin-2-yl (6-position) | N-[(1S)-1-[3-(8-methyl-8H-imidazo[4,5-d]thiazolo[5,4-b]pyridin-2-yl)phenyl]ethyl]-6-(2,2,2-trifluoroethoxy)-3-pyridinecarboxamide | 3.63 | 513.33 |
| A93 | 6-Me, 2-OH pyridin-3-yl | 2-hydroxy-6-methyl-N-[(1S)-1-[3-(8-methyl-8H-imidazo[4,5-d]thiazolo[5,4-b]pyridin-2-yl)phenyl]ethyl]-3-pyridinecarboxamide | 3.14 | 445.39 |
| A94 | 2-OMe pyridin-3-yl | 2-methoxy-N-[(1S)-1-[3-(8-methyl-8H-imidazo[4,5-d]thiazolo[5,4-b]pyridin-2-yl)phenyl]ethyl]-3-pyridinecarboxamide | 3.33 | 445.40 |
| A95 | 6-OH pyridin-3-yl | 6-hydroxy-N-[(1S)-1-[3-(8-methyl-8H-imidazo[4,5-d]thiazolo[5,4-b]pyridin-2-yl)phenyl]ethyl]-3-pyridinecarboxamide | 2.80 | 431.36 |
| A96 | 2-OH pyridin-3-yl | 2-hydroxy-N-[(1S)-1-[3-(8-methyl-8H-imidazo[4,5-d]thiazolo[5,4-b]pyridin-2-yl)phenyl]ethyl]-3-pyridinecarboxamide | 3.03 | 431.41 |
| A97 | 6-Me pyridin-3-yl | 6-methyl-N-[(1S)-1-[3-(8-methyl-8H-imidazo[4,5-d]thiazolo[5,4-b]pyridin-2-yl)phenyl]ethyl]-3-pyridinecarboxamide | 2.55 | 429.41 |
| A98 | 6-Cl pyridin-3-yl | 6-chloro-N-[(1S)-1-[3-(8-methyl-8H-imidazo[4,5-d]thiazolo[5,4-b]pyridin-2-yl)phenyl]ethyl]-3-pyridinecarboxamide | 3.23 | 449.34 |
| A99 | 2-Cl pyridin-3-yl | 2-chloro-N-[(1S)-1-[3-(8-methyl-8H-imidazo[4,5-d]thiazolo[5,4-b]pyridin-2-yl)phenyl]ethyl]-3-pyridinecarboxamide | 2.95 | 449.35 |

TABLE A2-continued

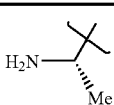

| Ex. | R¹ | Name | HPLC Retention (min) | MS Reported |
|---|---|---|---|---|
| A100 | 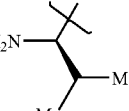 | 2-amino-N-[(1S)-1-[3-(8-methyl-8H-imidazo[4,5-d]thiazolo[5,4-b]pyridin-2-yl)phenyl]ethyl]-,(2S)-propanamide | 2.35 | 381.41 |
| A101 | | 2-amino-3-methyl-N-[(1S)-1-[3-(8-methyl-8H-imidazo[4,5-d]thiazolo[5,4-b]pyridin-2-yl)phenyl]ethyl]-(2R)-butanamide | 2.61 | 409.41 |
| A102 | | alpha-amino-N-[(1S)-1-[3-(8-methyl-8H-imidazo[4,5-d]thiazolo[5,4-b]pyridin-2-yl)phenyl]ethyl]-,(alphaR)-benzeneacetamide | 2.76 | 443.35 |
| A103 | 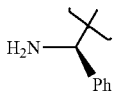 | N~1~[(1S)-1-[3-(8-methyl-8H-imidazo[4,5-d]thiazolo[5,4-b]pyridin-2-yl)phenyl]ethyl] D-aspartamide, | 2.27 | 424.35 |
| A104 | | alpha-amino-N-[(1S)-1-[3-(8-methyl-8H-imidazo[4,5-d]thiazolo[5,4-b]pyridin-2-yl)phenyl]ethyl]-,(alphaR)-benzenepropanamide | 2.95 | 457.35 |
| A105 | 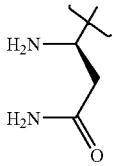 | N-[(1S)-1-[3-(8-methyl-8H-imidazo[4,5-d]thiazolo[5,4-b]pyridin-2-yl)phenyl]ethyl]-(2S)-2-pyrrolidineacetamide, | 2.41 | 421.41 |
| A106 | 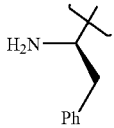 | N-[(1S)-1-[3-(8-methyl-8H-imidazo[4,5-d]thiazolo[5,4-b]pyridin-2-yl)phenyl]ethyl]-3-morpholinecarboxamide | 2.36 | 423.35 |
| A107 | 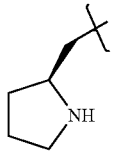 | 2-amino-3-methoxy-N-[(1S)-1-[3-(8-methyl-8H-imidazo[4,5-d]thiazolo[5,4-b]pyridin-2-yl)phenyl]ethyl]-(2S)-propanamide | 2.38 | 411.41 |

TABLE A2-continued

| Ex. | R¹ | Name | HPLC Retention (min) | MS Reported |
|---|---|---|---|---|
| A108 | H₂N-C(Me)(Me)- | 2-amino-2-methyl-N-[(1S)-1-[3-(8-methyl-8H-imidazo[4,5-d]thiazolo[5,4-b]pyridin-2-yl)phenyl]ethyl]-propanamide | 2.33 | 395.41 |
| A109 | 1-aminocyclopropyl | 1-amino-N-[(1S)-1-[3-(8-methyl-8H-imidazo[4,5-d]thiazolo[5,4-b]pyridin-2-yl)phenyl]ethyl]-cyclopropanecarboxamide | 2.33 | 393.41 |
| A110 | 1-aminocyclohexyl | 1-amino-N-[(1S)-1-[3-(8-methyl-8H-imidazo[4,5-d]thiazolo[5,4-b]pyridin-2-yl)phenyl]ethyl]-cyclohexanecarboxamide | 2.51 | 435.41 |
| A111 | 1-amino-2,3-dihydro-1H-inden-1-yl | 1-amino-2,3-dihydro-N-[(1S)-1-[3-(8-methyl-8H-imidazo[4,5-d]thiazolo[5,4-b]pyridin-2-yl)phenyl]ethyl]-1H-indene-1-carboxamide | 4.26 | 469.35 |
| A112 | 1-aminocyclopentyl | 1-amino-N-[(1S)-1-[3-(8-methyl-8H-imidazo[4,5-d]thiazolo[5,4-b]pyridin-2-yl)phenyl]ethyl]-cyclopentanecarboxamide | 2.42 | 421.41 |
| A113 | (1R,2S)-2-aminocyclopentyl | 2-amino-N-[(1S)-1-[3-(8-methyl-8H-imidazo[4,5-d]thiazolo[5,4-b]pyridin-2-yl)phenyl]ethyl]-,(1R,2S)-cyclopentanecarboxamide | 2.45 | 421.41 |
| A114 | 2-morpholinyl | N-[(1S)-1-[3-(8-methyl-8H-imidazo[4,5-d]thiazolo[5,4-b]pyridin-2-yl)phenyl]ethyl]-2-morpholinecarboxamide | 2.39 | 423.35 |
| A115 | (1R,2S)-2-aminocyclohexyl | 2-amino-N-[(1S)-1-[3-(8-methyl-8H-imidazo[4,5-d]thiazolo[5,4-b]pyridin-2-yl)phenyl]ethyl]-,(1R,2S)-cyclohexanecarboxamide | 2.53 | 435.39 |

TABLE A2-continued

| Ex. | R¹ | Name | HPLC Retention (min) | MS Reported |
|---|---|---|---|---|
| A116 | 4-methyl-piperidinyl with Me | 4-methyl-N-[(1S)-1-[3-(8-methyl-8H-imidazo[4,5-d]thiazolo[5,4-b]pyridin-2-yl)phenyl]ethyl]-4-piperidinecarboxamide | 2.44 | 435.38 |
| A117 | 3-methyl-piperidinyl | 3-methyl-N-[(1S)-1-[3-(8-methyl-8H-imidazo[4,5-d]thiazolo[5,4-b]pyridin-2-yl)phenyl]ethyl]-4-piperidinecarboxamide | 2.51 | 435.38 |
| A118 | MeHN-CH(Me)- | 2-(methylamino)-N-[(1S)-1-[3-(8-methyl-8H-imidazo[4,5-d]thiazolo[5,4-b]pyridin-2-yl)phenyl]ethyl]-(2S)-propanamide, | 2.37 | 395.41 |
| A119 | MeHN-CH2- | 2-(methylamino)-N-[(1S)-1-[3-(8-methyl-8H-imidazo[4,5-d]thiazolo[5,4-b]pyridin-2-yl)phenyl]ethyl]-acetamide | 2.31 | 381.41 |
| A120 | MeHN-C(Me)2- | 2-methyl-2-(methylamino)-N-[(1S)-1-[3-(8-methyl-8H-imidazo[4,5-d]thiazolo[5,4-b]pyridin-2-yl)phenyl]ethyl]-propanamide | 2.34 | 409.40 |
| A121 | 1-amino-cyclobutyl | 1-amino-N-[(1S)-1-[3-(8-methyl-8H-imidazo[4,5-d]thiazolo[5,4-b]pyridin-2-yl)phenyl]ethyl]-cyclobutanecarboxamide | 2.39 | 407.41 |
| A122 | 4-amino-tetrahydrothiopyranyl-SO2 | 4-aminotetrahydro-N-[(1S)-1-[3-(8-methyl-8H-imidazo[4,5-d]thiazolo[5,4-b]pyridin-2-yl)phenyl]ethyl]-1,1-dioxide-2H-thiopyran-4-carboxamide | 2.34 | 485.26 |
| A123 | H2N-C(Me)-CH2-CH(Me)2 | 3-amino-5-methyl-N-[(1S)-1-[3-(8-methyl-8H-imidazo[4,5-d]thiazolo[5,4-b]pyridin-2-yl)phenyl]ethyl]-(3S)-hexanamide | 2.73 | 437.41 |

TABLE A2-continued

| Ex. | R¹ | Name | HPLC Retention (min) | MS Reported |
|---|---|---|---|---|
| A124 | (2R)-pyrrolidin-2-yl | N-[(1S)-1-[3-(8-methyl-8H-imidazo[4,5-d]thiazolo[5,4-b]pyridin-2-yl)phenyl]ethyl]-(2R)-2-pyrrolidinecarboxamide | 2.42 | 407.41 |
| A125 | isoxazol-5-yl | N-[(1S)-1-[3-(8-methyl-8H-imidazo[4,5-d]thiazolo[5,4-b]pyridin-2-yl)phenyl]ethyl]-5-isoxazolecarboxamide | 2.92 | 405.45 |
| A126 | Ph— | N-[(1S)-1-[3-(8-methyl-8H-imidazo[4,5-d]thiazolo[5,4-b]pyridin-2-yl)phenyl]ethyl]-benzamide | 3.18 | 414.44 |
| A127 | 1-methyl-1H-pyrrol-2-yl | 1-methyl-N-[(1S)-1-[3-(8-methyl-8H-imidazo[4,5-d]thiazolo[5,4-d]pyridin-2-yl)phenyl]ethyl]-1H-pyrrole-2-carboxamide | 3.15 | 417.47 |
| A128 | 1-methyl-1H-imidazol-4-yl | 1-methyl-N-[(1S)-1-[3-(8-methyl-8H-imidazo[4,5-d]thiazolo[5,4-d]pyridin-2-yl)phenyl]ethyl]-1H-imidazole-4-carboxamide | 2.49 | 418.46 |
| A129 | 1-methyl-1H-imidazol-2-yl | 1-methyl-N-[(1S)-1-[3-(8-methyl-8H-imidazo[4,5-d]thiazolo[5,4-d]pyridin-2-yl)phenyl]ethyl]-1H-imidazole-2-carboxamide | 2.68 | 418.43 |
| A130 | 1-methyl-1H-imidazol-5-yl | 1-methyl-N-[(1S)-1-[3-(8-methyl-8H-imidazo[4,5-d]thiazolo[5,4-d]pyridin-2-yl)phenyl]ethyl]-1H-imidazole-5-carboxamide | 2.49 | 418.46 |
| A131 | thiazol-4-yl | N-[(1S)-1-[3-(8-methyl-8H-imidazo[4,5-d]thiazolo[5,4-b]pyridin-2-yl)phenyl]ethyl]-4-thiazolecarboxamide | 3.10 | 421.38 |
| A132 | 4-methylthiazol-5-yl | 4-methyl-N-[(1S)-1-[3-(8-methyl-8H-imidazo[4,5-d]thiazolo[5,4-d]pyridin-2-yl)phenyl]ethyl]-5-thiazolecarboxamide | 3.00 | 435.38 |

TABLE A2-continued

| Ex. | R¹ | Name | HPLC Retention (min) | MS Reported |
|---|---|---|---|---|
| A133 | (4-methyl-1,2,3-thiadiazol-5-yl) | N-[(1S)-1-[3-(8-methyl-8H-imidazo[4,5-d]thiazolo[5,4-b]pyridin-2-yl)phenyl]ethyl]-4-methyl-1,2,3-thiadiazole-5-carboxamide | 3.13 | 436.39 |
| A134 | (6-mercaptopyridin-3-yl) | 6-mercapto-N-[(1S)-1-[3-(8-methyl-8H-imidazo[4,5-d]thiazolo[5,4-b]pyridin-2-yl)phenyl]ethyl]-3-pyridinecarboxamide | 2.91 | 447.38 |
| A135 | (5-nitro-2-furanyl) | N-[(1S)-1-[3-(8-methyl-8H-imidazo[4,5-d]thiazolo[5,4-b]pyridin-2-yl)phenyl]ethyl]-5-nitro-2-furancarboxamide | 3.21 | 449.38 |
| A136 | (benzofuran-5-yl) | N-[(1S)-1-[3-(8-methyl-8H-imidazo[4,5-d]thiazolo[5,4-b]pyridin-2-yl)phenyl]ethyl]-5-benzofurancarboxamide, | 3.38 | 454.41 |
| A137 | (1,2-dimethyl-1H-benzimidazol-5-yl) | 1,2-dimethyl-N-[(1S)-1-[3-(8-methyl-8H-imidazo[4,5-d]thiazolo[5,4-b]pyridin-2-yl)phenyl]ethyl]-1H-benzimidazole-5-carboxamide | 2.59 | 484.41 |
| A138 | (1-isopropyl-1H-benzotriazol-5-yl) | N-[(1S)-1-[3-(8-methyl-8H-imidazo[4,5-d]thiazolo[5,4-b]pyridin-2-yl)phenyl]ethyl]-1-(1-methylethyl)-1H-1,2,3-benzotriazole-5-carboxamide | 3.33 | 497.39 |
| A139 | (2-oxo-2,3-dihydro-1H-benzimidazol-5-yl) | 2,3-dihydro-N-[(1S)-1-[3-(8-methyl-8H-imidazo[4,5-d]thiazolo[5,4-b]pyridin-2-yl)phenyl]ethyl]-2-oxo-1H-benzimidazole-5-carboxamide | 2.89 | 470.39 |
| A140 | NC-C(CH₃)₂- | 2-cyano-N-[(1S)-1-[3-(8-methyl-8H-imidazo[4,5-d]thiazolo[5,4-b]pyridin-2-yl)phenyl]ethyl]-acetamide | 3.10 | 377.30 |

Example A141 alpha,alpha-dimethyl-3-(8-methyl-8H-imdazo[4,5-d]thiazolo[5,4-b]pyridin-2-yl)-benzeneacetic acid

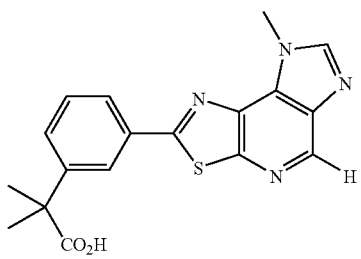

A141

A141.1 Ethyl 2-(3-(4,4,5,5-tetramethyl-1,3,2-dioxaborolan-2-yl)phenyl)-2-methylpropanoate

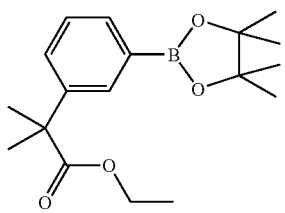

A141.1

A141.1 was prepared from A6.1b in a similar manner to that described for the preparation of A6.1.

A141.2. alpha,alpha-dimethyl-3-(7-chloro-8-methyl-8H-imidazo[4,5-d]thiazolo[5,4-b]pyridin-2-yl)-benzeneacetic acid ethyl ester

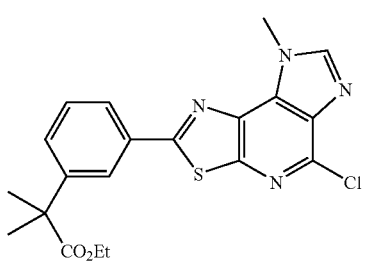

A141.2

A solution of A1.8 (1.0 g, 3.14 mmol), A141.1 (0.867 g, 2.86 mmol), tetrakis(triphenylphosphine)palladium (0.166 g, 0.14 mmol), and potassium carbonate (2N aq., 3.6 mL) in DME (50 mL) was placed in heavy walled pressure vessel. The vessel was flushed with argon, sealed and placed in an oil bath at 120° C. for 16 hours. The DME was evaporated under vacuum, and the residue partitioned between chloroform and water. The aqueous phase was extracted with chloroform and the combined organic phases were dried over magnesium sulfate, filtered, and concentrated to dryness. The residue was purified by silica gel flash chromatography (0-5% methanol/dichloromethane) to afford A141.2 (0.436 g) as an off-white solid. HPLC retention time 4.18 min. Column:Chromolith SpeedROD 4.6×50 mm (4 min grad. 0% B-100% B) Solvent A: 10% MeOH-90% $H_2O$ 0.1% TFA Solvent B: 90% MeOH-10% $H_2O$-0.1% TFA. MS (ES): m/z 415.2, 417.2 $[M+H]^+$

A141.3: alpha,alpha-dimethyl-3-(8-methyl-8H-imidazo[4,5-d]thiazolo[5,4-b]pyridin-2-yl)-benzeneacetic acid A solution of A141.2 (0.4 g, 0.96 mmol), Pd/C (10%, 0.20 g) and ammonium formate (0.60 g) in isopropyl alcohol (125 mL) was heated to 65° C. for 4 hours. The reaction was passed through a membrane filter, washed with methanol then evaporated to dryness. The crude reduction product thus obtained (0.346 g) was used without further purification. The crude ester product was dissolved in THF (5 mL), methanol (10 mL), and aq. sodium hydroxide (2N, 4 mL). The reaction was heated to 65° C. overnight. The solvents were evaporated to near dryness and the residue partitioned between water (pH>10) and ethyl acetate. The aq. phase was evaporated to remove residual ethyl acetate then acidified to pH ~3. The resulting precipitate was collected by filtration and air dried to give A141 (0.295 g) as an off-white solid. HPLC retention time 3.46 min. Column:Chromolith SpeedROD 4.6×50 mm (4 min grad. 0% B-100% B) Solvent A: 10% MeOH-90% $H_2O$ 0.1% TFA Solvent B: 90% MeOH-10% $H_2O$-0.1% TFA. MS (ES): m/z 353.2 $[M+H]^+$

Example A142 alpha,alpha-dimethyl-3-(8-methyl-8H-imidazo[4,5-d]thiazolo[5,4-b]pyridin-2-yl)-N-propylbenzeneacetamide

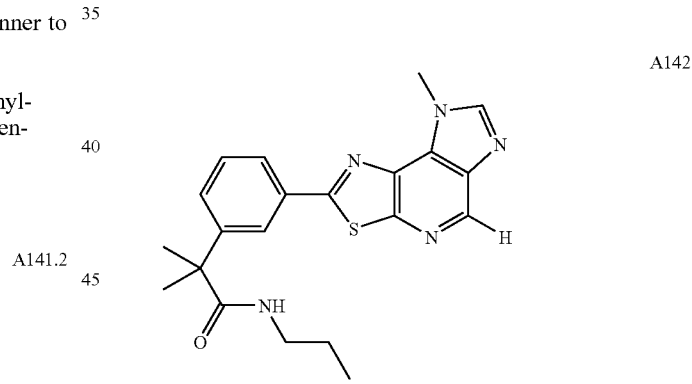

A142

A solution of A141 (0.0175 g, 0.05 mmol), n-propylamine (0.0082 mL, 0.099 mmol), EDCI (0.0143 g, 0.075 mmol), HOBt (0.0101 g, 0.075 mmol) in NMP (0.5 mL) was heated to 65° C. for 16 hours. Upon cooling to room temperature water was added and the solution was extracted with chloroform. The organic phase was purified by silica gel flash chromatography (0-15% methanol/dichloromethane) to afford A142 (0.0113 g) as an off-white solid. HPLC retention time 3.37 min. Column:Chromolith SpeedROD 4.6×50 mm (4 min grad. 0% B-100% B) Solvent A: 10% MeOH-90% $H_2O$ 0.1% TFA Solvent B: 90% MeOH-10% $H_2O$-0.1% TFA. MS (ES): m/z 394.2 $[M+H]^+$

Examples A143-A159

Examples A143-A159 was prepared starting with carboxylate A141 and the appropriate amine precursor using the following general procedure: The examples described in Table A3 were prepared by a solution phase library methodology. To an individual well of a 48-position MiniBlock® reactor was added 112 μL of a 0.50 M solution of the appropriate amine in dimethylacetamide (DMA) (0.056 mmol, 1.7 equiv); 60 μL of a 0.93 M solution of 1-hydroxybenzotriazol in DMA (0.056 mmol, 1.7 equiv); 46 mg of polystyrene-supported N,N'-diisopropylcarbodiimide (PS-DIC) (1.21 mmol/g, 1.7 equiv); and 330 μL of 1,2-dichloroethane (DCE). The reactor was agitated via orbital shaker for 10 min. Finally, 300 μL of a 0.11 M solution of A141 in DMA (0.033 mmol, 1.0 equiv) was added to the reactor well, and the reactor was agitated for 14 h at rt. The crude product was filtered, rinsed with additional DMA, then purified by standard preparative HPLC-MS ($H_2O$/MeOH/0.1% TFA, gradient 35-90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS $H_2O$/MeOH/0.1% TFA, gradient 10-90% MeOH over 4 min, 4 mL/min, 4.6×50 mm 5 um Phenomenex® Primesphere column Retention time and observed mass are reported.

TABLE A3

| Ex. | R¹ | Name | HPLC Retention (min) | MS Reported |
|---|---|---|---|---|
| A143 | —NHMe | N,alpha,alpha-trimethyl-3-(8-methyl-8H-imidazol[4,5-d]thiazolo[5,4-b]pyridin-2-yl)-benzeneacetamide | 2.93 | 366.48 |
| A144 | —NHEt | N-ethyl-alpha,alpha-dimethyl-3-(8-methyl-8H-imidazol[4,5-d]thiazolo[5,4-b]pyridin-2-yl)-benzeneacetamide | 3.09 | 380.48 |
| A145 | —NHiPr | alpha,alpha-dimethyl-N-(1-methylethyl)-3-(8-methyl-8H-imidazo[4,5-d]thiazolo[5,4-b]pyridin-2-yl)-benzeneacetamide | 3.23 | 394.48 |
| A146 | 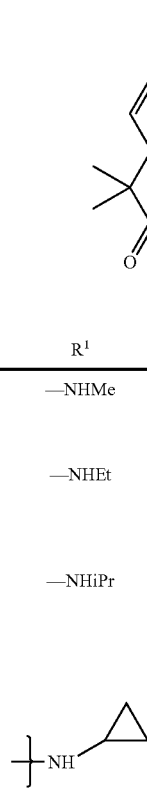 | N-cyclopropyl-alpha,alpha-dimethyl-3-(8-methyl-8H-imidazo[4,5-d]thiazolo[5,4-b]pyridin-2-yl)-benzeneacetamide | 3.11 | 392.48 |
| A147 | —NHN(Me)₂ | N-alpha,alpha-dimethyl-3-(8-methyl-8H-imidazo[4,5-d]thiazolo[5,4-b]pyridin-2-yl)-benzeneacetic acid-2,2-dimethylhydrazide | 2.67 | 395.48 |
| A148 | 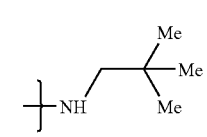 | N-(2,2-dimethylpropyl)-alpha,alpha-dimethyl-3-(8-methyl-8H-imidazo[4,5-d]thiazolo[5,4-b]pyridin-2-yl)-benzeneacetamide | 3.58 | 422.48 |
| A149 | 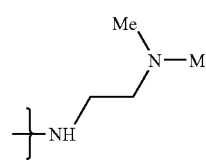 | N-[2-(dimethylamino)ethyl]-alpha,alpha-dimethyl-3-(8-methyl-8H-imidazo[4,5-d]thiazolo[5,4-b]pyridin-2-yl)-benzeneacetamide | 2.58 | 423.48 |
| A150 | —N(Me)₂ | N,N,alpha,alpha-tetramethyl-3-(8-methyl-8H-imidazo[4,5-d]thiazolo[5,4-b]pyridin-2-yl)-benzeneacetamide, | 3.17 | 380.48 |

TABLE A3-continued

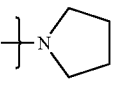

| Ex. | R¹ | Name | HPLC Retention (min) | MS Reported |
|---|---|---|---|---|
| A151 | 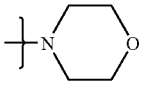 | 1-[2-methyl-2-[3-(8-methyl-8H-imidazo[4,5-d]thiazolo[5,4-b]pyridin-2-yl)phenyl]-1-oxopropyl]-pyrrolidine, | 3.38 | 406.48 |
| A152 | 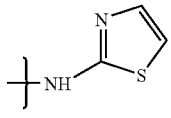 | 4-[2-methyl-2-[3-(8-methyl-8H-imidazo[4,5-d]thiazolo[5,4-b]pyridin-2-yl)phenyl]-1-oxopropyl]-morpholine | 3.12 | 422.46 |
| A153 |  | alpha,alpha-dimethyl-3-(8-methyl-8H-imidazo[4,5-d]thiazolo[5,4-b]pyridin-2-yl)-N-2-thiazolyl-benzeneacetamide | 3.42 | 435.39 |
| A154 | 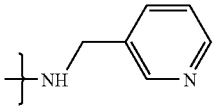 | alpha,alpha-dimethyl-3-(8-methyl-8H-imidazo[4,5-d]thiazolo[5,4-b]pyridin-2-yl)-N-(phenylmethyl)-benzeneacetamide | 3.42 | 442.43 |
| A155 | 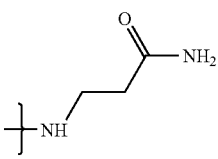 | alpha,alpha-dimethyl-3-(8-methyl-8H-imidazo[4,5-d]thiazolo[5,4-b]pyridin-2-yl)-N-(3-pyridinylmethyl)-benzeneacetamide | 2.63 | 443.43 |
| A156 | 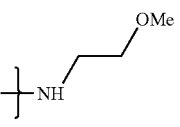 | N-(3-amino-3-oxopropyl)-alpha,alpha-dimethyl-3-(8-methyl-8H-imidazo[4,5-d]thiazolo[5,4-b]pyridin-2-yl)-benzeneacetamide | 2.80 | 423.41 |
| A157 | 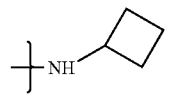 | N-(2-methoxyethyl)-alpha,alpha-dimethyl-3-(8-methyl-8H-imidazo[4,5-d]thiazolo[5,4-b]pyridin-2-yl)-benzeneacetamide | 3.06 | 410.48 |
| A158 | 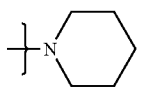 | N-cyclobutyl-alpha,alpha-dimethyl-3-(8-methyl-8H-imidazo[4,5-d]thiazolo[5,4-b]pyridin-2-yl)-benzeneacetamide | 3.31 | 406.46 |
| A159 |  | 1-[2-methyl-2-[3-(8-methyl-8H-imidazo[4,5-d]thiazolo[5,4-b]pyridin-2-yl)phenyl]-1-oxopropyl]-piperidine | 3.55 | 420.47 |

Examples A160-A181

The compounds in Table A4 were prepared in a similar manner for those described in Table A1 starting with amine A34 and the in place of a carboxylic acid and PS-DIC the appropriate haloformate to form carbamates, sulfonylhalide to form sulfonamides or isocyanate to form ureas were used.

TABLE A4

| Ex. | R¹ | Name | HPLC Retention (min) | MS Reported |
|---|---|---|---|---|
| A160 | MeO-C(=O)-C(Me)₂- | [(1S)-1-[3-(8-methyl-8H-imidazo[4,5-d]thiazolo[5,4-b]pyridin-2-yl)phenyl]ethyl]-carbamic acid, methyl ester | 2.94 | 368.47 |
| A161 | PhCH₂O-C(=O)-C(Me)₂- | [(1S)-1-[3-(8-methyl-8H-imidazo[4,5-d]thiazolo[5,4-b]pyridin-2-yl)phenyl]ethyl]-carbamic acid, phenylmethyl ester | 3.51 | 444.42 |
| A162 | PrO-C(=O)-C(Me)₂- | [(1S)-1-[3-(8-methyl-8H-imidazo[4,5-d]thiazolo[5,4-b]pyridin-2-yl)phenyl]ethyl]-carbamic acid, propyl ester | 3.32 | 396.48 |
| A163 | Ph-NH-C(=O)-C(Me)₂- | N-[(1S)-1-[3-(8-methyl-8H-imidazo[4,5-d]thiazolo[5,4-b]pyridin-2-yl)phenyl]ethyl]-N'-phenyl-urea | 3.33 | 429.48 |
| A164 | (Me)₃C-NH-C(=O)-C(Me)₂- | N-(1,1-dimethylethyl)-N'-[(1S)-1-[3-(8-methyl-8H-imidazo[4,5-d]thiazolo[5,4-b]pyridin-2-yl)phenyl]ethyl]-urea | 3.23 | 409.52 |
| A165 | (Me)₂CH-NH-C(=O)-C(Me)₂- | N-(1-methylethyl)-N'-[(1S)-1-[3-(8-methyl-8H-imidazo[4,5-d]thiazolo[5,4-b]pyridin-2-yl)phenyl]ethyl]-urea | 2.98 | 395.50 |
| A166 | MeCH₂-NH-C(=O)-C(Me)₂- | N-ethyl-N'-[(1S)-1-[3-(8-methyl-8H-imidazo[4,5-d]thiazolo[5,4-b]pyridin-2-yl)phenyl]ethyl]-urea | 2.82 | 381.48 |
| A167 | MeCH₂CH₂-NH-C(=O)-C(Me)₂- | N-[(1S)-1-[3-(8-methyl-8H-imidazo[4,5-d]thiazolo[5,4-b]pyridin-2-yl)phenyl]ethyl]-N'-propyl-urea | 3.02 | 395.50 |
| A168 | Ph-SO₂-C(Me)₂- | N-[(1S)-1-[3-(8-methyl-8H-imidazol[4,5-d]thiazolo[5,4-b]pyridin-2-yl)phenyl]ethyl]-benzenesulfonamide | 3.20 | 450.35 |
| A169 | F₃C-SO₂-C(Me)₂- | 1,1,1-trifluoro-N-[(1S)-1-[3-(8-methyl-8H-imidazo[4,5-d]thiazolo[5,4-b]pyridin-2-yl)phenyl]ethyl]-methanesulfonamide | 3.53 | 442.35 |

TABLE A4-continued

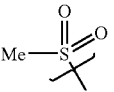

| Ex. | R[1] | Name | HPLC Retention (min) | MS Reported |
|---|---|---|---|---|
| A170 | 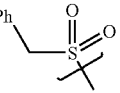 | N-[(1S)-1-[3-(8-methyl-8H-imidazo[4,5-d]thiazolo[5,4-b]pyridin-2-yl)phenyl]ethyl]-methanesulfonamide | 2.71 | 388.44 |
| A171 | 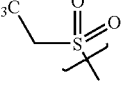 | N-[(1S)-1-[3-(8-methyl-8H-imidazo[4,5-d]thiazolo[5,4-b]pyridin-2-yl)phenyl]ethyl]-benzenemethanesulfonamide | 3.30 | 464.36 |
| A172 | 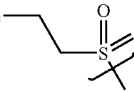 | N-[(1S)-1-[3-(8-methyl-8H-imidazo[4,5-d]thiazolo[5,4-b]pyridin-2-yl)phenyl]ethyl]-2,2,2-trifluoro-ethanesulfonamide | 3.07 | 456.33 |
| A173 | 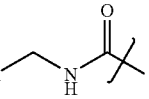 | N-[(1S)-1-[3-(8-methyl-8H-imidazol[4,5-d]thiazolo[5,4-b]pyridin-2-yl)phenyl]ethyl]-1-propanesulfonamide | 3.04 | 416.42 |
| A174 | 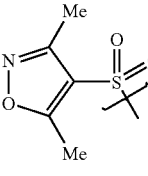 | N-[(1S)-1-[3-(8-methyl-8H-imidazo[4,5-d]thiazolo[5,4-b]pyridin-2-yl)phenyl]ethyl]-N'-(phenylmethyl)-urea | 3.22 | 443.47 |
| A175 | 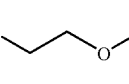 | -N-[(1S)-1-[3-(8-methyl-8H-imidazo[4,5-d]thiazolo[5,4-b]pyridin-2-yl)phenyl]ethyl]-3,5-dimethyl-4-isoxazolesulfonamide | 3.08 | 469.35 |
| A176 | 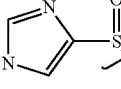 | [(1S)-1-[3-(8-methyl-8H-imidazo[4,5-d]thiazolo[5,4-b]pyridin-2-yl)phenyl]ethyl]-carbamic acid,-2-methoxyethyl ester | 2.95 | 412.48 |
| A177 | 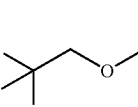 | 1-methyl-N-[(1S)-1-[3-(8-methyl-8H-imidazo[4,5-d]thiazolo[5,4-b]pyridin-2-yl)phenyl]ethyl]-1H-imidazole-4-sulfonamide | 2.63 | 454.37 |
| A178 | | [(1S)-1-[3-(8-methyl-8H-imidazo[4,5-d]thiazolo[5,4-b]pyridin-2-yl)phenyl]ethyl]-carbamic acid-2,2-dimethylpropyl ester | 3.63 | 424.48 |

TABLE A4-continued

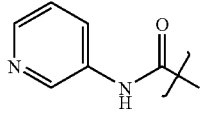

| Ex. | R¹ | Name | HPLC Retention (min) | MS Reported |
|---|---|---|---|---|
| A179 | | N-[(1S)-1-[3-(8-methyl-8H-imidazo[4,5-d]thiazolo[5,4-b]pyridin-2-yl)phenyl]ethyl]-N'-3-pyridinyl-urea | 2.52 | 430.44 |
| A180 | | N-[(1S)-1-[3-(8-methyl-8H-imidazo[4,5-d]thiazolo[5,4-b]pyridin-2-yl)phenyl]ethyl]-cyclopropanesulfonamide | 2.93 | 414.43 |
| A181 | | N-[(1S)-1-[3-(8-methyl-8H-imidazo[4,5-d]thiazolo[5,4-b]pyridin-2-yl)phenyl]ethyl]-3-pyridinesulfonamide | 2.85 | 451.36 |

Examples A182-A195

The compounds in Table A5 were prepared in a similar manner for those described in Table A1 starting with amine A34 and the appropriate carboxylic acid.

TABLE A5

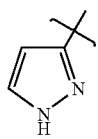

| Ex. | R¹ | Name | HPLC Retention (min) | MS Reported |
|---|---|---|---|---|
| A182 | | N-[(1S)-1-[3-(8-methyl-8H-imidazo[4,5-d]thiazolo[5,4-b]pyridin-2-yl)phenyl]ethyl]-1H-pyrazole-3-carboxamide | 2.83 | 404.48 |

TABLE A5-continued

| Ex. | R¹ | Name | HPLC Retention (min) | MS Reported |
|---|---|---|---|---|
| A183 | | N-[(1S)-1-[3-(8-methyl-8H-imidazo[4,5-d]thiazolo[5,4-b]pyridin-2-yl)phenyl]ethyl]-1H-imidazole-2-carboxamide | 2.54 | 404.51 |
| A184 | | N-[(1S)-1-[3-(8-methyl-8H-imidazo[4,5-d]thiazolo[5,4-b]pyridin-2-yl)phenyl]ethyl]-1H-pyrrole-2-carboxamide | 2.95 | 403.49 |
| A185 | | N-[(1S)-1-[3-(8-methyl-8H-imidazo[4,5-d]thiazolo[5,4-b]pyridin-2-yl)phenyl]ethyl]-1H-pyrazole-4-carboxamide | 2.76 | 404.47 |
| A186 | | N-[(1S)-1-[3-(8-methyl-8H-imidazo[4,5-d]thiazolo[5,4-b]pyridin-2-yl)phenyl]ethyl]-1H-imidazole-4-carboxamide, | 2.41 | 404.48 |
| A187 | | 3-(1H-imidazol-4-yl)-N-[(1S)-1-[3-(8-methyl-8H-imidazo[4,5-d]thiazolo[5,4-b]pyridin-2-yl)phenyl]ethyl]-, (2E)-2-propenamide | 2.49 | 430.44 |
| A188 | | N-[(1S)-1-[3-(8-methyl-8H-imidazo[4,5-d]thiazolo[5,4-b]pyridin-2-yl)phenyl]ethyl]-4-nitro-1H-pyrrole-2-carboxamide | 3.16 | 448.42 |
| A189 | | N-[(1S)-1-[3-(8-methyl-8H-imidazo[4,5-d]thiazolo[5,4-b]pyridin-2-yl)phenyl]ethyl]-5-nitro-1H-pyrazole-3-carboxamide | 3.12 | 449.38 |
| A190 | | N-[(1S)-1-[3-(8-methyl-8H-imidazo[4,5-d]thiazolo[5,4-b]pyridin-2-yl)phenyl]ethyl]-4-nitro-1H-pyrazole-3-carboxamide | 2.95 | 449.41 |

TABLE A5-continued

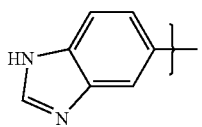

| Ex. | R¹ | Name | HPLC Retention (min) | MS Reported |
|---|---|---|---|---|
| A191 | 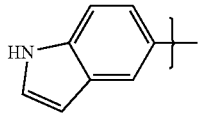 | N-[(1S)-1-[3-(8-methyl-8H-imidazo[4,5-d]thiazolo[5,4-b]pyridin-2-yl)phenyl]ethyl]-1H-benzimidazole-5-carboxamide | 2.55 | 454.43 |
| A192 | 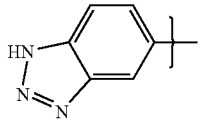 | N-[(1S)-1-[3-(8-methyl-8H-imidazo[4,5-d]thiazolo[5,4-b]pyridin-2-yl)phenyl]ethyl]-1H-indole-5-carboxamide | 3.17 | 453.44 |
| A193 | 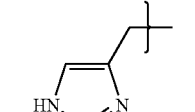 | N-[(1S)-1-[3-(8-methyl-8H-imidazo[4,5-d]thiazolo[5,4-b]pyridin-2-yl)phenyl]ethyl]-1H-1,2,3-benzotriazole-5-carboxamide | 3.02 | 455.40 |
| A194 | 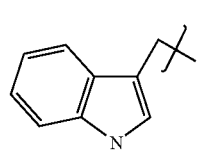 | N-[(1S)-1-[3-(8-methyl-8H-imidazo[4,5-d]thiazolo[5,4-b]pyridin-2-yl)phenyl]ethyl]-1H-imidazole-4-acetamide | 2.34 | 418.48 |
| A195 | | N-[(1S)-1-[3-(8-methyl-8H-imidazo[4,5-d]thiazolo[5,4-b]pyridin-2-yl)phenyl]ethyl]-1H-indole-3-acetamide | 3.20 | 467.42 |

Example A196

3-(8-methyl-8H-imidazo[4,5-d]thiazolo[5,4-b]pyridin-2-yl)-benzenemethanamine

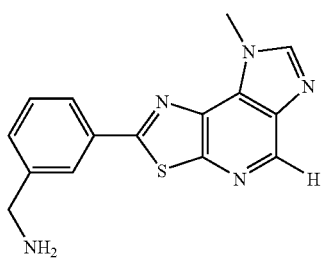

A196

Example A196 was prepared in an analogous manner to Example A6, with the exception of utilizing commercially available 3-(N-BOC-aminomethyl)phenylboronic acid in place of A6.1. HPLC retention time 2.28 min. Column:Chromolith SpeedROD 4.6×50 mm (4 min grad. 0% B-100% B) Solvent A: 10% MeOH-90% H₂O 0.1% TFA Solvent B: 90% MeOH-10% H₂O-0.1% TFA. MS (ES): m/z 296.2 [M+H]⁺

Examples A197-A1200

The compounds in Table A6 were prepared in a similar manner for those described in Table A1 starting with amine A196 and the appropriate carboxylic acid.

TABLE A6

| Ex. | R¹ | Name | HPLC Retention (min) | MS Reported |
|---|---|---|---|---|
| A197 | CH₃— | acetamide, N-[[3-(8-methyl-8H-imidazo[4,5-d]thiazolo[5,4-b]pyridin-2-yl)phenyl]methyl] | 3.07 | 338.28 |
| A198 | -O—N⁺(pyridyl)— | N-[[3-(8-methyl-8H-imidazo[4,5-d]thiazolo[5,4-b]pyridin-2-yl)phenyl]methyl]-, 4-pyridinecarboxamide-1-oxide | 3.07 | 417.29 |
| A199 | N-methylpiperidin-4-yl | 1-methyl-N-[[3-(8-methyl-8H-imidazo[4,5-d]thiazolo[5,4-b]pyridin-2-yl)phenyl]methyl]-4-piperidinecarboxamide | 2.69 | 421.37 |
| A200 | NC—C(CH₃)₂— | 2-cyano-N-[[3-(8-methyl-8H-imidazo[4,5-d]thiazolo[5,4-b]pyridin-2-yl)phenyl]methyl]-acetamide | 3.04 | 363.29 |

Utility

The compounds of the invention are inhibitors of IKK. Accordingly, compounds of formula (I) have utility in treating conditions were a decrease in NF-κB activity would be beneficial. Such conditions include diseases or disorders in which cytokine levels are modulated as a consequence of intracellular signaling via IKK, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its symptoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "IKK," this means that either or both IKK-2 and IKK-1 are inhibited.

In view of their activity as inhibitors of IKK, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, scleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Grave's disease. The inventive compounds may be used to infectious diseases such as sepsis, septic shock, Shigellosis, and *Helicobacter Pylori*.

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatitis B, and hepatitis C), HIV infection and CMV retinitis, AIDS/ARC or malignancy, and herpes.

The inventive compounds also may be used to treat angiogenic disorders including solid tumors, ocular neovascularization, and infantile haemangiomas.

In addition, IKK inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer including without limitation epithelial cancer and adenocarcinoma.

In addition, IKK (+/−) mice when fed a high fat diet have reduced insulin levels and reduced blood glucose levels. Accordingly compound of this invention are useful in the treatment of Type II diabetes (also known as non-insulin dependant diabetes).

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormome replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

The inventive compounds are also effective in treating oncological diseases, in treating cancer and tumors, such as solid tumors, lymphomas and leukemia, and in particular, breast cancer, prostate cancer, and Hodgkin's lymphoma.

Additionally this invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid or liquid tumors which are associated with IKK, especially those tumors which are significantly dependent on IKK for their growth and spread, including for example, hematopoietic tumors, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of the skin, including melanoma;

hematopoietic tumors including those of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

hematopoietic tumors including those of plasma cell lineage such as multiple myeloma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seninoma, teratocarcinoma, osteosarcoma, xenoderoma pigmentosum, keratoctanthoma, thyroid follicular cancer and Kaposi's sarcoma.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of IKK kinase activity, such as melanomas, and multiple myeloma. By the administration of a composition (or a combination) of the compounds of this invention, development of tumors in a mammalian host is reduced.

The invention also provides a pharmaceutical composition comprising a compound of formula I in combination with pharmaceutically acceptable carrier and an anti-cancer or cytotoxic agent. In a preferred embodiment said anti-cancer or cytotoxic agent is selected from the group consisting of linomide; inhibitors of integrin αvβ3 function; angiostatin; razoxin; tamoxifen; toremifen; raloxifene; droloxifene; iodoxyfene; megestrol acetate; anastrozole; letrazole; borazole; exemestane; flutamide; nilutamide; bicalutamide; cyproterone acetate; gosereline acetate; luprolide; finasteride; metalloproteinase inhibitors; inhibitors of urokinase plasminogen activator receptor function; growth factor antibodies; growth factor receptor antibodies such as Avastin® and Erbitux®; tyrosine kinase inhibitors; serine/threonine kinase inhibitors); methotrexate; 5-fluorouracil; purine; adenosine analogues; cytosine arabinoside; doxorubicin; daunomycin; epirubicin; idarubicin; mitomycin-C; dactinomycin; mithramycin); cisplatin; carboplatin; nitrogen mustard; melphalan; chlorambucil; busulphan; cyclophosphamide; ifosfamide nitrosoureas; thiotephan; vincristine; Taxol®; Taxotere®; epothilone analogs; discodermolide analogs; eleutherobin analogs; etoposide; teniposide; amsacrine; topotecan; and flavopyridols.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

1: antiangiogenic agents such as inhibitors of VEGF or related kinases (such as FLT, or KDR), linomide, antibodies which block angiogenesis, inhibitors of integrin αvβ3 function, angiostatin, razoxin;

2: cytostatic agents such as antiestrogens (for example tamoxifen, toremifen, raloxifene, droloxifene, iodoxyfene), progestogens (for example megestrol acetate), aromatase inhibitors (for example anastrozole, letrazole, borazole, exemestane), antiharmones, antiprogestogens, antiandrogens (for example flutamide, nilutamide, bicalutamide, cyproterone acetate), LHRH agonists and antagonists (for example gosereline acetate, luprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies such as Avastin® and Erbitux®, tyrosine kinase inhibitors and serine/threonine kinase inhibitors);

3: antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotephan); antimitotic agents (for example vinca alkaloids like vincristine and taxoids like Taxol®, Taxotere® and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols).

The present invention thus provides methods for treating such conditions, comprising administering to a subject in need thereof an effective amount of at least one compound of formula I or a salt thereof. Other therapeutic agents such as those described herein may be employed in combination with compounds of formula I. In the methods of the present invention, such other therapeutic agent(s) may be administered prior to, simultaneously with, or following administration of the inventive compound(s).

When the terms "IKK associated condition" or "IKK associated disease or disorder" are used herein, each is intended to encompass all of the conditions identified above as if repeated at length, as well as any other condition that is modulated by IKK kinase activity.

The present invention thus provides methods for treating such conditions, comprising administering to a subject in need thereof an effective amount of at least one compound of Formula (I), or a pharmaceutically-acceptable salt, hydrate, or prodrug thereof. The methods of treating IKK kinase-associated conditions may comprise administering compounds of Formula (I) alone or in combination with each other and/or other suitable therapeutic agents such as anti-inflammatory drugs, antibiotics, anti-viral agents, anti-oxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CeliCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, therapies for the treatment of irritable bowel syndrome (e.g., Zelmac®, Zelnorm®, and Maxi-K® openers such as those disclosed in U.S. Pat. No. 6,184,231 B1), corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan, or with opioids (e.g. morphine, codeine, hydomorphone).

Examples of suitable diabetic agents with which the inventive compounds may be used include insulin (of porcine or recombinant human origin including, short acting insulins such as Humalog®, Regular, intermediate acting insulins such NPH, lente, and long acting insulins such as ultralente or glarginine(Lantus®)); sulfonylureas such as glyburide and glipizide; secretegogues such as repaginide, and nateglinide; Peroisome proliferators-activated receptor (PPAR) agonists such as rosiglitazone and pioglitazone, and mixed PPAR alpha/gamma dual agonists such as muriglitazar; biquamides such as metformin, and glucosidase inhibitors such as acarbose and miglitol, PPAR-alpha agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

Examples of suitable antibiotics with which the inventive compounds may be used include β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steriodal or non-steroidal progesterone receptor agonists ("PRA"), such as levonorgestrel, medroxyprogesterone acetate (MPA).

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive compounds may also be useful in combination with anticancer strategies and chemotherapies such as taxol and/or cisplatin. The compounds may be used in conjunction with antitumor agents such as paclitaxel, adriamycin, epithilones, cisplatin, and carboplatin.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 60/339,108, filed Dec. 10, 2001 and assigned to the present assignee; -alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); K$^+$ channel modulators such as I$_{Ach}$ inhibitors and inhibitors of the K$_v$1 subfamily of K$^+$ channel openers such as I$_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), P2Y$_1$ and P2Y$_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolinmine, bumetanide, triamtrenene, and amiloride.

Additionally, the inventive compounds may be used in combination with lipid profile modulators and antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal Na$^+$/bile acid cotransporter inhibitors, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alphalbeta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of IKK enzyme activity.

The inventive compounds have been tested and have shown activity as inhibitors of IKK, IkB, NF-κB and/or TNF-α. For example, THP-1 (human monocytic cell line) obtained from ATCC was cultured in RPMI-1640 supplemented with 10% FBS, sodium pyruvate, HEPES, 5-mercaptoethanol, Penicillin/Streptomycin. To a 96-well plate containing THP-1 cells (1.4×10$^6$/mL, 2.5×10$^5$ cells/well) in 180 μL RPMI-1640 was added 10 μL of the test compound in 10% DMSO. Typically, test compound concentrations of 0.1-100 μM were used in the assay. After one hour at 37° C., 10 μL of 1000 ng/mL lipopolysaccharide (LPS from *Salmonella typhosa*, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. The compounds of this invention are active in vivo in the LPS-induced TNFα secretion model. Likewise, assays known in the field are applied to establish the activity of the compounds as inhibitors of IKK, IkB, and/or the NF-κB pathway.

TNFα Secretion Assay

The ability of compounds to inhibit the production and secretion of TNFα from leukocytes was performed using either PBMC (obtained as described above) or the THP-1 cell line as a source of monocytes. Compounds were diluted in RPMI 1640 supplemented with 10% FBS and DMSO at a final concentration of 0.2%. Cells (2×105/well in U-bottom 96 well plates) were pre-incubated with compounds for 30 min at 37 C prior to addition of lipopolysaccharide (LPS) at a final concentration of 6.25 ng/ml in a total volume of 200 μL. After 4 h at 37° C., 50 μL of supernatant was carefully aspirated for detection of soluble TNFα. Soluble TNFα was detected by ELISA developed by R&D Systems (Minneapolis, Minn.) according to the manufacturer's instructions.

We claim:
1. A compound of formula (I),

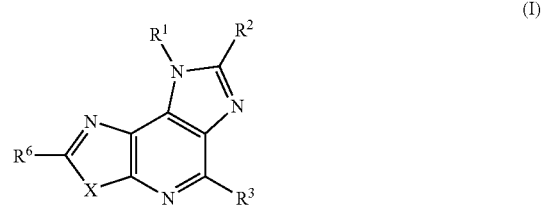

enantiomers, diastereomers, and salts, thereof wherein
X is S;
$R^1$ is selected from hydrogen, and $C_{1-3}$ alkyl;
$R^2$ is hydrogen or alkyl;
$R^3$ is hydrogen;
$R^6$ is
$R^6$ is

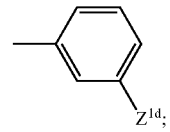

$Z^{1d}$, is —$W^1$—$V^1$;
where $W^1$ is alkyl; and
$V^1$ is
—$U^1$—$NH_2$, or
—$U^1$—$N(Y^4)$—$C(O)$—$Y^1$,
$Y^1$ and $Y^4$
(1) are each independently hydrogen, alkyl, (hydroxy)alkyl, (alkoxy)alkyl, alkenyl, alkynyl, cycloalkyl, aryl, -heterocyclo, (heterocylco)alkyl, heteroaryl, or (heteroaryl)alkyl, where heterocyclo is selected from azetidinyl, morpholinyl, 5-oxo-2-pyrrolidinyl, piperidinyl, pyrazolyl, pyrrolidinyl, tetrahydrofuranyl, and where heteroaryl is selected from benzofuranyl, benzimidazolyl, benzotriazolyl, 1,1-dioxide-2H-thiopyranyl, furanyl, imidazolyl, indolyl, isoxazolyl, 2-oxo-1H-benzimidazolyl, pyrazinyl, pyridinyl-1-oxide, pyridinyl, pyridazinyl, pyrrolyl, thiadiazolyl, or thiazolyl, any of which may be optionally independently substituted as valence allows with one or more $Z^4$, $Z^5$ and $Z^6$;
$Z^4$, $Z^5$, and $Z^6$ are optional substituents at each occurrence independently selected from
(1) H
(2) alkyl, or aryl;
(3) —$U^1$—O—$Y^{5a}$,
(4) —$U^1$—S—$Y^{5a}$,
(5) —$U^1$—$C(O)_t$—H, —$U^1$—$C(O)_t$—$Y^{5a}$ where t is 1 or 2,
(6) —$U^1$—$SO_3$—H, or —$U^1$—$S(O)_t Y^{5a}$,
(7) —$U^1$-halo,
(8) —$U^1$-cyano,
(9) —$U^1$-nitro,
(10) —$U^1$—$NY^{2a}Y^{3a}$,
(11) —$U^1$—$C(O)_2$—$NY^{2a}Y^{3a}$,
(12) —$U^1$—$S(O)_2$—$N(Y^{4a})$—$Y^{1a}$,
(13) oxo;

$Y^{1a}, Y^{2a}, Y^{3a}, Y^{4a}$ and $Y^{5a}$
  (1) are each independently hydrogen, or alkyl;
$U^1$ is independently
  (1) a single bond,
  (2) alkylene,
  (3) alkenylene, or
  (4) alkynylene.

2. A compound of claim 1 wherein
$R^1$ is hydrogen, methyl, ethyl, propyl, or i-propyl; and
$R^2$ is hydrogen, or methyl.

3. A compound of claim 1 wherein
$U^1$ is a bond or alkylene.

4. A compound of claim 1 wherein
$R^1$ is $C_{1-3}$ alkyl; and
$R^2$ is hydrogen.

5. A pharmaceutical composition comprising (a) at least one compound according to claim 1, or a pharmaceutically acceptable salt thereof, and (b) a pharmaceutically-acceptable carrier or diluent.

6. A pharmaceutical composition comprising (a) at least one compound according to claim 4, or a pharmaceutically acceptable salt thereof, and (b) a pharmaceutically-acceptable carrier or diluent.

\* \* \* \* \*